(12) United States Patent
Walker et al.

(10) Patent No.: US 8,206,936 B2
(45) Date of Patent: *Jun. 26, 2012

(54) ANTIBODY CATEGORIZATION BASED ON BINDING CHARACTERISTICS

(75) Inventors: Wynn L. Walker, Palo Alto, CA (US); Michael L. Gallo, North Vancouver (CA); Xiao-Chi Jia, San Mateo, CA (US); Keith Joho, San Jose, CA (US); Jaspal Singh Kang, Surrey (CA)

(73) Assignee: Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/823,104

(22) Filed: Jun. 24, 2010

(65) Prior Publication Data

US 2011/0021373 A1    Jan. 27, 2011

Related U.S. Application Data

(63) Continuation of application No. 10/309,419, filed on Dec. 2, 2002, now Pat. No. 7,771,951.

(60) Provisional application No. 60/337,245, filed on Dec. 3, 2001, provisional application No. 60/419,387, filed on Oct. 16, 2002.

(51) Int. Cl.
*G01N 33/53* (2006.01)

(52) U.S. Cl. ............................ 435/7.1; 435/7.2; 436/518

(58) Field of Classification Search ........................ None
See application file for complete search history.

(56) References Cited

U.S. PATENT DOCUMENTS

| | | | |
|---|---|---|---|
| 5,324,633 A | 6/1994 | Fodor et al. |
| 5,426,029 A | 6/1995 | Rittershaus et al. |
| 5,434,076 A | 7/1995 | Freedman et al. |
| 5,514,554 A | 5/1996 | Bacus |
| 5,541,070 A | 7/1996 | Kauvar |
| 5,585,241 A | 12/1996 | Lindmo |
| 5,800,815 A | 9/1998 | Chestnut |
| 5,834,597 A | 11/1998 | Tso et al. |
| 5,929,212 A | 7/1999 | Joliffe et al. |
| 5,939,326 A | 8/1999 | Chupp et al. |
| 5,958,708 A | 9/1999 | Hardman |
| 6,187,310 B1 | 2/2001 | Mann et al. |
| 6,207,160 B1 | 3/2001 | Victoria et al. |
| 6,455,244 B1 | 9/2002 | Guichard et al. |
| 6,492,125 B2 | 12/2002 | Kauvar et al. |
| 6,687,395 B1 | 2/2004 | Deitz et al. |

(Continued)

FOREIGN PATENT DOCUMENTS

WO    WO 93/03770    3/1993

(Continued)

OTHER PUBLICATIONS

Batra et al. "Recombinant anti-erbB2 immunotoxins containing *pseudomonas* exotoxin." *Proc. Natl. Acad. Sci. USA* 89:5867-5871 (1992).

(Continued)

*Primary Examiner* — Jacob Cheu
(74) *Attorney, Agent, or Firm* — Michael G. Penn

(57) ABSTRACT

Methods for categorizing antibodies based on their epitope binding characteristics are described. Methods and systems for determining the epitope recognition properties of different antibodies are provided. Also provided are data analysis processes for clustering antibodies on the basis of their epitope recognition properties and for identifying antibodies having distinct epitope binding characteristics.

52 Claims, 84 Drawing Sheets

U.S. PATENT DOCUMENTS

| | | | |
|---|---|---|---|
| 7,771,951 | B2 | 8/2010 | Walker et al. |
| 2002/0086441 | A1 | 7/2002 | Baranov et al. |
| 2002/0155422 | A1 | 10/2002 | Ingber et al. |
| 2003/0118985 | A1 | 6/2003 | Hunt et al. |
| 2004/0059519 | A1 | 3/2004 | Chandler et al. |

FOREIGN PATENT DOCUMENTS

| | | |
|---|---|---|
| WO | WO 03/048729 | 6/2003 |

OTHER PUBLICATIONS

Carr et al. (Veterinary Immunology and Immunopathology 1994, vol. 43, p. 211-217).

Clynes et al. "Inhibitory Fc receptors modulate in vivo cytoxicity against tumor targets." *Nature Medicine*. 6(4):443-446 (2000).

Eisen et al. "Cluster analysis and display of genome-wide expression patterns." *Proc. Natl. Acad. Sci. USA*. 95:14863-14868 (1998).

Eran et al. *Hepatology*, 32:588-596 (2000).

Jia et al. "A novel method of Multiplexed Competitive Antibody Binning for the characterization of monoclonal antibodies." *Journal of Immunological Methods*. 288(1-2):91-98 (2004).

Kuroki et al. "Determination of epitope 1-52 specificities of a large number of monoclonal antibodies by solid-phase mutual inhibition assays using biotinylated antigen." *Immunological Investigations*. 21(6):523-538 (1992).

Kuroki et al. "A simple solid-phase competition assay with labeled antigen." *Methods in Molecular Biology*. 66:47-53 (1996).

Lange et al. "Epitope mapping of homologous and cross-reactive antigens by monoclonal antibodies to streptococcal cell membrane (mAb to SCM)." *Molecular Immunology*. 33(9):777-786 (1996).

Lindmo et al. "Immunometric assay by flow cytometry using mixtures of two particle types of different affinity." *Journal of Immunological Methods*. 126:183-189 (1990).

O'Hare et al. "A simple method for determining $K_A$s as of both low and high affinity IgG antibodies." *Journal of Immunological Methods*. 218:161-167 (1998).

Park et al. "A latex bead-based flow cytometric immunoassay capable of simultaneous typing of multiple pneumococcal serotypes (multibead assay)." *Clinical and Diagnostic Laboratory Immunology*. 7(3):486-489 (2000).

Perton et al. "Comparison of three methods for competitive binding of monoclonal antibodies—The localization of antigenic sites for monoclonal antibodies on Panulirus interruptus hemocyanin." *Journal of Immunological Methods*. 190(1):117-125 (1996).

Silva et al. Protein Journal 2001 vol. 20, p. 1-7.

Tarassishin et al. "A competitive avidin-biotin ECL dot-blot assay for epitope mapping of monoclonal antibodies." *Journal of Virological Methods*. 49(1):89-92 (1994).

Vignali, D.A.A. "Multiplexed particle-based flow cytometric assays." *Journal of Immunological Methods*. 243(1-2):243-255 (2000).

Watkins et al. "Determination of the relative affinities of antibody fragments expressed in *Escherichia coli* by enzyme-linked immunosorbent assay." *Analytical Biochemistry*. 253:37-45 (1997).

Ziola et al. (Canadian J Microbiology 1994, vol. 45, p. 779-785).

Bins for CR039

| | |
|---|---|
| 1 | 1.11, 1.12 (1.3), 1.16, 1.17 (19), 1.55 (3.8) |
| 2 | 1.29, 1.31, 1.46, 1.65, 2-2-C5, 2-17-4 |
| 3 | 1.23, 1.57, 1.61, 2-28-33 |
| 4 | 2-7-D9 (2.6), 2-20-51 (2.9), 2-21-76 (20.1), 2-34-39 (5.3) |
| 5 | 1.21 (0.9), 2-12-93 (1.5), 2-35-41 (5.1), 2-38-14 (5.2) |
| 6 | 1.1 (1.9), 1.8, 1.30, 1.38, 1.66 |
| 7 | 1.53, 1.59 |
| 8 | 1.3 |
| 9 | 1.13 |
| 10 | 1.24 |
| 11 | 1.32 (11.2) |
| 12 | 1.63 |
| 13 | 2-31-38 |
| 14 | 2-1-A7 |
| 15 | 2-2A-12 |

Notes:
1. Highlighted are FACS positive on 786-0 (CR039+) and negative on M14 (CR039-)
2. Affinity data from BIAcore are included in (nM).

*FIG. 3*

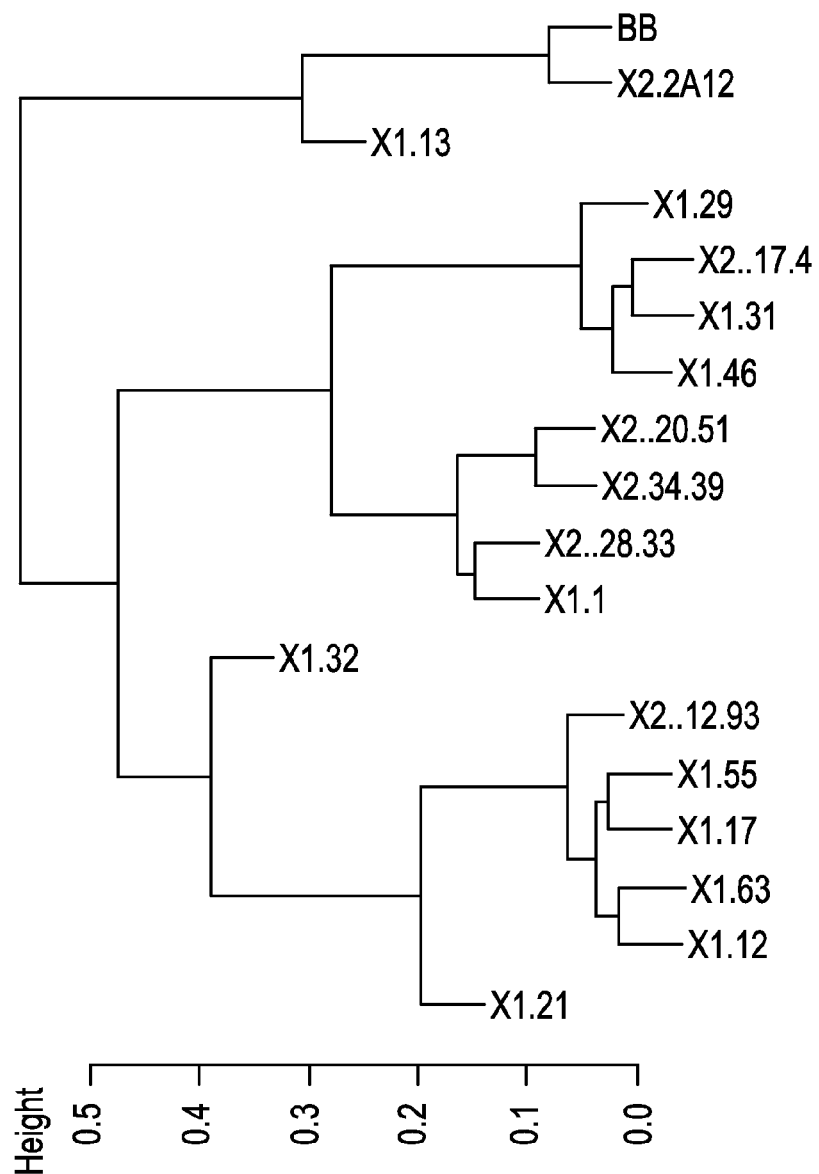

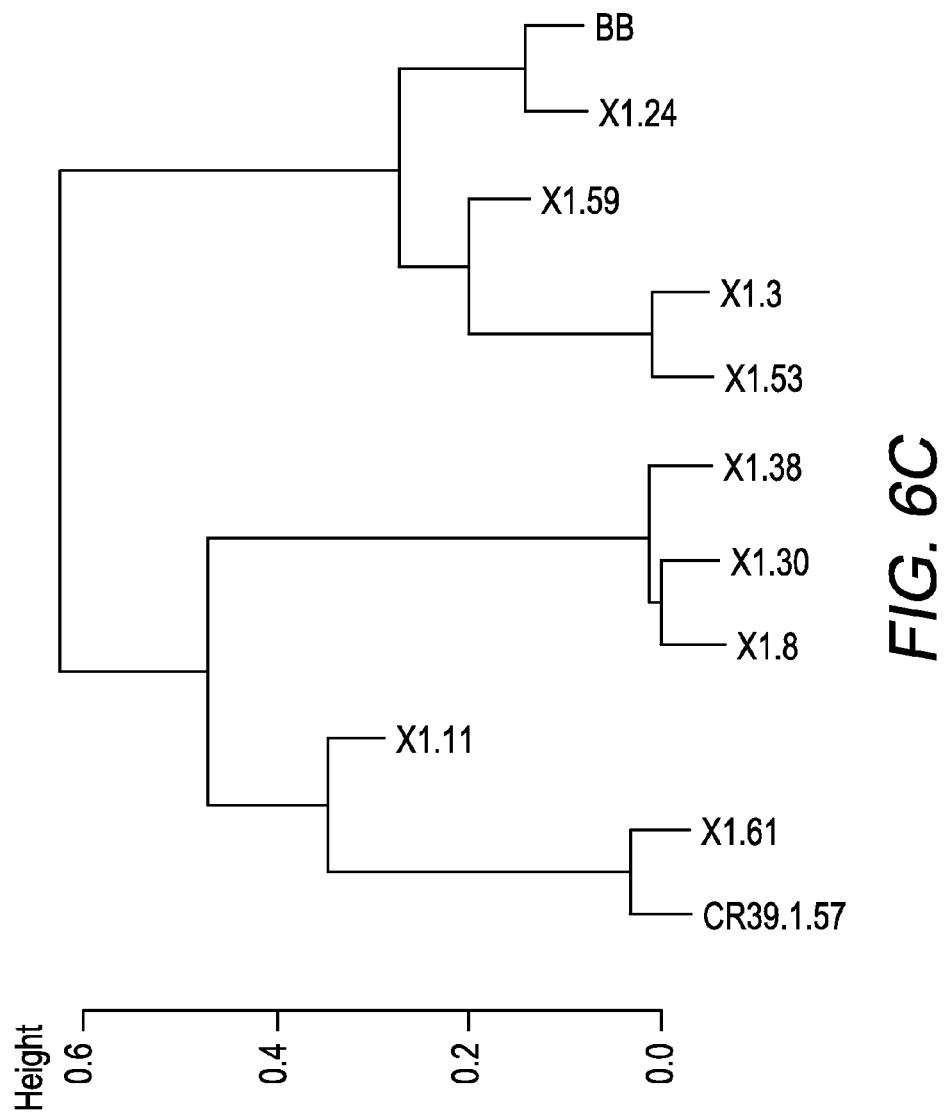

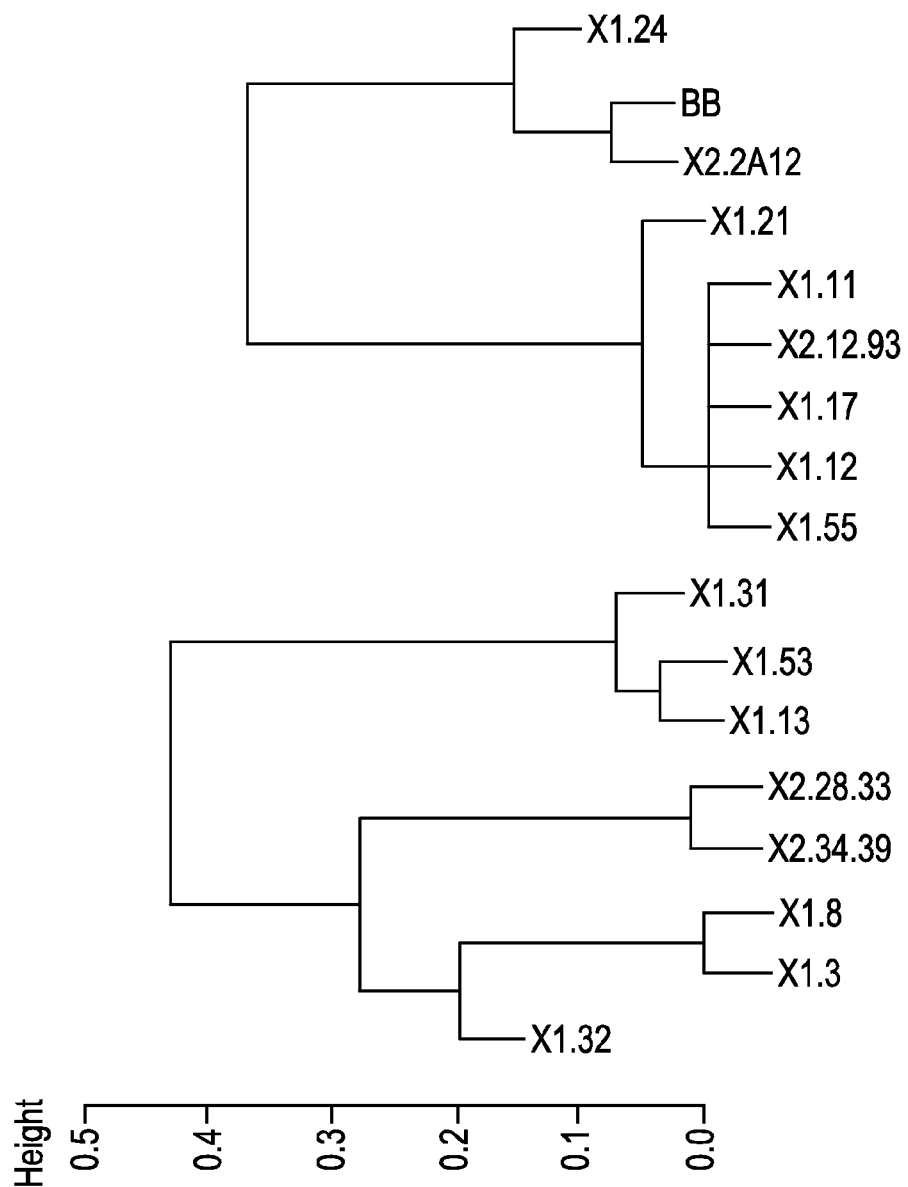

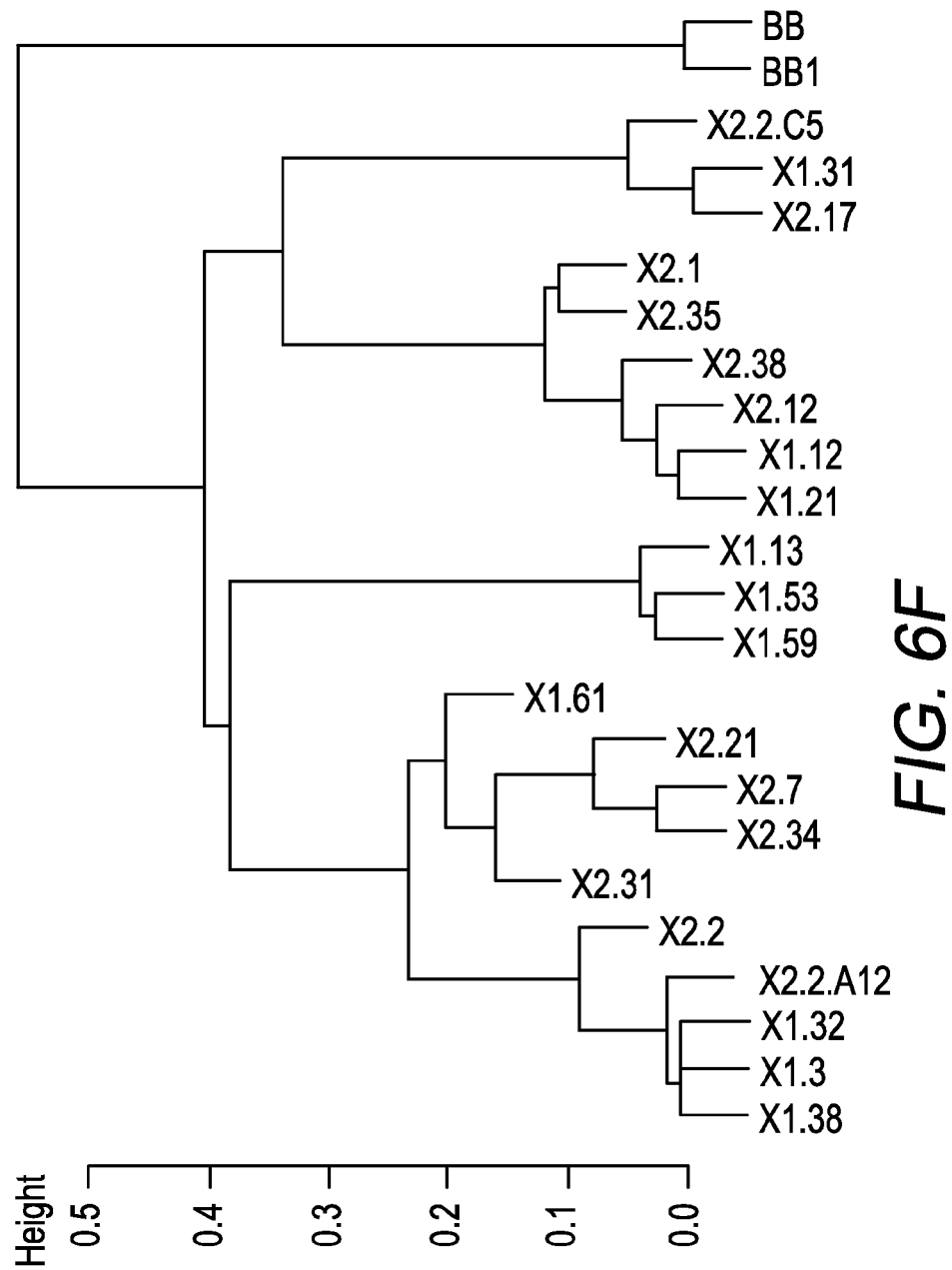

FIG. 8A

Table 1: Input Matrices

A. Intensity matrix for experiment with antigen

| | X2.73 | X2.13 | X2.42 | X2.1 | X2.39 | X2.78 | X2.12 | X2.16 | X2.24 | X2.15 |
|---|---|---|---|---|---|---|---|---|---|---|
| X2.73 | 1002.5 | 3982 | 4131 | 1073 | 3842.5 | 3636 | 4154 | 994 | 3734 | 932 |
| X2.13 | 3704 | 915 | 3430 | 4716.5 | 1265 | 898 | 1159.5 | 5651.5 | 814 | 4482.5 |
| X2.42 | 1904 | 1319 | 3245 | 2612 | 1508 | 1422 | 1851 | 2743 | 948 | 2148.5 |
| X2.1 | 1175 | 2512.5 | 3701 | 959.5 | 3015 | 2217 | 2846.5 | 1169 | 2240 | 1119.5 |
| X2.39 | 3531 | 1370 | 3793 | 5444.5 | 1310 | 1329 | 1595 | 5483 | 1291 | 4349 |
| X2.78 | 3384 | 841 | 3007 | 4170 | 1015 | 821.5 | 1027 | 4965 | 739 | 4023 |
| X2.12 | 3453 | 890.5 | 3281 | 4455.5 | 1187 | 940 | 1111 | 5113 | 814.5 | 4260 |
| X2.16 | 1302 | 4162.5 | 4504 | 1262 | 3884 | 3946.5 | 4557.5 | 1229 | 4094 | 1210 |
| X2.24 | 3999 | 939 | 3770 | 4949.5 | 1237 | 950 | 1161 | 6095.5 | 826 | 4737.5 |
| X2.15 | 1193 | 3989 | 4383 | 1219.5 | 4054.5 | 3899.5 | 4430 | 1120 | 4037 | 1081.5 |
| X2.7 | 3790.5 | 926 | 3568 | 4898 | 1256 | 997 | 1151 | 5692 | 818 | 4505.5 |
| X2.25 | 721 | 1872 | 2094 | 716 | 1878 | 1618 | 2051 | 731 | 1883 | 672 |
| X2.55 | 2501 | 785.5 | 2560 | 3476 | 962.5 | 800 | 996 | 4082 | 706 | 3190 |
| X2.45 | 1193 | 4436 | 4753 | 1181.5 | 4279 | 4126 | 4717 | 1692 | 4389.5 | 1827 |
| X2.69 | 1109 | 3590 | 3890 | 1073 | 3659 | 3194 | 3531.5 | 1058 | 3512 | 1046 |
| X2.31 | 3644 | 979 | 3509.5 | 4754.5 | 1178.5 | 964 | 1165 | 5611 | 802 | 4459.5 |
| X2.56 | 3805.5 | 949.5 | 3455 | 5041.5 | 1290.5 | 948 | 1117 | 6041 | 834 | 4773 |
| X2.76 | 3358.5 | 844 | 3043.5 | 4674 | 1066 | 859 | 1009 | 5305 | 781 | 4205 |
| X2.61 | 3090.5 | 778.5 | 2816 | 4174 | 1006.5 | 789 | 927 | 4518 | 661 | 3864 |
| X2.19 | 828 | 2599 | 2846.5 | 778.5 | 2566 | 2377 | 2734 | 732.5 | 2621 | 665 |
| X2.4 | 895 | 2541.5 | 3108.5 | 867 | 2503 | 2323 | 2947 | 874 | 2548 | 837 |
| BB | 580 | 433 | 542.5 | 494.5 | 365 | 399 | 572 | 586 | 338 | 446 |

| FIG. 8A | FIG. 8B |
|---|---|
| FIG. 8C | FIG. 8D |

| X2.7 | X2.25 | X2.55 | X2.45 | X2.69 | X2.31 | X2.56 | X2.76 | X2.61 | X2.19 | X2.4 | BB |
|---|---|---|---|---|---|---|---|---|---|---|---|
| 8327.5 | 1050 | 5862 | 2056.5 | 959.5 | 4917 | 4799 | 6161 | 4914 | 1357 | 1257.5 | 2638 |
| 1170 | 3620 | 919 | 4537.5 | 10143 | 1026 | 1040.5 | 1106 | 1121 | 7165 | 6467 | 1957 |
| 2430 | 1796 | 1231 | 2732.5 | 4040.5 | 1190 | 1108.5 | 1228 | 1218 | 3530 | 3141 | 1532 |
| 4981.5 | 1104 | 3507 | 2044 | 1190 | 2842 | 2702 | 3729.5 | 2783.5 | 1566.5 | 1361.5 | 1848.5 |
| 1949.5 | 3466 | 1761 | 4454 | 10106 | 1723 | 1677.5 | 1949 | 1723.5 | 6933 | 6760.5 | 2493.5 |
| 1030 | 3257.5 | 894 | 4098 | 9262 | 923 | 978.5 | 1019 | 1020 | 6403 | 5928 | 1786 |
| 1226.5 | 3339 | 1041.5 | 4341 | 9960 | 1071.5 | 1094 | 1193 | 1117.5 | 6457.5 | 6283 | 2116 |
| 8362.5 | 1251.5 | 5926 | 2668 | 1156 | 5074 | 5047 | 6790 | 5360 | 1616.5 | 1550 | 2844 |
| 1084 | 3301 | 975 | 4555.5 | 9507.5 | 1084.5 | 1104 | 1119 | 1161.5 | 6446 | 6339.5 | 1990 |
| 9038 | 1174 | 6175 | 2896 | 1011 | 4997 | 4959 | 6613.5 | 5366 | 1522 | 1442 | 2854 |
| 1109 | 3408 | 1003 | 4558 | 10434 | 1039 | 1070 | 1146 | 1121.5 | 7091.5 | 6504 | 2119 |
| 4129 | 528 | 2874 | 1428 | 621 | 2466.5 | 2357 | 3181 | 2328.5 | 869.5 | 851 | 950 |
| 899 | 2171 | 800 | 3451 | 6021.5 | 902 | 938 | 953.5 | 959 | 4332 | 4320 | 1502 |
| 9622 | 1338 | 6577 | 2881 | 3885 | 5224 | 5291 | 7180.5 | 5668 | 1601 | 2643 | 3482 |
| 7276.5 | 1001 | 5160 | 2380.5 | 1017 | 4190 | 3813 | 5611 | 4265 | 1328 | 1307 | 2459 |
| 1098 | 3006 | 996 | 4354.5 | 8705 | 1075.5 | 1180.5 | 1173.5 | 1097 | 6152 | 6231 | 1963 |
| 964.5 | 3334 | 911 | 4601 | 9378 | 1013 | 1067 | 1042 | 1080 | 6428 | 6351.5 | 1973 |
| 945 | 2841.5 | 885.5 | 3994 | 7527.5 | 962 | 969 | 995 | 994 | 5718 | 5776 | 1580.5 |
| 806 | 2610 | 804.5 | 3794.5 | 7383 | 862.5 | 893 | 927 | 889 | 5174 | 5030 | 1426.5 |
| 5660 | 647.5 | 3941 | 1553 | 603 | 3041 | 3170 | 4080 | 3205.5 | 927.5 | 811 | 1447 |
| 5094 | 818.5 | 3947.5 | 1969 | 771 | 3236 | 3020.5 | 3928 | 3061 | 1066 | 1006.5 | 1752 |
| 587 | 273 | 408 | 1047.5 | 412 | 449.5 | 412.5 | 515 | 471 | 549.5 | 559 | 230.5 |

B. Intensity matrix for experiment without antigen

| | X2.73 | X2.13 | X2.42 | X2.1 | X2.39 | X2.78 | X2.12 | X2.16 | X2.24 | X2.15 |
|---|---|---|---|---|---|---|---|---|---|---|
| X2.73 | 421 | 195 | 184 | 164 | 141 | 233 | 276.5 | 219 | 127 | 202.5 |
| X2.13 | 496 | 282 | 285 | 261.5 | 183.5 | 298 | 398 | 281 | 176 | 268 |
| X2.42 | 416 | 160 | 152 | 141 | 101 | 170.5 | 267.5 | 180 | 102 | 166 |
| X2.1 | 511 | 293 | 276 | 262 | 206 | 288.5 | 394.5 | 300 | 192 | 288 |
| X2.39 | 459 | 217.5 | 220 | 207 | 150 | 230 | 309 | 252 | 150 | 225 |
| X2.78 | 535 | 284 | 276.5 | 250 | 182 | 289 | 395.5 | 286.5 | 177 | 269 |
| X2.12 | 658 | 385 | 394.5 | 368.5 | 274.5 | 402 | 503 | 383.5 | 265 | 369 |
| X2.16 | 549 | 280 | 303 | 293.5 | 212 | 302 | 405 | 326 | 204 | 301.5 |
| X2.24 | 455 | 208 | 198 | 187 | 148 | 213 | 300.5 | 241 | 135.5 | 225 |
| X2.15 | 480 | 229 | 232 | 208 | 152.5 | 237 | 339 | 246 | 151 | 230.5 |
| X2.7 | 494 | 284.5 | 265 | 251 | 178 | 291.5 | 410.5 | 267 | 180 | 272 |
| X2.25 | 299 | 102 | 84.5 | 76 | 57 | 100 | 168 | 124.5 | 57 | 102 |
| X2.55 | 435 | 191.5 | 196 | 165 | 155 | 198.5 | 288 | 226 | 131 | 193 |
| X2.45 | 417 | 163 | 169 | 152.5 | 108 | 168.5 | 256 | 186.5 | 104 | 175 |
| X2.69 | 407.5 | 163 | 152.5 | 141 | 103 | 168 | 257 | 190.5 | 104 | 169 |
| X2.31 | 478 | 224 | 212 | 205.5 | 146.5 | 232.5 | 314 | 256 | 145 | 221 |
| X2.56 | 397.5 | 179 | 174 | 166 | 120 | 182 | 266 | 207 | 114 | 185.5 |
| X2.76 | 461 | 220 | 217 | 237.5 | 159 | 232 | 317.5 | 267 | 169.5 | 232 |
| X2.61 | 391 | 166 | 164 | 159 | 109 | 172 | 243 | 194 | 113 | 177 |
| X2.19 | 378 | 138 | 127 | 112 | 79 | 135 | 214.5 | 163 | 82 | 135 |
| X2.4 | 325 | 127 | 117 | 120 | 77.5 | 121.5 | 199 | 160 | 76 | 141 |
| BB | 311 | 94.5 | 80.5 | 72 | 51.5 | 95 | 163.5 | 115 | 49.5 | 92 |

*FIG. 8C*

| X2.7 | X2.25 | X2.55 | X2.45 | X2.69 | X2.31 | X2.56 | X2.76 | X2.61 | X2.19 | X2.4 | BB |
|---|---|---|---|---|---|---|---|---|---|---|---|
| 443.5 | 187 | 198.5 | 191 | 282 | 165.5 | 154 | 227 | 207 | 252 | 244 | 497 |
| 512 | 196 | 247 | 251.5 | 300 | 229 | 193 | 273 | 247 | 323 | 308.5 | 432 |
| 311.5 | 88 | 163 | 149 | 177 | 142 | 124 | 180.5 | 168 | 195 | 198.5 | 186.5 |
| 463 | 221 | 276.5 | 275.5 | 324 | 236 | 198.5 | 281 | 275 | 348 | 315.5 | 418 |
| 399.5 | 170 | 300.5 | 231 | 266.5 | 191 | 168 | 244 | 209 | 279 | 267 | 364 |
| 529 | 200 | 247 | 250 | 318.5 | 231 | 187 | 286 | 251 | 336 | 301 | 475 |
| 668.5 | 315.5 | 374.5 | 391 | 452.5 | 322 | 268 | 379 | 348 | 472.5 | 421 | 671 |
| 482 | 232 | 288.5 | 309 | 324.5 | 259 | 224.5 | 316 | 283 | 382 | 360 | 481 |
| 368 | 140 | 190 | 208.5 | 241.5 | 164 | 145 | 207.5 | 188.5 | 259 | 247 | 266 |
| 420 | 162 | 223 | 233 | 293 | 201 | 179 | 257 | 240 | 309 | 291 | 368.5 |
| 611 | 195 | 247 | 240 | 300 | 228.5 | 190 | 282 | 241.5 | 331 | 296 | 493.5 |
| 185 | 37 | 83 | 75 | 102 | 87 | 70 | 117 | 110.5 | 108 | 131 | 73 |
| 338 | 126.5 | 178.5 | 181.5 | 211 | 169 | 142 | 204.5 | 195.5 | 229 | 221 | 262 |
| 339 | 103 | 154 | 154 | 206 | 140 | 122.5 | 194.5 | 172.5 | 212 | 214 | 241 |
| 299 | 95 | 155 | 152 | 166 | 144 | 124 | 183 | 174 | 199.5 | 202 | 195 |
| 379 | 148.5 | 207.5 | 210 | 236 | 176 | 155 | 220 | 205.5 | 263 | 249 | 269 |
| 330 | 124 | 164.5 | 185 | 207 | 150 | 135.5 | 199 | 181 | 218 | 225 | 239 |
| 347.5 | 168 | 206.5 | 216 | 213 | 183 | 160 | 214 | 204.5 | 241 | 246.5 | 233.5 |
| 296 | 106.5 | 156 | 153 | 181 | 147 | 119.5 | 171.5 | 167.5 | 201.5 | 195 | 181 |
| 263 | 70 | 116 | 121 | 153 | 116.5 | 98 | 152 | 144.5 | 162 | 170 | 146 |
| 235.5 | 70 | 118 | 119 | 138 | 114 | 96 | 148 | 139 | 149 | 166 | 141 |
| 186 | 31 | 78 | 69 | 90 | 83 | 67 | 107 | 103.5 | 89 | 116 | 63 |

Table 2: Difference between matrices for experiments with and without antigen

|  | X2.73 | X2.13 | X2.42 | X2.1 | X2.39 | X2.78 | X2.12 | X2.16 | X2.24 | X2.15 |
|---|---|---|---|---|---|---|---|---|---|---|
| X2.73 | 581.5 | 3787 | 3947 | 909 | 3701.5 | 3403 | 3877.5 | 775 | 3607 | 729.5 |
| X2.13 | 3208 | 633 | 3145 | 4455 | 1081.5 | 600 | 761.5 | 5370.5 | 638 | 4214.5 |
| X2.42 | 1488 | 1159 | 3093 | 2471 | 1407 | 1251.5 | 1583.5 | 2563 | 846 | 1982.5 |
| X2.1 | 664 | 2219.5 | 3425 | 697.5 | 2809 | 1928.5 | 2452 | 869 | 2048 | 831.5 |
| X2.39 | 3072 | 1152.5 | 3573 | 5237.5 | 1160 | 1099 | 1286 | 5231 | 1141 | 4124 |
| X2.78 | 2849 | 557 | 2730.5 | 3920 | 833 | 532.5 | 631.5 | 4678.5 | 562 | 3754 |
| X2.12 | 2795 | 505.5 | 2886.5 | 4087 | 912.5 | 538 | 608 | 4729.5 | 549.5 | 3891 |
| X2.16 | 753 | 3882.5 | 4201 | 968.5 | 3672 | 3644.5 | 4152.5 | 903 | 3890 | 908.5 |
| X2.24 | 3544 | 731 | 3572 | 4762.5 | 1089 | 737 | 860.5 | 5854.5 | 690.5 | 4512.5 |
| X2.15 | 713 | 3760 | 4151 | 1011.5 | 3902 | 3662.5 | 4091 | 874 | 3886 | 851 |
| X2.7 | 3296.5 | 641.5 | 3303 | 4647 | 1078 | 705.5 | 740.5 | 5425 | 638 | 4233.5 |
| X2.25 | 422 | 1770 | 2009.5 | 640 | 1821 | 1518 | 1883 | 606.5 | 1826 | 570 |
| X2.55 | 2066 | 594 | 2364 | 3311 | 807.5 | 601.5 | 708 | 3856 | 575 | 2997 |
| X2.45 | 776 | 4273 | 4584 | 1029 | 4171 | 3957.5 | 4461 | 1505.5 | 4285.5 | 1652 |
| X2.69 | 701.5 | 3427 | 3737.5 | 932 | 3556 | 3026 | 3274.5 | 867.5 | 3408 | 877 |
| X2.31 | 3166 | 755 | 3297.5 | 4549 | 1032 | 731.5 | 851 | 5355 | 657 | 4238.5 |
| X2.56 | 3408 | 770.5 | 3281 | 4875.5 | 1170.5 | 766 | 851 | 5834 | 720 | 4587.5 |
| X2.76 | 2897.5 | 624 | 2826.5 | 4436.5 | 907 | 627 | 691.5 | 5038 | 611.5 | 3973 |
| X2.61 | 2699.5 | 612.5 | 2652 | 4015 | 897.5 | 617 | 684 | 4324 | 548 | 3687 |
| X2.19 | 450 | 2461 | 2719.5 | 666.5 | 2487 | 2242 | 2519.5 | 569.5 | 2539 | 530 |
| X2.4 | 570 | 2414.5 | 2991.5 | 747 | 2425.5 | 2201.5 | 2748 | 714 | 2472 | 696 |
| BB | 269 | 338.5 | 462 | 422.5 | 313.5 | 304 | 408.5 | 471 | 288.5 | 354 |

| FIG. 9A | FIG. 9B |
|---|---|

| X2.7 | X2.25 | X2.55 | X2.45 | X2.69 | X2.31 | X2.56 | X2.76 | X2.61 | X2.19 | X2.4 | BB |
|---|---|---|---|---|---|---|---|---|---|---|---|
| 7884 | 863 | 5663.5 | 1865.5 | 677.5 | 4751.5 | 4645 | 5934 | 4707 | 1105 | 1013.5 | 2141 |
| 658 | 3424 | 672 | 4286 | 9843 | 797 | 847.5 | 833 | 874 | 6842 | 6158.5 | 1525 |
| 2118.5 | 1708 | 1068 | 2583.5 | 3863.5 | 1048 | 984.5 | 1047.5 | 1050 | 3335 | 2942.5 | 1345.5 |
| 4518.5 | 883 | 3230.5 | 1768.5 | 866 | 2606 | 2503.5 | 3448.5 | 2508.5 | 1218.5 | 1046 | 1430.5 |
| 1550 | 3296 | 1460.5 | 4223 | 9839.5 | 1532 | 1509.5 | 1705 | 1514.5 | 6654 | 6493.5 | 2129.5 |
| 501 | 3057.5 | 647 | 3848 | 8943.5 | 692 | 791.5 | 733 | 769 | 6067 | 5627 | 1311 |
| 558 | 3023.5 | 667 | 3950 | 9507.5 | 749.5 | 826 | 814 | 769.5 | 5985 | 5862 | 1445 |
| 7880.5 | 1019.5 | 5637.5 | 2359 | 831.5 | 4815 | 4822.5 | 6474 | 5077 | 1234.5 | 1190 | 2363 |
| 716 | 3161 | 785 | 4347 | 9266 | 920.5 | 959 | 911.5 | 973 | 6187 | 6092.5 | 1724 |
| 8618 | 1012 | 5952 | 2663 | 718 | 4796 | 4780 | 6356.5 | 5126 | 1213 | 1151 | 2485.5 |
| 498 | 3213 | 756 | 4318 | 10134 | 810.5 | 880 | 864 | 880 | 6760.5 | 6208 | 1625.5 |
| 3944 | 491 | 2791 | 1353 | 519 | 2379.5 | 2287 | 3064 | 2218 | 761.5 | 720 | 877 |
| 561 | 2044.5 | 621.5 | 3269.5 | 5810.5 | 733 | 796 | 749 | 763.5 | 4103 | 4099 | 1240 |
| 9283 | 1235 | 6423 | 2727 | 3679 | 5084 | 5168.5 | 6986 | 5495.5 | 1389 | 2429 | 3241 |
| 6977.5 | 906 | 5005 | 2228.5 | 851 | 4046 | 3689 | 5428 | 4091 | 1128.5 | 1105 | 2264 |
| 719 | 2857.5 | 788.5 | 4144.5 | 8469 | 899.5 | 1025.5 | 953.5 | 891.5 | 5889 | 5982 | 1694 |
| 634.5 | 3210 | 746.5 | 4416 | 9171 | 863 | 931.5 | 843 | 899 | 6210 | 6126.5 | 1734 |
| 597.5 | 2673.5 | 679 | 3778 | 7314.5 | 779 | 809 | 781 | 789.5 | 5477 | 5529.5 | 1347 |
| 510 | 2503.5 | 648.5 | 3641.5 | 7202 | 715.5 | 773.5 | 755.5 | 721.5 | 4972.5 | 4835 | 1245.5 |
| 5397 | 577.5 | 3825 | 1432 | 450 | 2924.5 | 3072 | 3928 | 3061 | 765.5 | 641 | 1301 |
| 4858.5 | 748.5 | 3829.5 | 1850 | 633 | 3122 | 2924.5 | 3780 | 2922 | 917 | 840.5 | 1611 |
| 401 | 242 | 330 | 978.5 | 322 | 366.5 | 345.5 | 408 | 367.5 | 460.5 | 443 | 167.5 |

FIG. 10A

Table 3: Difference matrix where values below a minimum threshold are set to the threshold of 200

|       | X2.73  | X2.13  | X2.42  | X2.1   | X2.39  | X2.78  | X2.12  | X2.16  | X2.24  | X2.15  |
|-------|--------|--------|--------|--------|--------|--------|--------|--------|--------|--------|
| X2.73 | 581.5  | 3787   | 3947   | 909    | 3701.5 | 3403   | 3877.5 | 775    | 3607   | 729.5  |
| X2.13 | 3208   | 633    | 3145   | 4455   | 1081.5 | 600    | 761.5  | 5370.5 | 638    | 4214.5 |
| X2.42 | 1488   | 1159   | 3093   | 2471   | 1407   | 1251.5 | 1583.5 | 2563   | 846    | 1982.5 |
| X2.1  | 664    | 2219.5 | 3425   | 697.5  | 2809   | 1928.5 | 2452   | 869    | 2048   | 831.5  |
| X2.39 | 3072   | 1152.5 | 3573   | 5237.5 | 1160   | 1099   | 1286   | 5231   | 1141   | 4124   |
| X2.78 | 2849   | 557    | 2730.5 | 3920   | 833    | 532.5  | 631.5  | 4678.5 | 562    | 3754   |
| X2.12 | 2795   | 505.5  | 2886.5 | 4087   | 912.5  | 538    | 608    | 4729.5 | 549.5  | 3891   |
| X2.16 | 753    | 3882.5 | 4201   | 968.5  | 3672   | 3644.5 | 4152.5 | 903    | 3890   | 908.5  |
| X2.24 | 3544   | 731    | 3572   | 4762.5 | 1089   | 737    | 860.5  | 5854.5 | 690.5  | 4512.5 |
| X2.15 | 713    | 3760   | 4151   | 1011.5 | 3902   | 3662.5 | 4091   | 874    | 3886   | 851    |
| X2.7  | 3296.5 | 641.5  | 3303   | 4647   | 1078   | 705.5  | 740.5  | 5425   | 638    | 4233.5 |
| X2.25 | 422    | 1770   | 2009.5 | 640    | 1821   | 1518   | 1883   | 606.5  | 1826   | 570    |
| X2.55 | 2066   | 594    | 2364   | 3311   | 807.5  | 601.5  | 708    | 3856   | 575    | 2997   |
| X2.45 | 776    | 4273   | 4584   | 1029   | 4171   | 3957.5 | 4461   | 1505.5 | 4285.5 | 1652   |
| X2.69 | 701.5  | 3427   | 3737.5 | 932    | 3556   | 3026   | 3274.5 | 867.5  | 3408   | 877    |
| X2.31 | 3166   | 755    | 3297.5 | 4549   | 1032   | 731.5  | 851    | 5355   | 657    | 4238.5 |
| X2.56 | 3408   | 770.5  | 3281   | 4875.5 | 1170.5 | 766    | 851    | 5834   | 720    | 4587.5 |
| X2.76 | 2897.5 | 624    | 2826.5 | 4436.5 | 907    | 627    | 691.5  | 5038   | 611.5  | 3973   |
| X2.61 | 2699.5 | 612.5  | 2652   | 4015   | 897.5  | 617    | 684    | 4324   | 548    | 3687   |
| X2.19 | 450    | 2461   | 2719.5 | 666.5  | 2487   | 2242   | 2519.5 | 569.5  | 2539   | 530    |
| X2.4  | 570    | 2414.5 | 2991.5 | 747    | 2425.5 | 2201.5 | 2748   | 714    | 2472   | 696    |
| BB    | 269    | 338.5  | 462    | 422.5  | 313.5  | 304    | 408.5  | 471    | 288.5  | 354    |

| X2.7 | X2.25 | X2.55 | X2.45 | X2.69 | X2.31 | X2.56 | X2.76 | X2.61 | X2.19 | X2.4 | BB |
|---|---|---|---|---|---|---|---|---|---|---|---|
| 7884 | 863 | 5663.5 | 1865.5 | 677.5 | 4751.5 | 4645 | 5934 | 4707 | 1105 | 1013.5 | 2141 |
| 658 | 3424 | 672 | 4286 | 9843 | 797 | 847.5 | 833 | 874 | 6842 | 6158.5 | 1525 |
| 2118.5 | 1708 | 1068 | 2583.5 | 3863.5 | 1048 | 984.5 | 1047.5 | 1050 | 3335 | 2942.5 | 1345.5 |
| 4518.5 | 883 | 3230.5 | 1768.5 | 866 | 2606 | 2503.5 | 3448.5 | 2508.5 | 1218.5 | 1046 | 1430.5 |
| 1550 | 3296 | 1460.5 | 4223 | 9839.5 | 1532 | 1509.5 | 1705 | 1514.5 | 6654 | 6493.5 | 2129.5 |
| 501 | 3057.5 | 647 | 3848 | 8943.5 | 692 | 791.5 | 733 | 769 | 6067 | 5627 | 1311 |
| 558 | 3023.5 | 667 | 3950 | 9507.5 | 749.5 | 826 | 814 | 769.5 | 5985 | 5862 | 1445 |
| 7880.5 | 1019.5 | 5637.5 | 2359 | 831.5 | 4815 | 4822.5 | 6474 | 5077 | 1234.5 | 1190 | 2363 |
| 716 | 3161 | 785 | 4347 | 9266 | 920.5 | 959 | 911.5 | 973 | 6187 | 6092.5 | 1724 |
| 8618 | 1012 | 5952 | 2663 | 718 | 4796 | 4780 | 6356.5 | 5126 | 1213 | 1151 | 2485.5 |
| 498 | 3213 | 756 | 4318 | 10133.5 | 810.5 | 880 | 864 | 880 | 6760.5 | 6208 | 1625.5 |
| 3944 | 491 | 2791 | 1353 | 519 | 2379.5 | 2287 | 3064 | 2218 | 761.5 | 720 | 877 |
| 561 | 2044.5 | 621.5 | 3269.5 | 5810.5 | 733 | 796 | 749 | 763.5 | 4103 | 4099 | 1240 |
| 9283 | 1235 | 6423 | 2727 | 3679 | 5084 | 5168.5 | 6986 | 5495.5 | 1389 | 2429 | 3241 |
| 6977.5 | 906 | 5005 | 2228.5 | 851 | 4046 | 3689 | 5428 | 4091 | 1128.5 | 1105 | 2264 |
| 719 | 2857.5 | 788.5 | 4144.5 | 8469 | 899.5 | 1025.5 | 953.5 | 891.5 | 5889 | 5982 | 1694 |
| 634.5 | 3210 | 746.5 | 4416 | 9171 | 863 | 931.5 | 843 | 899 | 6210 | 6126.5 | 1734 |
| 597.5 | 2673.5 | 679 | 3778 | 7314.5 | 779 | 809 | 781 | 789.5 | 5477 | 5529.5 | 1347 |
| 510 | 2503.5 | 648.5 | 3641.5 | 7202 | 715.5 | 773.5 | 755.5 | 721.5 | 4972.5 | 4835 | 1245.5 |
| 5397 | 577.5 | 3825 | 1432 | 450 | 2924.5 | 3072 | 3928 | 3061 | 765.5 | 641 | 1301 |
| 4858.5 | 748.5 | 3829.5 | 1850 | 633 | 3122 | 2924.5 | 3780 | 2922 | 917 | 840.5 | 1611 |
| 401 | 242 | 330 | 978.5 | 322 | 366.5 | 345.5 | 408 | 367.5 | 460.5 | 443 | 200 |

Table 4: Row normalized matrix

|       | X2.73    | X2.13    | X2.42    | X2.1     | X2.39    | X2.78    |
|-------|----------|----------|----------|----------|----------|----------|
| X2.73 | 0.271602 | 1.7687996| 1.843531 | 0.424568 | 1.728865 | 1.589444 |
| X2.13 | 2.103607 | 0.415082 | 2.062295 | 2.921312 | 0.70918  | 0.393443 |
| X2.42 | 1.105909 | 0.8613898| 2.298774 | 1.836492 | 1.045708 | 0.930138 |
| X2.1  | 0.464173 | 1.5515554| 2.394268 | 0.487592 | 1.963649 | 1.34813  |
| X2.39 | 1.442592 | 0.5412069| 1.677859 | 2.459498 | 0.544729 | 0.516084 |
| X2.78 | 2.17315  | 0.4248665| 2.082761 | 2.990084 | 0.635393 | 0.406179 |
| X2.12 | 1.934256 | 0.349827 | 1.997578 | 2.828374 | 0.631488 | 0.372318 |
| X2.16 | 0.318663 | 1.6430385| 1.777825 | 0.40986  | 1.553957 | 1.542319 |
| X2.24 | 2.055685 | 0.4240139| 2.071926 | 2.762471 | 0.631671 | 0.427494 |
| X2.15 | 0.286864 | 1.5127741| 1.670087 | 0.40696  | 1.569906 | 1.473547 |
| X2.7  | 2.027991 | 0.3946478| 2.03199  | 2.858813 | 0.663181 | 0.43402  |
| X2.25 | 0.481186 | 2.018244 | 2.291334 | 0.729761 | 2.076397 | 1.730901 |
| X2.55 | 1.666129 | 0.4790323| 1.906452 | 2.670161 | 0.65121  | 0.485081 |
| X2.45 | 0.239432 | 1.3184202| 1.414378 | 0.317495 | 1.286949 | 1.221074 |
| X2.69 | 0.30985  | 1.5136926| 1.650839 | 0.411661 | 1.570671 | 1.336572 |
| X2.31 | 1.868949 | 0.4456907| 1.946576 | 2.685536 | 0.609209 | 0.431818 |
| X2.56 | 1.965398 | 0.4443483| 1.892157 | 2.811707 | 0.675029 | 0.441753 |
| X2.76 | 2.151077 | 0.4632517| 2.098367 | 3.293615 | 0.673348 | 0.465479 |
| X2.61 | 2.167403 | 0.4917704| 2.129265 | 3.223605 | 0.720594 | 0.495383 |
| X2.19 | 0.345888 | 1.8916218| 2.090315 | 0.512298 | 1.911607 | 1.72329  |
| X2.4  | 0.353818 | 1.4987585| 1.856921 | 0.463687 | 1.505587 | 1.366543 |
| BB    | 1.345    | 1.6925   | 2.31     | 2.1125   | 1.5675   | 1.52     |

*FIG. 11A*

| FIG. 11A | FIG. 11B | FIG. 11C |

| X2.12 | X2.16 | X2.24 | X2.15 | X2.7 | X2.25 | X2.55 | X2.45 |
|---|---|---|---|---|---|---|---|
| 1.81107 | 0.36198 | 1.684727 | 0.340729 | 3.682391 | 0.403083 | 2.645259 | 0.871322 |
| 0.499344 | 3.521639 | 0.418361 | 2.763607 | 0.431475 | 2.245246 | 0.440656 | 2.810492 |
| 1.176886 | 1.904868 | 0.628763 | 1.47343 | 1.574508 | 1.269417 | 0.793757 | 1.920104 |
| 1.714086 | 0.60748 | 1.431667 | 0.581265 | 3.158686 | 0.617267 | 2.258301 | 1.236281 |
| 0.603898 | 2.456445 | 0.535807 | 1.936605 | 0.72787 | 1.547781 | 0.685842 | 1.983095 |
| 0.481693 | 3.56865 | 0.42868 | 2.863463 | 0.382151 | 2.332189 | 0.493516 | 2.935164 |
| 0.420761 | 3.27301 | 0.380277 | 2.692734 | 0.386159 | 2.092388 | 0.461592 | 2.733564 |
| 1.7573 | 0.382141 | 1.646212 | 0.384469 | 3.334956 | 0.431443 | 2.385739 | 0.998307 |
| 0.49913 | 3.395882 | 0.400522 | 2.617459 | 0.415313 | 1.833527 | 0.455336 | 2.521462 |
| 1.645947 | 0.35164 | 1.563468 | 0.342386 | 3.46731 | 0.407162 | 2.394689 | 1.071414 |
| 0.455552 | 3.337435 | 0.392495 | 2.604429 | 0.306367 | 1.976623 | 0.465088 | 2.656413 |
| 2.147092 | 0.691562 | 2.082098 | 0.649943 | 4.497149 | 0.559863 | 3.18244 | 1.542759 |
| 0.570968 | 3.109677 | 0.46371 | 2.416936 | 0.452419 | 1.64879 | 0.50121 | 2.636694 |
| 1.376427 | 0.464517 | 1.322277 | 0.509719 | 2.864239 | 0.381055 | 1.981796 | 0.841407 |
| 1.446334 | 0.383171 | 1.5053 | 0.387368 | 3.081935 | 0.400177 | 2.210689 | 0.98432 |
| 0.502361 | 3.161157 | 0.387839 | 2.502066 | 0.424439 | 1.686836 | 0.465466 | 2.446576 |
| 0.490773 | 3.364475 | 0.415225 | 2.645617 | 0.365917 | 1.851211 | 0.430508 | 2.546713 |
| 0.513363 | 3.740163 | 0.453972 | 2.949517 | 0.443578 | 1.984781 | 0.504083 | 2.804751 |
| 0.549177 | 3.471698 | 0.439984 | 2.960257 | 0.409474 | 2.010036 | 0.520674 | 2.923725 |
| 1.936587 | 0.43774 | 1.951576 | 0.407379 | 4.148347 | 0.443889 | 2.940046 | 1.100692 |
| 1.705773 | 0.443203 | 1.534451 | 0.43203 | 3.015829 | 0.464618 | 2.377095 | 1.148355 |
| 2.0425 | 2.355 | 1.4425 | 1.77 | 2.005 | 1.21 | 1.65 | 4.8925 |

FIG. 11C

| X2.69 | X2.31 | X2.56 | X2.76 | X2.61 | X2.19 | X2.4 | BB |
|---|---|---|---|---|---|---|---|
| 0.316441 | 2.21929 | 2.169547 | 2.771602 | 2.198505 | 0.516114 | 0.473377 | 1 |
| 6.454426 | 0.522623 | 0.555738 | 0.54623 | 0.573115 | 4.486557 | 4.038361 | 1 |
| 2.871423 | 0.778893 | 0.731698 | 0.778521 | 0.780379 | 2.478633 | 2.186919 | 1 |
| 0.605383 | 1.821741 | 1.750087 | 2.410696 | 1.753583 | 0.8518 | 0.731213 | 1 |
| 4.620568 | 0.719418 | 0.708852 | 0.800657 | 0.7112 | 3.124677 | 3.049307 | 1 |
| 6.821892 | 0.527841 | 0.603738 | 0.559115 | 0.586575 | 4.627765 | 4.292143 | 1 |
| 6.579585 | 0.518685 | 0.571626 | 0.563322 | 0.532526 | 4.141869 | 4.056747 | 1 |
| 0.351883 | 2.037664 | 2.040838 | 2.739738 | 2.14854 | 0.522429 | 0.503597 | 1 |
| 5.37471 | 0.533933 | 0.556265 | 0.528712 | 0.564385 | 3.588747 | 3.533933 | 1 |
| 0.288876 | 1.929592 | 1.923154 | 2.557433 | 2.062362 | 0.488031 | 0.463086 | 1 |
| 6.234082 | 0.498616 | 0.541372 | 0.531529 | 0.541372 | 4.159028 | 3.819133 | 1 |
| 0.59179 | 2.713227 | 2.607754 | 3.493729 | 2.529076 | 0.868301 | 0.820981 | 1 |
| 4.685887 | 0.591129 | 0.641936 | 0.604032 | 0.615726 | 3.308871 | 3.305645 | 1 |
| 1.135144 | 1.568652 | 1.594724 | 2.155508 | 1.695619 | 0.428571 | 0.74946 | 1 |
| 0.375883 | 1.787103 | 1.629417 | 2.397527 | 1.806979 | 0.498454 | 0.488074 | 1 |
| 4.99941 | 0.530992 | 0.605372 | 0.562869 | 0.526269 | 3.476387 | 3.531287 | 1 |
| 5.288927 | 0.497693 | 0.537197 | 0.486159 | 0.518454 | 3.581315 | 3.53316 | 1 |
| 5.430215 | 0.578322 | 0.600594 | 0.579807 | 0.586117 | 4.066073 | 4.105048 | 1 |
| 5.782417 | 0.574468 | 0.621036 | 0.606584 | 0.579285 | 3.992373 | 3.881975 | 1 |
| 0.345888 | 2.247886 | 2.361261 | 3.019216 | 2.352806 | 0.588394 | 0.492698 | 1 |
| 0.392924 | 1.937927 | 1.815332 | 2.346369 | 1.81378 | 0.569212 | 0.521726 | 1 |
| 1.61 | 1.8325 | 1.7275 | 2.04 | 1.8375 | 2.3025 | 2.215 | 1 |

*FIG. 12A*

Table 5: Diagonal normalized matrix

|        | X2.73     | X2.13     | X2.42    | X2.1      | X2.39    | X2.78     |
|--------|-----------|-----------|----------|-----------|----------|-----------|
| X2.73  | 1         | 4         | 1.843531 | 0.8707448 | 3.173809 | 3.9131668 |
| X2.13  | 4         | 1         | 2.062295 | 4         | 1.301896 | 0.9686447 |
| X2.42  | 4         | 2.0752282 | 2.298774 | 3.7664542 | 1.919685 | 2.2899723 |
| X2.1   | 1.7090201 | 3.7379494 | 2.394268 | 1         | 3.60482  | 3.3190581 |
| X2.39  | 4         | 1.3038554 | 1.677859 | 4         | 1        | 1.2705833 |
| X2.78  | 4         | 1.0235726 | 2.082761 | 4         | 1.166439 | 1         |
| X2.12  | 4         | 0.8427901 | 1.997578 | 4         | 1.15927  | 0.91666373 |
| X2.16  | 1.1732706 | 3.9583471 | 1.777825 | 0.840581  | 2.852716 | 3.7971461 |
| X2.24  | 4         | 1.0215185 | 2.071926 | 4         | 1.159606 | 1.0524787 |
| X2.15  | 1.0561916 | 3.6445189 | 1.670087 | 0.8346334 | 2.881995 | 3.6278301 |
| X2.7   | 4         | 0.9507708 | 2.03199  | 4         | 1.217451 | 1.0685458 |
| X2.25  | 1.7716577 | 4         | 2.291334 | 1.496663  | 3.811799 | 4         |
| X2.55  | 4         | 1.1540667 | 1.906452 | 4         | 1.195475 | 1.1942549 |
| X2.45  | 0.8815555 | 3.1762889 | 1.414378 | 0.6511484 | 2.362549 | 3.0062492 |
| X2.69  | 1.1408228 | 3.6467317 | 1.650839 | 0.8442735 | 2.883401 | 3.2906037 |
| X2.31  | 4         | 1.0737414 | 1.946576 | 4         | 1.118371 | 1.0631242 |
| X2.56  | 4         | 1.0705074 | 1.892157 | 4         | 1.239202 | 1.0875839 |
| X2.76  | 4         | 1.1160487 | 2.098367 | 4         | 1.236116 | 1.1459958 |
| X2.61  | 4         | 1.1847548 | 2.129265 | 4         | 1.322849 | 1.2196199 |
| X2.19  | 1.2735094 | 4         | 2.090315 | 1.0506704 | 3.509281 | 4         |
| X2.4   | 1.3027056 | 3.6107532 | 1.856921 | 0.9509741 | 2.76392  | 3.3643892 |
| BB     | 4         | 4         | 2.31     | 4         | 2.877579 | 3.7421972 |

| FIG. 12A | FIG. 12B | FIG. 12C |

| X2.12 | X2.16 | X2.24 | X2.15 | X2.7 | X2.25 | X2.55 | X2.45 |
|---|---|---|---|---|---|---|---|
| 4 | 0.9472421 | 4 | 0.9951598 | 4 | 0.7199664 | 4 | 1.035553 |
| 1.186764 | 4 | 1.0445384 | 4 | 1.40836 | 4 | 0.8791844 | 3.340229 |
| 2.79704 | 4 | 1.5698575 | 4 | 4 | 2.2673693 | 1.5836824 | 2.282016 |
| 4 | 1.5896733 | 3.574503 | 1.6976908 | 4 | 1.1025313 | 4 | 1.469302 |
| 1.43525 | 4 | 1.3377704 | 4 | 2.37581 | 2.7645704 | 1.3683729 | 2.356879 |
| 1.144814 | 4 | 1.0703041 | 4 | 1.247362 | 4 | 0.9846506 | 3.4884 |
| 1 | 4 | 0.9494529 | 4 | 1.260445 | 3.7373195 | 0.9209553 | 3.248801 |
| 4 | 1 | 4 | 1.1229112 | 4 | 0.7706224 | 4 | 1.186474 |
| 1.186255 | 4 | 1 | 4 | 1.355606 | 3.274955 | 0.9084749 | 2.996721 |
| 3.91183 | 0.9201818 | 3.9035757 | 1 | 4 | 0.7272519 | 4 | 1.27336 |
| 1.082686 | 4 | 0.9799576 | 4 | 1 | 3.5305458 | 0.9279303 | 3.157109 |
| 4 | 1.8097025 | 4 | 1.8982765 | 4 | 1 | 4 | 1.833547 |
| 1.356987 | 4 | 1.1577632 | 4 | 1.476722 | 2.944988 | 1 | 3.133672 |
| 3.271278 | 1.2155636 | 3.301384 | 1.4887275 | 4 | 0.6806221 | 3.9540253 | 1 |
| 3.437422 | 1.0026954 | 3.7583458 | 1.1313771 | 4 | 0.7147759 | 4 | 1.16985 |
| 1.193934 | 4 | 0.9683348 | 4 | 1.385393 | 3.0129431 | 0.9286859 | 2.90772 |
| 1.166393 | 4 | 1.0367093 | 4 | 1.194374 | 3.306542 | 0.8589369 | 3.026731 |
| 1.220082 | 4 | 1.1334502 | 4 | 1.447865 | 3.545118 | 1.0057331 | 3.333406 |
| 1.305199 | 4 | 1.0985262 | 4 | 1.336547 | 3.5902275 | 1.0388355 | 3.474805 |
| 4 | 1.1454929 | 4 | 1.1898242 | 4 | 0.7928532 | 4 | 1.308156 |
| 4 | 1.1597881 | 3.8311266 | 1.2618215 | 4 | 0.8298782 | 4 | 1.364803 |
| 4 | 4 | 3.6015496 | 4 | 4 | 2.1612424 | 3.2920354 | 4 |

FIG. 12C

| X2.69 | X2.31 | X2.56 | X2.76 | X2.61 | X2.19 | X2.4 | BB |
|---|---|---|---|---|---|---|---|
| 0.8418593 | 4 | 4 | 4 | 3.7952023 | 0.8771578 | 0.9073292 | 1 |
| 4 | 0.9842393 | 1.034513 | 0.9420885 | 0.9893478 | 4 | 4 | 1 |
| 4 | 1.4668639 | 1.362066 | 1.3427244 | 1.3471408 | 4 | 4 | 1 |
| 1.6105599 | 3.4308267 | 3.257812 | 4 | 3.0271479 | 1.4476707 | 1.4015276 | 1 |
| 4 | 1.3548567 | 1.319537 | 1.3809034 | 1.2277191 | 4 | 4 | 1 |
| 4 | 0.994067 | 1.123866 | 0.9643126 | 1.012584 | 4 | 4 | 1 |
| 4 | 0.9768233 | 1.06409 | 0.9715678 | 0.9192808 | 4 | 4 | 1 |
| 0.9361499 | 3.8374684 | 3.799048 | 4 | 3.7089488 | 0.8878906 | 0.9652528 | 1 |
| 4 | 1.0055387 | 1.035494 | 0.9118764 | 0.9742782 | 4 | 4 | 1 |
| 0.7685242 | 3.6339391 | 3.579978 | 4 | 3.5601823 | 0.8294288 | 0.8876043 | 1 |
| 4 | 0.9390274 | 1.007771 | 0.916734 | 0.9345512 | 4 | 4 | 1 |
| 1.5743984 | 4 | 4 | 4 | 4 | 1.4757147 | 1.5735869 | 1 |
| 4 | 1.1132547 | 1.194972 | 1.0417816 | 1.0629057 | 4 | 4 | 1 |
| 3.0199352 | 2.9541922 | 2.9686 | 3.7176296 | 2.9270866 | 0.7283755 | 1.4365022 | 1 |
| 1 | 3.3655938 | 3.033182 | 4 | 3.1193238 | 0.847144 | 0.9354998 | 1 |
| 4 | 1.126908 | 1.126908 | 0.9707868 | 0.9084799 | 4 | 4 | 1 |
| 4 | 0.9372899 | 1 | 0.8384845 | 0.8949896 | 4 | 4 | 1 |
| 4 | 1.089136 | 1.118014 | 1.0461821 | 1.0117936 | 4 | 4 | 1 |
| 4 | 1.0818776 | 1.156067 | 4 | 1 | 1 | 0.9443621 | 1 |
| 0.9201997 | 4 | 4 | 4 | 4 | 1 | 4 | 1 |
| 1.0453339 | 3.6496364 | 3.379266 | 3.7176296 | 3.1310649 | 0.9673996 | 4 | 1 |
| 4 | 3.4510895 | 3.215765 | 3.5184123 | 3.1720114 | 3.9131973 | 4 | 1 |

FIG. 13A

Table 6: Antibody pattern recognition matrix

| | X2.73 | X2.13 | X2.42 | X2.1 | X2.39 | X2.78 | X2.12 | X2.16 | X2.24 | X2.15 |
|---|---|---|---|---|---|---|---|---|---|---|
| X2.73 | 0 | 1 | 1 | 0 | 1 | 1 | 1 | 0 | 1 | 0 |
| X2.13 | 1 | 0 | 1 | 1 | 1 | 0 | 0 | 1 | 0 | 1 |
| X2.42 | 1 | 1 | 0 | 0 | 1 | 1 | 0 | 1 | 1 | 1 |
| X2.1 | 1 | 1 | 1 | 0 | 1 | 1 | 1 | 1 | 1 | 1 |
| X2.39 | 1 | 0 | 1 | 1 | 0 | 0 | 0 | 0 | 0 | 1 |
| X2.78 | 1 | 0 | 1 | 0 | 0 | 0 | 1 | 0 | 0 | 1 |
| X2.12 | 0 | 0 | 1 | 1 | 1 | 1 | 0 | 1 | 1 | 1 |
| X2.16 | 1 | 0 | 1 | 0 | 0 | 0 | 0 | 0 | 0 | 0 |
| X2.24 | 0 | 0 | 1 | 1 | 1 | 1 | 0 | 0 | 0 | 1 |
| X2.15 | 1 | 0 | 0 | 0 | 1 | 1 | 1 | 1 | 1 | 0 |
| X2.7 | 1 | 1 | 1 | 1 | 1 | 1 | 1 | 1 | 1 | 1 |
| X2.25 | 1 | 1 | 1 | 1 | 0 | 0 | 0 | 0 | 0 | 0 |
| X2.55 | 1 | 0 | 1 | 0 | 0 | 0 | 0 | 0 | 0 | 0 |
| X2.45 | 0 | 0 | 0 | 1 | 1 | 1 | 0 | 0 | 0 | 1 |
| X2.69 | 0 | 0 | 1 | 1 | 1 | 1 | 0 | 0 | 0 | 1 |
| X2.31 | 1 | 1 | 1 | 1 | 0 | 0 | 1 | 1 | 1 | 0 |
| X2.56 | 1 | 0 | 1 | 1 | 1 | 1 | 0 | 0 | 0 | 0 |
| X2.76 | 1 | 0 | 1 | 0 | 0 | 0 | 1 | 1 | 1 | 1 |
| X2.61 | 1 | 0 | 1 | 1 | 1 | 1 | 1 | 1 | 1 | 1 |
| X2.19 | 0 | 1 | 1 | 0 | 0 | 0 | 0 | 0 | 0 | 0 |
| X2.4 | 0 | 1 | 1 | 1 | 1 | 1 | 0 | 0 | 0 | 0 |
| BB | 1 | 1 | 1 | 1 | 1 | 1 | 1 | 1 | 1 | 1 |

| X2.7 | X2.25 | X2.55 | X2.45 | X2.69 | X2.31 | X2.56 | X2.76 | X2.61 | X2.19 | X2.4 | BB |
|---|---|---|---|---|---|---|---|---|---|---|---|
| 1 | 0 | 1 | 0 | 0 | 1 | 1 | 1 | 1 | 0 | 0 | 0 |
| 0 | 1 | 0 | 1 | 1 | 0 | 0 | 0 | 0 | 1 | 1 | 0 |
| 1 | 1 | 1 | 1 | 1 | 1 | 1 | 0 | 0 | 1 | 1 | 0 |
| 1 | 0 | 1 | 0 | 1 | 0 | 0 | 1 | 1 | 0 | 0 | 0 |
| 0 | 1 | 0 | 1 | 1 | 1 | 1 | 0 | 0 | 1 | 1 | 0 |
| 0 | 1 | 0 | 1 | 1 | 0 | 0 | 0 | 0 | 1 | 1 | 0 |
| 0 | 0 | 0 | 0 | 0 | 1 | 1 | 1 | 1 | 0 | 0 | 0 |
| 1 | 1 | 1 | 1 | 1 | 0 | 0 | 0 | 0 | 1 | 1 | 0 |
| 0 | 0 | 0 | 0 | 0 | 1 | 1 | 1 | 1 | 0 | 0 | 0 |
| 1 | 1 | 1 | 1 | 1 | 0 | 0 | 0 | 0 | 1 | 1 | 0 |
| 0 | 0 | 0 | 0 | 1 | 1 | 1 | 1 | 1 | 0 | 1 | 0 |
| 1 | 0 | 1 | 1 | 1 | 0 | 0 | 0 | 0 | 1 | 0 | 0 |
| 1 | 1 | 1 | 1 | 0 | 1 | 1 | 1 | 1 | 0 | 0 | 0 |
| 0 | 1 | 0 | 1 | 1 | 0 | 0 | 0 | 0 | 1 | 1 | 0 |
| 0 | 1 | 0 | 1 | 1 | 1 | 1 | 1 | 1 | 1 | 1 | 0 |
| 0 | 1 | 0 | 1 | 1 | 1 | 1 | 1 | 1 | 1 | 1 | 0 |
| 1 | 0 | 1 | 0 | 0 | 0 | 0 | 0 | 0 | 0 | 0 | 0 |
| 1 | 0 | 1 | 0 | 0 | 1 | 1 | 1 | 1 | 0 | 0 | 0 |
| 1 | 1 | 1 | 1 | 1 | 1 | 1 | 1 | 1 | 1 | 1 | 0 |

FIG. 14A

Table 7: Dissimilarity matrix

| | X2.73 | X2.13 | X2.42 | X2.1 | X2.39 | X2.78 | X2.12 | X2.16 | X2.24 | X2.15 |
|---|---|---|---|---|---|---|---|---|---|---|
| X2.73 | 0 | 20 | 13 | 4 | 19 | 20 | 20 | 0 | 20 | 0 |
| X2.13 | 20 | 0 | 7 | 16 | 1 | 0 | 0 | 20 | 0 | 20 |
| X2.42 | 13 | 7 | 0 | 9 | 6 | 7 | 7 | 13 | 7 | 13 |
| X2.1 | 4 | 16 | 9 | 0 | 15 | 16 | 16 | 4 | 16 | 4 |
| X2.39 | 19 | 1 | 6 | 15 | 0 | 1 | 1 | 19 | 1 | 19 |
| X2.78 | 20 | 0 | 7 | 16 | 1 | 0 | 0 | 20 | 0 | 20 |
| X2.12 | 20 | 0 | 7 | 16 | 1 | 0 | 0 | 20 | 0 | 20 |
| X2.16 | 0 | 20 | 13 | 4 | 19 | 20 | 20 | 0 | 20 | 0 |
| X2.24 | 20 | 0 | 7 | 16 | 1 | 0 | 0 | 20 | 0 | 20 |
| X2.15 | 0 | 20 | 13 | 4 | 19 | 20 | 20 | 0 | 20 | 0 |
| X2.7 | 20 | 0 | 7 | 16 | 1 | 0 | 0 | 20 | 0 | 20 |
| X2.25 | 6 | 14 | 7 | 2 | 13 | 14 | 14 | 6 | 14 | 6 |
| X2.55 | 20 | 0 | 7 | 16 | 1 | 0 | 0 | 20 | 0 | 20 |
| X2.45 | 2 | 20 | 13 | 4 | 19 | 20 | 20 | 2 | 20 | 2 |
| X2.69 | 0 | 20 | 13 | 4 | 19 | 20 | 20 | 0 | 20 | 0 |
| X2.31 | 20 | 0 | 7 | 16 | 1 | 0 | 0 | 20 | 0 | 20 |
| X2.56 | 20 | 0 | 7 | 16 | 1 | 0 | 0 | 20 | 0 | 20 |
| X2.76 | 20 | 0 | 7 | 16 | 1 | 0 | 0 | 20 | 0 | 20 |
| X2.61 | 20 | 0 | 7 | 16 | 1 | 0 | 0 | 20 | 0 | 20 |
| X2.19 | 0 | 20 | 13 | 4 | 19 | 20 | 20 | 0 | 20 | 0 |
| X2.4 | 0 | 20 | 13 | 4 | 19 | 20 | 20 | 0 | 20 | 0 |
| BB | 9 | 11 | 4 | 5 | 10 | 11 | 11 | 9 | 11 | 9 |

| FIG. 14A | FIG. 14B |
|---|---|

| X2.7 | X2.25 | X2.55 | X2.45 | X2.69 | X2.31 | X2.56 | X2.76 | X2.61 | X2.19 | X2.4 | BB |
|---|---|---|---|---|---|---|---|---|---|---|---|
| 20 | 6 | 20 | 2 | 0 | 20 | 20 | 20 | 20 | 0 | 0 | 9 |
| 0 | 14 | 0 | 20 | 20 | 0 | 0 | 0 | 0 | 20 | 20 | 11 |
| 7 | 7 | 7 | 13 | 13 | 7 | 7 | 7 | 7 | 13 | 13 | 4 |
| 16 | 2 | 16 | 4 | 4 | 16 | 16 | 16 | 16 | 4 | 4 | 5 |
| 1 | 13 | 1 | 19 | 19 | 1 | 1 | 1 | 1 | 19 | 19 | 10 |
| 0 | 14 | 0 | 20 | 20 | 0 | 0 | 0 | 0 | 20 | 20 | 11 |
| 0 | 14 | 0 | 20 | 20 | 0 | 0 | 0 | 0 | 20 | 20 | 11 |
| 20 | 6 | 20 | 2 | 0 | 20 | 20 | 20 | 20 | 0 | 0 | 9 |
| 0 | 14 | 0 | 20 | 20 | 0 | 0 | 0 | 0 | 20 | 20 | 11 |
| 20 | 6 | 20 | 2 | 0 | 20 | 20 | 20 | 20 | 0 | 0 | 9 |
| 0 | 14 | 0 | 20 | 20 | 0 | 0 | 0 | 0 | 20 | 20 | 11 |
| 14 | 0 | 14 | 6 | 6 | 14 | 14 | 14 | 14 | 6 | 6 | 3 |
| 0 | 14 | 0 | 20 | 20 | 0 | 0 | 0 | 0 | 20 | 20 | 11 |
| 20 | 6 | 20 | 0 | 2 | 20 | 20 | 20 | 20 | 2 | 2 | 9 |
| 20 | 6 | 20 | 2 | 0 | 20 | 20 | 20 | 20 | 0 | 0 | 9 |
| 0 | 14 | 0 | 20 | 20 | 0 | 0 | 0 | 0 | 20 | 20 | 11 |
| 0 | 14 | 0 | 20 | 20 | 0 | 0 | 0 | 0 | 20 | 20 | 11 |
| 0 | 14 | 0 | 20 | 20 | 0 | 0 | 0 | 0 | 20 | 20 | 11 |
| 20 | 6 | 20 | 2 | 0 | 20 | 20 | 20 | 20 | 0 | 0 | 9 |
| 20 | 6 | 20 | 2 | 0 | 20 | 20 | 20 | 20 | 0 | 0 | 9 |
| 11 | 3 | 11 | 9 | 9 | 11 | 11 | 11 | 11 | 9 | 9 | 0 |

Table 8: Average Dissimilarity matrix

| | X2.73 | X2.13 | X2.42 | X2.1 | X2.39 | X2.78 |
|---|---|---|---|---|---|---|
| X2.73 | 0 | 0.917355372 | 0.7231405 | 0.053719 | 0.8719008 | 0.9173554 |
| X2.13 | 0.91735537 | 0 | 0.2107438 | 0.8884298 | 0.0619835 | 0 |
| X2.42 | 0.7231405 | 0.210743802 | 0 | 0.677686 | 0.1818182 | 0.2107438 |
| X2.1 | 0.053719901 | 0.888429752 | 0.677686 | 0 | 0.8595041 | 0.8884298 |
| X2.39 | 0.871900083 | 0.061983471 | 0.1818182 | 0.8595041 | 0 | 0.0619835 |
| X2.78 | 0.91735537 | 0 | 0.2107438 | 0.8884298 | 0.0619835 | 0 |
| X2.12 | 0.913223140 | 0.004132231 | 0.214876 | 0.892562 | 0.0578512 | 0.0041322 |
| X2.16 | 0.004132231 | 0.921487603 | 0.7272727 | 0.0578512 | 0.8677686 | 0.9214876 |
| X2.24 | 0.91735537 | 0 | 0.2107438 | 0.8884298 | 0.0619835 | 0 |
| X2.15 | 0.008264463 | 0.925619835 | 0.731405 | 0.0619835 | 0.8636364 | 0.9256198 |
| X2.7 | 0.91735537 | 0 | 0.2107438 | 0.8884298 | 0.0619835 | 0 |
| X2.25 | 0.086776860 | 0.847107438 | 0.6363636 | 0.0495868 | 0.8181818 | 0.8471074 |
| X2.55 | 0.913223140 | 0.004132231 | 0.214876 | 0.892562 | 0.0578512 | 0.0041322 |
| X2.45 | 0.070247934 | 0.880165289 | 0.6859504 | 0.107438 | 0.8181818 | 0.8801653 |
| X2.69 | 0.008264463 | 0.925619835 | 0.731405 | 0.0619835 | 0.8636364 | 0.9256198 |
| X2.31 | 0.913223140 | 0.004132231 | 0.214876 | 0.892562 | 0.0578512 | 0.0041322 |
| X2.56 | 0.909090909 | 0.008264463 | 0.2190083 | 0.8966942 | 0.053719 | 0.0082645 |
| X2.76 | 0.91735537 | 0 | 0.2107438 | 0.8884298 | 0.0619835 | 0 |
| X2.61 | 0.921487603 | 0.004132231 | 0.2066116 | 0.8842975 | 0.0661157 | 0.0041322 |
| X2.19 | 0.008264463 | 0.909090909 | 0.714876 | 0.0454546 | 0.8801653 | 0.9090909 |
| X2.4 | 0 | 0.917355372 | 0.7231405 | 0.053719 | 0.8719008 | 0.9173554 |
| BB | 0.413223140 | 0.528925620 | 0.3429752 | 0.3595041 | 0.5165289 | 0.5289256 |

FIG. 15A

| FIG. 15A | FIG. 15B | FIG. 15C |
|---|---|---|

| X2.12 | X2.16 | X2.24 | X2.15 | X2.7 | X2.25 | X2.55 | X2.45 |
|---|---|---|---|---|---|---|---|
| 0.9132231 | 0.0041322 | 0.9173554 | 0.0082645 | 0.9173554 | 0.0867769 | 0.9132231 | 0.0702479 |
| 0.0041322 | 0.9214876 | 0 | 0.9256198 | 0 | 0.8471074 | 0.0041322 | 0.8801653 |
| 0.214876 | 0.7272727 | 0.2107438 | 0.731405 | 0.2107438 | 0.6363636 | 0.214876 | 0.6859504 |
| 0.892562 | 0.0578512 | 0.8884298 | 0.0619835 | 0.8884298 | 0.0495868 | 0.892562 | 0.107438 |
| 0.0578512 | 0.8677686 | 0.0619835 | 0.8636364 | 0.0619835 | 0.8181818 | 0.0578512 | 0.8181818 |
| 0.0041322 | 0.9214876 | 0 | 0.9256198 | 0 | 0.8471074 | 0.0041322 | 0.8801653 |
| 0 | 0.9173554 | 0.0041322 | 0.9214876 | 0.0041322 | 0.8512397 | 0 | 0.8760331 |
| 0.9173554 | 0 | 0.9214876 | 0.0041322 | 0.9214876 | 0.0909091 | 0.9173554 | 0.0661157 |
| 0.0041322 | 0.9214876 | 0 | 0.9256198 | 0 | 0.8471074 | 0.0041322 | 0.8801653 |
| 0.9214876 | 0.0041322 | 0.9256198 | 0 | 0.9256198 | 0.0950413 | 0.9214876 | 0.0619835 |
| 0.0041322 | 0.9214876 | 0 | 0.9256198 | 0 | 0.8471074 | 0.0041322 | 0.8801653 |
| 0.8512397 | 0.0909091 | 0.8471074 | 0.0950413 | 0.8471074 | 0 | 0.8512397 | 0.1487603 |
| 0 | 0.9173554 | 0.0041322 | 0.9214876 | 0.0041322 | 0.8512397 | 0 | 0.8760331 |
| 0.8760331 | 0.0661157 | 0.8801653 | 0.0619835 | 0.8801653 | 0.1487603 | 0.8760331 | 0 |
| 0.9214876 | 0.0041322 | 0.9256198 | 0 | 0.9256198 | 0.0950413 | 0.9214876 | 0.0619835 |
| 0 | 0.9173554 | 0.0041322 | 0.9214876 | 0.0041322 | 0.8512397 | 0 | 0.8760331 |
| 0.0041322 | 0.9132231 | 0.0041322 | 0.9173554 | 0.0041322 | 0.8553719 | 0.0041322 | 0.8719008 |
| 0.0041322 | 0.9214876 | 0 | 0.9256198 | 0 | 0.8471074 | 0.0041322 | 0.8801653 |
| 0.0082645 | 0.9256198 | 0.0041322 | 0.9297521 | 0.0090909 | 0.8429752 | 0.0082645 | 0.8842975 |
| 0.9132231 | 0.0123967 | 0.9090909 | 0.0165289 | 0.9090909 | 0.0785124 | 0.9132231 | 0.0785124 |
| 0.9132231 | 0.0041322 | 0.9173554 | 0.0082645 | 0.9173554 | 0.0867769 | 0.9132231 | 0.0702479 |
| 0.5330579 | 0.4173554 | 0.5289256 | 0.4214876 | 0.5289256 | 0.3264463 | 0.5330579 | 0.392562 |

FIG. 15C

| X2.69 | X2.31 | X2.56 | X2.76 | X2.61 | X2.19 | X2.4 | BB |
|---|---|---|---|---|---|---|---|
| 0.0082645 | 0.9132231 | 0.9090909 | 0.9173554 | 0.9214876 | 0.0082645 | 0 | 0.4132231 |
| 0.9256198 | 0.0041322 | 0.0082645 | 0 | 0.0041322 | 0.9090909 | 0.9173554 | 0.5289256 |
| 0.731405 | 0.214876 | 0.2190083 | 0.2107438 | 0.2066116 | 0.714876 | 0.7231405 | 0.3429752 |
| 0.0619835 | 0.892562 | 0.8966942 | 0.8884298 | 0.8842975 | 0.0454545 | 0.053719 | 0.3595041 |
| 0.8636364 | 0.0578512 | 0.053719 | 0.0619835 | 0.0661157 | 0.8801653 | 0.8719008 | 0.5165289 |
| 0.9256198 | 0.0041322 | 0.0082645 | 0 | 0.0041322 | 0.9090909 | 0.9173554 | 0.5289256 |
| 0.9214876 | 0 | 0.0041322 | 0.0041322 | 0.0082645 | 0.9132231 | 0.9132231 | 0.5330579 |
| 0.0041322 | 0.9173554 | 0.9132231 | 0.9214876 | 0.9256198 | 0.0123967 | 0.0041322 | 0.4173554 |
| 0.9256198 | 0.0041322 | 0.0082645 | 0 | 0.0041322 | 0.9090909 | 0.9173554 | 0.5289256 |
| 0 | 0.9214876 | 0.9173554 | 0.9256198 | 0.9297521 | 0.0165289 | 0.0082645 | 0.4214876 |
| 0.9256198 | 0.0041322 | 0.0082645 | 0 | 0.0041322 | 0.9090909 | 0.9173554 | 0.5289256 |
| 0.0950413 | 0.8512397 | 0.8553719 | 0.8471074 | 0.8429752 | 0.0785124 | 0.0867769 | 0.3264463 |
| 0.9214876 | 0 | 0.0041322 | 0.0041322 | 0.0082645 | 0.9132231 | 0.9132231 | 0.5330579 |
| 0.0619835 | 0.8760331 | 0.8719008 | 0.8801653 | 0.8842975 | 0.0785124 | 0.07024797 | 0.392562 |
| 0 | 0.9214876 | 0.9173554 | 0.9256198 | 0.9297521 | 0.0165289 | 0.0082645 | 0.4214876 |
| 0.9214876 | 0 | 0.0041322 | 0.0041322 | 0.0082645 | 0.9132231 | 0.9132231 | 0.5330579 |
| 0.9173554 | 0.0041322 | 0.0041322 | 0.0082645 | 0.0123967 | 0.9173554 | 0.9090909 | 0.5371901 |
| 0.9256198 | 0.0041322 | 0.0082645 | 0.0041322 | 0.0041322 | 0.9090909 | 0.9173554 | 0.5289256 |
| 0.9297521 | 0.0082645 | 0.01239967 | 0.9090909 | 0 | 0.9132231 | 0.9214876 | 0.5247934 |
| 0.0165289 | 0.9132231 | 0.9173554 | 0.9173554 | 0.9132231 | 0 | 0.0082645 | 0.4049587 |
| 0.0082645 | 0.9132231 | 0.9090909 | 0.9173554 | 0.9214876 | 0.0082645 | 0 | 0.4132231 |
| 0.4214876 | 0.5330579 | 0.5371901 | 0.5289256 | 0.5247934 | 0.4049587 | 0.4132231 | 0 |

FIG. 16A

Table 9: Permuted Average Dissimilarity matrix

|  | X2.73 | X2.4 | X2.16 | X2.15 | X2.69 | X2.19 |
|---|---|---|---|---|---|---|
| X2.73 | 0 |  |  |  | 0.0082645 | 0.008264 |
| X2.4 | 0 |  |  |  | 0.0082645 | 0.008264 |
| X2.16 | 0.004132 | 0.004132 |  | 0.004132 | 0.0041322 | 0.012397 |
| X2.15 | 0.008264 | 0.008264 | 0.004132 |  | 0 | 0.016529 |
| X2.69 | 0.008264 | 0.008264 | 0.004132 | 0 |  | 0.016529 |
| X2.19 | 0.008264 | 0.008264 | 0.012397 | 0.0165289 | 0.0165289 | 0 |
| X2.45 | 0.070248 | 0.070248 | 0.066116 | 0.061983 | 0.0619835 | 0.078512 |
| X2.1 | 0.053719 | 0.053719 | 0.057851 | 0.061983 | 0.0619835 | 0.045455 |
| X2.25 | 0.086777 | 0.086777 | 0.090909 | 0.095041 | 0.0950413 | 0.078512 |
| BB | 0.413223 | 0.413223 | 0.417355 | 0.421488 | 0.4214876 | 0.404959 |
| X2.13 | 0.917355 | 0.917355 | 0.921488 | 0.92562 | 0.9256198 | 0.909091 |
| X2.78 | 0.917355 | 0.917355 | 0.921488 | 0.92562 | 0.9256198 | 0.909091 |
| X2.24 | 0.917355 | 0.917355 | 0.921488 | 0.92562 | 0.9256198 | 0.909091 |
| X2.7 | 0.917355 | 0.917355 | 0.921488 | 0.92562 | 0.9256198 | 0.909091 |
| X2.76 | 0.921488 | 0.921488 | 0.92562 | 0.929752 | 0.9297521 | 0.913223 |
| X2.61 | 0.913223 | 0.913223 | 0.917355 | 0.921488 | 0.9214876 | 0.913223 |
| X2.12 | 0.913223 | 0.913223 | 0.917355 | 0.921488 | 0.9214876 | 0.913223 |
| X2.55 | 0.913223 | 0.913223 | 0.917355 | 0.921488 | 0.9214876 | 0.913223 |
| X2.31 | 0.913223 | 0.913223 | 0.917355 | 0.921488 | 0.9214876 | 0.913223 |
| X2.56 | 0.909091 | 0.909091 | 0.913223 | 0.917355 | 0.9173554 | 0.917355 |
| X2.39 | 0.871901 | 0.871901 | 0.867769 | 0.863636 | 0.8636364 | 0.880165 |
| X2.42 | 0.723140 | 0.723140 | 0.727273 | 0.731405 | 0.7314050 | 0.714876 |

| FIG. 16A | FIG. 16B | FIG. 16C |
|---|---|---|

| X2.45 | X2.1 | X2.25 | BB | X2.13 | X2.78 | X2.24 | X2.7 |
|---|---|---|---|---|---|---|---|
| 0.070248 | 0.053719 | 0.086777 | 0.413223 | 0.917355 | 0.917355 | 0.917355 | 0.917355 |
| 0.070248 | 0.053719 | 0.086777 | 0.413223 | 0.917355 | 0.917355 | 0.917355 | 0.917355 |
| 0.066116 | 0.057851 | 0.090909 | 0.417355 | 0.921488 | 0.921488 | 0.921488 | 0.921488 |
| 0.061983 | 0.061983 | 0.095041 | 0.421488 | 0.925620 | 0.925620 | 0.925620 | 0.925620 |
| 0.061983 | 0.061983 | 0.095041 | 0.421488 | 0.925620 | 0.925620 | 0.925620 | 0.925620 |
| 0.078512 | 0.045455 | 0.078512 | 0.404959 | 0.909091 | 0.909091 | 0.909091 | 0.909091 |
| 0 | 0.107438 | 0.14876 | 0.392562 | 0.880165 | 0.880165 | 0.880165 | 0.880165 |
| 0.107438 | 0 | 0.049587 | 0.359504 | 0.88843 | 0.88843 | 0.88843 | 0.88843 |
| 0.14876 | 0.049587 | 0 | 0.326446 | 0.847107 | 0.847107 | 0.847107 | 0.847107 |
| 0.392562 | 0.359504 | 0.326446 | 0 | 0.528926 | 0.528926 | 0.528926 | 0.528926 |
| 0.880165 | 0.88843 | 0.847107 | 0.528926 | 0 | 0 | 0 | 0 |
| 0.880165 | 0.88843 | 0.847107 | 0.528926 | 0 | 0 | 0 | 0 |
| 0.880165 | 0.88843 | 0.847107 | 0.528926 | 0 | 0 | 0 | 0 |
| 0.880165 | 0.88843 | 0.847107 | 0.528926 | 0 | 0 | 0 | 0 |
| 0.884298 | 0.884298 | 0.842975 | 0.524793 | 0.004132 | 0.004132 | 0.004132 | 0.004132 |
| 0.876033 | 0.892562 | 0.85124 | 0.533058 | 0.004132 | 0.004132 | 0.004132 | 0.004132 |
| 0.876033 | 0.892562 | 0.85124 | 0.533058 | 0.004132 | 0.004132 | 0.004132 | 0.004132 |
| 0.876033 | 0.892562 | 0.85124 | 0.533058 | 0.004132 | 0.004132 | 0.004132 | 0.004132 |
| 0.871901 | 0.896694 | 0.855372 | 0.53719 | 0.008264 | 0.008264 | 0.008264 | 0.008264 |
| 0.818182 | 0.859504 | 0.818182 | 0.516529 | 0.061983 | 0.061983 | 0.061983 | 0.061983 |
| 0.68595 | 0.677686 | 0.636364 | 0.342975 | 0.210744 | 0.210744 | 0.210744 | 0.210744 |

FIG. 16C

| X2.76 | X2.61 | X2.12 | X2.55 | X2.31 | X2.56 | X2.39 | X2.42 |
|---|---|---|---|---|---|---|---|
| 0.9173554 | 0.9214876 | 0.913223 | 0.913223 | 0.913223 | 0.909091 | 0.871901 | 0.7231405 |
| 0.9173554 | 0.9214876 | 0.913223 | 0.913223 | 0.913223 | 0.909091 | 0.871901 | 0.7231405 |
| 0.9214876 | 0.925619834 | 0.917355 | 0.917355 | 0.917355 | 0.913223 | 0.8677769 | 0.7272727 |
| 0.9256198 | 0.92975207 | 0.921488 | 0.921488 | 0.921488 | 0.917355 | 0.863636 | 0.731405 |
| 0.9256198 | 0.92975207 | 0.921488 | 0.921488 | 0.921488 | 0.917355 | 0.863636 | 0.731405 |
| 0.9090909 | 0.913223140 | 0.913223 | 0.913223 | 0.913223 | 0.917355 | 0.800165 | 0.714876 |
| 0.8801653 | 0.884297521 | 0.876033 | 0.876033 | 0.876033 | 0.871901 | 0.818182 | 0.6859504 |
| 0.8884298 | 0.884297521 | 0.892562 | 0.892562 | 0.892562 | 0.896694 | 0.859504 | 0.677686 |
| 0.8471074 | 0.842975207 | 0.85124 | 0.85124 | 0.85124 | 0.855372 | 0.818182 | 0.6363636 |
| 0.5289256 | 0.524793388 | 0.533058 | 0.533058 | 0.533058 | 0.537190 | 0.516529 | 0.3429752 |
| 0 | 0.000413223 | 0.004132 | 0.004132 | 0.004132 | 0.008264 | 0.061983 | 0.2107438 |
| 0 | 0.000413223 | 0.004132 | 0.004132 | 0.004132 | 0.008264 | 0.061983 | 0.2107438 |
| 0 | 0.000413223 | 0.004132 | 0.004132 | 0.004132 | 0.008264 | 0.061983 | 0.2107438 |
| 0 | 0.000413223 | 0.004132 | 0.004132 | 0.004132 | 0.008264 | 0.061983 | 0.2107438 |
| 0.0041322 | 0 | 0.008264 | 0.008264 | 0.008264 | 0.012397 | 0.066116 | 0.2066116 |
| 0.0041322 | 0.008264446 | 0 | 0 | 0 | 0.004132 | 0.057851 | 0.214876 |
| 0.0041322 | 0.008264446 | 0 | 0 | 0 | 0.004132 | 0.057851 | 0.214876 |
| 0.0041322 | 0.008264446 | 0.004132 | 0.004132 | 0.004132 | 0.004132 | 0.057851 | 0.214876 |
| 0.0082645 | 0.012396694 | 0.004132 | 0.004132 | 0.004132 | 0 | 0.053719 | 0.2190083 |
| 0.0619835 | 0.066115702 | 0.057851 | 0.057851 | 0.057851 | 0.053719 | 0 | 0.1818182 |
| 0.2107438 | 0.206611570 | 0.214876 | 0.214876 | 0.214876 | 0.219008 | 0.181818 | 0 |

FIG. 17A

Table 10: Permuted normalized intensity matrix

| | X2.73 | X2.4 | X2.16 | X2.15 | X2.69 | X2.19 |
|---|---|---|---|---|---|---|
| X2.73 | 1 | 0.9073292 | 0.947242 | 0.99516 | 0.841859 | 0.877158 |
| X2.4 | 1.302706 | 1 | 1.159788 | 1.261822 | 1.045334 | 0.9674 |
| X2.16 | 1.173271 | 0.9652528 | 1 | 1.122911 | 0.93615 | 0.887891 |
| X2.15 | 1.056192 | 0.8876043 | 0.920182 | 1 | 0.768524 | 0.829429 |
| X2.69 | 1.140823 | 0.9354998 | 1.002695 | 1.131377 | 1 | 0.847144 |
| X2.19 | 1.273509 | 0.9443621 | 1.145493 | 1.189824 | 0.9202 | 1 |
| X2.45 | 0.881556 | 1.4365022 | 1.215564 | 1.488728 | 3.019935 | 0.728376 |
| X2.1 | 1.70902 | 1.4015276 | 1.589673 | 1.697691 | 1.61056 | 1.447671 |
| X2.25 | 1.771658 | 1.5735869 | 1.809703 | 1.898277 | 1.574398 | 1.475715 |
| BB | 4 | 4 | 4 | 4 | 4 | 3.913197 |
| X2.13 | 4 | 4 | 4 | 4 | 4 | 4 |
| X2.78 | 4 | 4 | 4 | 4 | 4 | 4 |
| X2.24 | 4 | 4 | 4 | 4 | 4 | 4 |
| X2.7 | 4 | 4 | 4 | 4 | 4 | 4 |
| X2.76 | 4 | 4 | 4 | 4 | 4 | 4 |
| X2.61 | 4 | 4 | 4 | 4 | 4 | 4 |
| X2.12 | 4 | 4 | 4 | 4 | 4 | 4 |
| X2.55 | 4 | 4 | 4 | 4 | 4 | 4 |
| X2.31 | 4 | 4 | 4 | 4 | 4 | 4 |
| X2.56 | 4 | 4 | 4 | 4 | 4 | 4 |
| X2.39 | 4 | 4 | 4 | 4 | 4 | 4 |
| X2.42 | 4 | 4 | 4 | 4 | 4 | 4 |

FIG. 17

| FIG. 17A | FIG. 17B | FIG. 17C |
|---|---|---|

FIG. 17B

| X2.45 | X2.1 | X2.25 | BB | X2.13 | X2.78 | X2.24 | X2.7 |
|---|---|---|---|---|---|---|---|
| 1.035553 | 0.870745 | 0.719966 | 1 | 4 | 3.913167 | 4 | 4 |
| 1.364803 | 0.950974 | 0.829878 | 1 | 3.610753 | 3.364389 | 3.831127 | 4 |
| 1.186474 | 0.840581 | 0.770622 | 1 | 3.958347 | 3.797146 | 4 | 4 |
| 1.27336 | 0.834633 | 0.727252 | 1 | 3.644519 | 3.62783 | 3.903576 | 4 |
| 1.16985 | 0.844274 | 0.714776 | 1 | 3.646732 | 3.290604 | 3.758346 | 4 |
| 1.308156 | 1.05067 | 0.792853 | 1 | 4 | 4 | 4 | 4 |
| 1 | 0.651148 | 0.680622 | 1 | 3.176289 | 3.006249 | 3.301384 | 4 |
| 1.469302 | 1 | 1.102531 | 1 | 3.737949 | 3.319058 | 3.574503 | 4 |
| 1.833547 | 1.496663 | 1 | 1 | 4 | 4 | 4 | 4 |
| 4 | 4 | 2.161242 | 1 | 4 | 3.742197 | 3.60155 | 4 |
| 3.340229 | 4 | 4 | 1 | 1 | 0.968645 | 1.044538 | 1.40836 |
| 3.4884 | 4 | 4 | 1 | 1.023573 | 1 | 1.070304 | 1.24736 |
| 2.996721 | 4 | 3.274955 | 1 | 1.021519 | 1.052479 | 1 | 1.35561 |
| 3.157109 | 4 | 3.530546 | 1 | 0.950771 | 1.068546 | 0.979958 | 1 |
| 3.333406 | 4 | 3.545118 | 1 | 1.116049 | 1.145996 | 1.13345 | 1.44787 |
| 3.474805 | 4 | 3.590228 | 1 | 1.184755 | 1.21962 | 1.098526 | 1.33655 |
| 3.248801 | 4 | 3.737732 | 1 | 0.84279 | 0.916637 | 0.949453 | 1.26045 |
| 3.136672 | 4 | 2.944988 | 1 | 1.154067 | 1.194255 | 1.157763 | 1.47672 |
| 2.90772 | 4 | 3.012943 | 1 | 1.073741 | 1.063124 | 0.968335 | 1.38539 |
| 3.026731 | 4 | 3.306542 | 1 | 1.070507 | 1.087584 | 1.036709 | 1.19437 |
| 2.356879 | 4 | 2.76457 | 1 | 1.303855 | 1.270583 | 1.33777 | 2.37581 |
| 2.282016 | 3.766454 | 2.267369 | 1 | 2.075228 | 2.289972 | 1.569858 | 4 |

FIG. 17C

| X2.76 | X2.61 | X2.12 | X2.55 | X2.31 | X2.56 | X2.39 | X2.42 |
|---|---|---|---|---|---|---|---|
| 4 | 3.7952023 | 4 | 4 | 4 | 4 | 3.173809 | 1.843531 |
| 4 | 3.1310649 | 4 | 4 | 3.649636 | 3.379266 | 2.76392 | 1.856921 |
| 4 | 3.7089488 | 4 | 4 | 3.837468 | 3.799048 | 2.852716 | 1.777825 |
| 4 | 3.5601823 | 3.91183 | 4 | 3.633939 | 3.579978 | 2.881995 | 1.670087 |
| 4 | 3.1193238 | 3.437422 | 4 | 3.365594 | 3.033182 | 2.883401 | 1.650839 |
| 4 | 4 | 4 | 4 | 4 | 4 | 3.509281 | 2.090315 |
| 3.7176296 | 2.9270866 | 3.271278 | 3.954025 | 2.954192 | 2.9686 | 2.362549 | 1.414378 |
| 4 | 3.0271479 | 4 | 4 | 3.430827 | 3.257812 | 3.60482 | 2.394268 |
| 4 | 4 | 4 | 4 | 4 | 4 | 3.811799 | 2.291334 |
| 3.51841 23 | 3.1720114 | 4 | 3.292035 | 3.45109 | 3.215765 | 2.877579 | 2.31 |
| 0.9420885 | 0.9893478 | 1.186764 | 0.879184 | 0.984239 | 1.0345 13 | 1.301896 | 2.062295 |
| 0.9643126 | 1.012584 | 1.144814 | 0.984651 | 0.994067 | 1.123866 | 1.166439 | 2.082761 |
| 0.9118764 | 0.9742782 | 1.186255 | 0.908475 | 1.005539 | 1.035494 | 1.159606 | 2.071926 |
| 0.916734 | 0.9345512 | 1.082686 | 0.92793 | 0.939027 | 1.007771 | 1.217451 | 2.03199 |
| 1 | 1.0117936 | 1.220082 | 1.005733 | 1.089136 | 1.118014 | 1.236116 | 2.098367 |
| 1.0461821 | 1 | 1.305199 | 1.038836 | 1.081878 | 1.156067 | 1.322849 | 2.129265 |
| 0.9715678 | 0.9192808 | 1 | 0.920955 | 0.976823 | 1.06409 | 1.15927 | 1.997578 |
| 1.0417816 | 1.0629057 | 1.356987 | 1 | 1.113255 | 1.194972 | 1.195475 | 1.906452 |
| 0.9707868 | 0.9084799 | 1.193934 | 0.928686 | 1 | 1.126908 | 1.118371 | 1.946576 |
| 0.8384845 | 0.8949896 | 1.166393 | 0.8589 37 | 0.93729 | 1 | 1.239202 | 1.892157 |
| 1.3809034 | 1.2277191 | 1.43525 | 1.368373 | 1.354857 | 1.319537 | 1 | 1.677859 |
| 1.3427244 | 1.3471408 | 2.279704 | 1.583682 | 1.466864 | 1.352066 | 1.919685 | 2.298774 |

FIG. 18A

Table 11: Permuted Average Dissimilarity matrix for five Antigen 39 Input Data Sets

| | X1.17 | X1.55 | X1.16 | X1.11 | X1.12 | X1.63 |
|---|---|---|---|---|---|---|
| X1.17 | 0 | | | 0.003367 | 0.034483 | 0.15047 |
| X1.55 | 0 | | | 0.003367 | 0.034483 | 0.15047 |
| X1.16 | 0 | 0.003367003 | | 0 | 0.009091 | 0.186364 |
| X1.11 | 0.00337 | 0.034482759 | 0.009091 | | 0.031348 | 0.164983 |
| X1.12 | 0.03448 | 0.150470219 | 0.186364 | 0.031348 | 0 | 0.159875 |
| X1.63 | 0.15047 | 0.140151515 | 0.187879 | 0.164983 | 0.159875 | 0 |
| X1.21 | 0.14015 | 0.128787879 | 0.157576 | 0.136364 | 0.096257 | 0.181818 |
| X2.12 | 0.12879 | 0.175324675 | | 0.125 | 0.082888 | 0.147727 |
| X2.38 | 0.17532 | 0.246753247 | — | 0.168831 | 0.075758 | 0.149351 |
| X2.35 | 0.24675 | 0.233766234 | — | 0.253247 | 0.155303 | 0.194805 |
| X2.1 | 0.23377 | 0.359090909 | 0.359091 | 0.214286 | 0.159091 | 0.207792 |
| X1.66 | 0.35909 | 0.460815047 | 0.422727 | 0.359091 | 0.35 | 0.336364 |
| X1.1 | 0.46082 | 0.404040404 | 0.4 | 0.461279 | 0.432602 | 0.37931 |
| X1.8 | 0.40404 | — | — | 0.433333 | 0.432602 | 0.377104 |
| X1.30 | — | 0.439393939 | 0.3 | 0.363636 | 0.3 | — |
| X1.38 | 0.43939 | 0.379310345 | 0.354545 | 0.473684 | 0.444805 | 0.40404 |
| X1.3 | 0.37931 | 0.420454545 | 0.303030 | 0.406061 | 0.39627 | 0.347962 |
| X1.32 | 0.42045 | 0.430454545 | 0.430303 | 0.424242 | 0.430481 | 0.454546 |

FIG. 18

| FIG. 18A | FIG. 18B | FIG. 18C | FIG. 18D | FIG. 18E |
|---|---|---|---|---|
| FIG. 18F | FIG. 18G | FIG. 18H | FIG. 18I | FIG. 18J |

FIG. 18B

| X1.21 | X2.12 | X2.38 | X2.35 | X2.1 | X1.66 | X1.1 | X1.8 | X1.30 |
|---|---|---|---|---|---|---|---|---|
| 0.140152 | 0.128788 | 0.175325 | 0.246753 | 0.233766 | 0.359091 | 0.460815 | 0.404040 | --- |
| 0.140152 | 0.128788 | 0.175325 | 0.246753 | 0.233766 | 0.359091 | 0.460815 | 0.404040 | --- |
| 0.187879 | 0.157576 | --- | --- | --- | 0.359091 | 0.422727 | 0.4 | --- |
| 0.136364 | 0.125 | 0.168831 | 0.253247 | 0.214286 | 0.359091 | 0.461279 | 0.433333 | 0.3636364 |
| 0.096257 | 0.082888 | 0.075758 | 0.155303 | 0.159091 | 0.35 | 0.432602 | 0.4326019 | 0.3 |
| 0.181818 | 0.147727 | 0.149351 | 0.194805 | 0.207792 | 0.336364 | 0.37931 | 0.3771044 | --- |
| 0 | 0.040107 | 0.079545 | 0.159091 | 0.162879 | 0.533333 | 0.575758 | 0.5530303 | 0.3333333 |
| 0.040107 | 0 | 0.068182 | 0.132576 | 0.136364 | 0.50303 | 0.526515 | 0.5416667 | 0.3636364 |
| 0.079545 | 0.068182 | 0 | 0.079545 | 0.098485 | --- | 0.363636 | 0.487013 | --- |
| 0.159091 | 0.132576 | 0.079545 | 0 | 0.109848 | --- | 0.357143 | 0.4805195 | --- |
| 0.162879 | 0.136364 | 0.098485 | 0.109848 | 0 | --- | 0.4350065 | 0.5454546 | --- |
| 0.533333 | 0.50303 | 0.363636 | 0.357143 | 0.4350065 | 0 | 0.063636 | 0.0409091 | 0 |
| 0.575758 | 0.526515 | 0.487013 | 0.480519 | 0.545455 | 0.063636 | 0 | 0.0074074 | 0 |
| 0.55303 | 0.541667 | 0.44697 | 0.390152 | 0.439394 | 0.040909 | 0.074074 | 0 | --- |
| 0.333333 | 0.363636 | 0.450758 | 0.409091 | 0.488636 | 0.081818 | 0.166667 | 0.062201 | 0.0165289 |
| 0.444444 | 0.454545 | 0.450758 | 0.409091 | 0.488636 | 0.313636 | 0.213166 | 0.2090909 | 0.2892562 |
| 0.483957 | 0.454545 | 0.420455 | 0.386364 | 0.450758 | 0.290909 | 0.25 | 0.1969697 | 0.2626263 |
| 0.435829 | 0.406417 | | | | | | | |

FIG. 18C

| X1.38 | X1.3 | X1.32 | X1.57 | X1.61 | X1.23 | X2.28.33 | X1.24 | X2.34 |
|---|---|---|---|---|---|---|---|---|
| 0.4393939 | 0.37931 | 0.420455 | 0.395455 | 0.38961 | 0.4 | 0.2964427 | 0.350168 | 0.393939 |
| 0.4393939 | 0.37931 | 0.420455 | 0.395455 | 0.38961 | 0.4 | 0.2964427 | 0.350168 | 0.393939 |
| 0.3 | 0.354546 | 0.430303 | 0.395455 | 0.4 | 0.4 | 0.2857143 | 0.395455 | 0.412121 |
| 0.4736842 | 0.406061 | 0.424242 | 0.343874 | 0.37931 | 0.4 | 0.3116883 | 0.39697 | 0.356061 |
| 0.4448052 | 0.39627 | 0.430481 | 0.35124 | 0.354067 | 0.390909 | 0.2924901 | 0.394984 | 0.347594 |
| 0.4040404 | 0.347962 | 0.454546 | 0.309091 | 0.305195 | 0.313636 | 0.2648221 | 0.329966 | 0.337121 |
| 0.4444444 | 0.483957 | 0.435829 | 0.513369 | 0.451791 | 0.587879 | 0.4031621 | 0.507576 | 0.368984 |
| 0.4545455 | 0.454546 | 0.406417 | 0.454545 | 0.410468 | 0.521212 | 0.3794466 | 0.473485 | 0.339572 |
| 0.4469697 | 0.450758 | 0.420455 |  | 0.287879 |  | 0.3076923 | 0.331169 | 0.291667 |
| 0.3901515 | 0.409091 | 0.386364 |  | 0.246212 |  | 0.2797203 | 0.363636 | 0.242424 |
| 0.4393939 | 0.486636 | 0.450758 |  | 0.333333 |  | 0.3776224 | 0.38961 | 0.329545 |
| 0.0818182 | 0.313636 | 0.290909 | 0.3 | 0.304545 | 0.304545 | 0.1493507 | 0.318182 | 0.224242 |
| 0.1666667 | 0.213166 | 0.25 | 0.245455 | 0.25 | 0.25 | 0.173913 | 0.383838 | 0.162879 |
| 0.062201 | 0.209091 | 0.19697 | 0.343874 | 0.344828 | 0.3 | 0.1688312 | 0.363636 | 0.234848 |
| 0.0165289 | 0.289256 | 0.262626 | 0.53719 | 0.545455 |  | 0.438017 | 0.3232323 |
| 0 | 0.137931 | 0.158249 | 0.454545 | 0.404389 | 0.4 | 0.2556818 | 0.45933 | 0.212121 |
| 0.137931 | 0 | 0.165775 | 0.284585 | 0.291375 | 0.227273 | 0.1501976 | 0.293939 | 0.163102 |
| 0.1582492 | 0.165775 | 0 | 0.508021 | 0.415978 | 0.515152 | 0.3715415 | 0.484848 | 0.254011 |

FIG. 18D

| X2.2 | X2.7 | X2.21 | X2.31 | X1.31 | X2.17 | X1.46 | X2.2.C5 | X1.65 |
|---|---|---|---|---|---|---|---|---|
| 0.489177 | 0.428571 | 0.448052 | 0.5194805 | 0.448276 | 0.471861 | 0.429467 | 0.422078 | 0.4 |
| 0.489177 | 0.428571 | 0.448052 | 0.5194805 | 0.448276 | 0.471861 | 0.429467 | 0.422078 | 0.4 |
| 0.583333 | --- | --- | --- | 0.45 | 0.5 | 0.445455 | --- | 0.4 |
| 0.458874 | 0.363636 | 0.415584 | 0.5064935 | 0.416928 | 0.428571 | 0.420875 | 0.357143 | 0.4 |
| 0.431085 | 0.359848 | 0.344697 | 0.3939394 | 0.384615 | 0.390029 | 0.420063 | 0.284091 | 0.390909 |
| 0.471861 | 0.337662 | 0.357143 | 0.4675325 | 0.410658 | 0.515152 | 0.39185 | 0.422078 | 0.377273 |
| 0.407625 | 0.340909 | 0.356061 | 0.3977273 | 0.377005 | 0.378299 | 0.393939 | 0.30303 | 0.478788 |
| 0.404692 | 0.329545 | 0.329545 | 0.3712121 | 0.406417 | 0.410557 | 0.443182 | 0.314394 | 0.545455 |
| 0.352273 | 0.306818 | 0.276515 | 0.3560606 | 0.375 | 0.367424 | 0.467532 | 0.314394 | --- |
| 0.310606 | 0.227273 | 0.19697 | 0.2992424 | 0.401515 | 0.393939 | 0.461039 | 0.340909 | --- |
| 0.375 | 0.306818 | 0.276515 | 0.3484848 | 0.382576 | 0.375 | 0.461039 | 0.32197 | --- |
| 0.3181818 | --- | --- | --- | 0.354545 | 0.371212 | 0.35 | --- | 0.304545 |
| 0.203463 | 0.227273 | 0.181818 | 0.3181818 | 0.376176 | 0.367965 | 0.369906 | 0.337662 | 0.322727 |
| 0.25974 | 0.344156 | 0.344156 | 0.474026 | 0.347962 | 0.333333 | 0.309764 | 0.285714 | 0.3 |
| 0.193182 | 0.162879 | 0.200758 | 0.2651515 | 0.2 | 0.443182 | 0.348485 | 0.435606 | --- |
| 0.164223 | 0.212121 | 0.234848 | 0.3446970 | 0.405844 | 0.434018 | 0.30094 | 0.469697 | 0.227273 |
| 0.184751 | 0.242424 | 0.287879 | 0.3446970 | 0.365967 | 0.478006 | 0.477273 | 0.484848 | 0.563636 |

FIG. 18E

| X1.29 | X1.53 | X1.59 | X1.13 | X2.2A12 | BB1 | BB |
|---|---|---|---|---|---|---|
| 0.373041 | 0.517241 | 0.580808 | 0.689394 | 0.511364 | 0.62987 | 0.633229 |
| 0.373041 | 0.517241 | 0.580808 | 0.689394 | 0.511364 | 0.62987 | 0.633229 |
| 0.372727 | 0.463636 | 0.509091 | 0.70303 | 0.569697 | -- | 0.65 |
| 0.377104 | 0.569697 | 0.641148 | 0.708333 | 0.511364 | 0.597403 | 0.642424 |
| 0.344828 | 0.400932 | 0.415584 | 0.542781 | 0.494652 | 0.606061 | 0.634033 |
| 0.335423 | 0.529781 | 0.565657 | 0.602273 | 0.484849 | 0.62987 | 0.670846 |
| 0.386364 | 0.513369 | 0.434343 | 0.483957 | 0.398396 | 0.587121 | 0.537433 |
| 0.420455 | 0.473262 | 0.410774 | 0.497326 | 0.411765 | 0.575758 | 0.550802 |
| 0.383117 | 0.397727 | 0.393939 | 0.454546 | 0.386364 | 0.575758 | 0.583333 |
| 0.376623 | 0.378788 | 0.32197 | 0.397727 | 0.367424 | 0.549242 | 0.579545 |
| 0.38961 | 0.443182 | 0.386364 | 0.462121 | 0.386364 | 0.484848 | 0.530303 |
| 0.277273 | 0.504546 | 0.618182 | 0.575758 | 0.672727 | -- | 0.745455 |
| 0.30721 | 0.420063 | 0.479798 | 0.435606 | 0.545455 | 0.714286 | 0.717868 |
| 0.265993 | 0.5 | 0.631579 | 0.541667 | 0.518939 | 0.720779 | 0.675758 |
| -- | 0.661157 | 0.676686 | 0.686869 | 0.414141 | -- | 0.636364 |
| 0.333333 | 0.495298 | 0.473354 | 0.427609 | 0.279461 | 0.530303 | 0.570533 |
| 0.257053 | 0.304546 | 0.423198 | 0.42246 | 0.374332 | 0.496212 | 0.595455 |
| 0.469697 | 0.483957 | 0.505051 | 0.44385 | 0.229947 | 0.481061 | 0.481283 |

| | | | | | | |
|---|---|---|---|---|---|---|
| X1.57 | 0.39545 | 0.395454545 | 0.395455 | 0.343874 | 0.35124 | 0.309091 |
| X1.61 | 0.38961 | 0.389610389 | 0.4 | 0.379931 | 0.354067 | 0.305195 |
| X1.23 | 0.4 | 0.4 | 0.4 | 0.4 | 0.390909 | 0.313636 |
| X2.28.33 | 0.29644 | 0.296442688 | 0.285714 | 0.311688 | 0.229249 | 0.264822 |
| X1.24 | 0.35017 | 0.350168350 | 0.395455 | 0.39697 | 0.394984 | 0.329966 |
| X2.34 | 0.39394 | 0.393939394 | 0.412121 | 0.356061 | 0.347594 | 0.337121 |
| X2.2 | 0.48918 | 0.489177489 | 0.583333 | 0.458874 | 0.431085 | 0.471862 |
| X2.7 | 0.42857 | 0.428571429 | | 0.363636 | 0.359848 | 0.337662 |
| X2.21 | 0.44805 | 0.448051948 | | 0.415584 | 0.344697 | 0.357143 |
| X2.31 | 0.51948 | 0.519480519 | | 0.506494 | 0.393939 | 0.467533 |
| X1.31 | 0.44828 | 0.448275862 | 0.45 | 0.416928 | 0.384615 | 0.410658 |
| X2.17 | 0.47186 | 0.471861472 | 0.5 | 0.428571 | 0.390029 | 0.515152 |
| X1.46 | 0.42947 | 0.429467085 | 0.445455 | 0.420875 | 0.420063 | 0.39185 |
| X2.2.C5 | 0.42208 | 0.422077922 | | 0.357143 | 0.284091 | 0.422078 |
| X1.65 | 0.4 | 0.4 | 0.4 | 0.4 | 0.390909 | 0.377273 |
| X1.29 | 0.37304 | 0.373040752 | 0.372727 | 0.377104 | 0.344828 | 0.335423 |
| X1.53 | 0.51724 | 0.517241379 | 0.463636 | 0.569697 | 0.409932 | 0.529781 |
| X1.59 | 0.58081 | 0.580808081 | 0.509091 | 0.641148 | 0.415584 | 0.565657 |
| X1.13 | 0.68939 | 0.689393939 | 0.70303 | 0.708333 | 0.542781 | 0.602273 |
| X2.2A12 | 0.51136 | 0.511363636 | 0.569697 | 0.511364 | 0.494652 | 0.484849 |
| BB1 | 0.62987 | 0.629870013 | | 0.597403 | 0.606061 | 0.629687 |
| BB | 0.63323 | 0.633222884 | 0.65 | 0.642424 | 0.634033 | 0.670846 |

*FIG. 18F*

| | | | | | | | | |
|---|---|---|---|---|---|---|---|---|
| 0.513369 | 0.454545 | | | | | 0.245455 | 0.3438735 | 0.5371901 |
| 0.451791 | 0.410468 | 0.287879 | | 0.246212 | | 0.25 | 0.3448276 | 0.5454546 |
| 0.587879 | 0.521212 | | | | | 0.3 | 0.3 | |
| 0.403162 | 0.379447 | 0.307692 | 0.277972 | 0.333333 | 0.304545 | 0.149351 | 0.1688312 | |
| 0.507576 | 0.473485 | 0.331169 | 0.363636 | 0.377622 | 0.304545 | 0.173913 | 0.3636364 | 0.4380165 |
| 0.368984 | 0.339572 | 0.291667 | 0.242424 | 0.389611 | 0.318182 | 0.383838 | 0.2348485 | 0.3232323 |
| 0.407625 | 0.404692 | 0.352273 | 0.310606 | 0.329545 | 0.224242 | 0.162879 | 0.2597403 | |
| 0.340909 | 0.329545 | 0.306818 | 0.227273 | 0.375 | 0.318182 | 0.203463 | 0.3441558 | |
| 0.356061 | 0.329545 | 0.276515 | 0.19697 | 0.306818 | | 0.227273 | 0.3441558 | |
| 0.397727 | 0.371212 | 0.356061 | 0.299242 | 0.276515 | | 0.181818 | 0.474026 | |
| 0.377005 | 0.406417 | 0.375 | 0.401515 | 0.348485 | 0.354545 | 0.318182 | 0.3479624 | 0.2 |
| 0.378299 | 0.410557 | 0.367424 | 0.393939 | 0.382576 | 0.371212 | 0.376176 | 0.3333333 | |
| 0.393939 | 0.443182 | 0.467532 | 0.461039 | 0.375 | 0.35 | 0.367965 | 0.3097643 | |
| 0.303303 | 0.314394 | 0.314394 | 0.340909 | 0.461039 | | 0.369906 | 0.2857143 | |
| 0.478788 | 0.545455 | | | 0.32197 | 0.304545 | 0.337662 | 0.3 | |
| 0.386364 | 0.420455 | 0.383117 | 0.376623 | 0.38961 | 0.277273 | 0.322727 | 0.2659933 | 0.661157 |
| 0.513369 | 0.473262 | 0.397727 | 0.378788 | 0.443182 | 0.504545 | 0.30721 | 0.5 | |
| 0.434343 | 0.410774 | 0.393939 | 0.32197 | 0.386364 | 0.618182 | 0.420063 | 0.6315579 | 0.677686 |
| 0.483957 | 0.497326 | 0.454545 | 0.397727 | 0.462121 | 0.575758 | 0.479798 | 0.5416667 | 0.6868687 |
| 0.398396 | 0.411765 | 0.386364 | 0.367424 | 0.386364 | 0.672727 | 0.435606 | 0.5189394 | 0.414141 |
| 0.587121 | 0.575758 | 0.575758 | 0.549242 | 0.484848 | | 0.545455 | 0.7207792 | |
| 0.537433 | 0.508802 | 0.583333 | 0.579545 | 0.530303 | 0.745455 | 0.714286 | 0.6757576 | 0.6363636 |
| | | | | | | 0.717868 | | |

FIG. 18G

| | | | | | | | |
|---|---|---|---|---|---|---|---|
| 0.454545 | 0.284585 | 0.508021 | 0 | 0.003953 | 0.004545 | 0.0649351 | 0.134387 | 0.13369 |
| 0.4043887 | 0.291375 | 0.415978 | 0.003953 | 0 | 0 | 0.0867769 | 0.222571 | 0.181818 |
| 0.4 | 0.227273 | 0.515152 | 0.004545 | 0 | 0 | 0.0714286 | 0.022727 | 0.157576 |
| 0.2556818 | 0.150198 | 0.371542 | 0.0064935 | 0.086777 | 0.071429 | 0 | 0.251082 | 0.090909 |
| 0.4593301 | 0.293939 | 0.484849 | 0.134387 | 0.222571 | 0.022727 | 0.2510823 | 0 | 0.340909 |
| 0.2121212 | 0.163102 | 0.254011 | 0.13369 | 0.181818 | 0.157576 | 0.0909091 | 0.340909 | 0 |
| 0.1931818 | 0.164223 | 0.184751 | 0.25974 | 0.2333333 | 0.280303 | 0.2 | 0.398268 | 0.087977 |
| 0.1628788 | 0.212121 | 0.242424 | — | 0.193182 | — | 0.1538462 | 0.37013 | 0.083333 |
| 0.2007576 | 0.234849 | 0.287879 | — | 0.125 | — | 0.1188811 | 0.422078 | 0.106061 |
| 0.2651515 | 0.344697 | 0.344697 | — | 0.287879 | — | 0.2867133 | 0.487013 | 0.208333 |
| 0.4058442 | 0.365967 | 0.497326 | 0.31405 | 0.296651 | 0.35 | 0.2134387 | 0.448276 | 0.296791 |
| 0.4431818 | 0.434018 | 0.478006 | 0.285714 | 0.269697 | 0.333333 | 0.25 | 0.480519 | 0.322581 |
| 0.3484849 | 0.300094 | 0.477273 | 0.340909 | 0.308442 | 0.345455 | 0.1818182 | 0.417508 | 0.223485 |
| 0.4356061 | 0.469697 | 0.484849 | — | 0.284091 | — | 0.2237762 | 0.506494 | 0.310606 |
| 0.2 | 0.227273 | 0.563636 | 0.295455 | 0.3 | 0.3 | 0.1428571 | 0.322727 | 0.278788 |
| 0.3333333 | 0.257053 | 0.469697 | 0.268182 | 0.230519 | 0.272727 | 0.1343874 | 0.373737 | 0.223485 |
| 0.4952978 | 0.3045468 | 0.483957 | 0.367589 | 0.354312 | 0.327273 | 0.3438735 | 0.40303 | 0.379679 |
| 0.4733542 | 0.4231988 | 0.505051 | 0.531469 | 0.438871 | 0.536364 | 0.4659091 | 0.626794 | 0.397306 |
| 0.4276094 | 0.42246 | 0.44385 | 0.481283 | 0.440771 | 0.484848 | 0.4664032 | 0.541667 | 0.355615 |
| 0.2794613 | 0.374332 | 0.229947 | 0.695187 | 0.539945 | 0.715152 | 0.687747 | 0.526515 | 0.457219 |
| 0.530303 | 0.4962212 | 0.481061 | — | 0.742424 | — | 0.8321678 | 0.5 | 0.594697 |
| 0.5705329 | 0.5954558 | 0.481283 | 0.786561 | 0.764569 | 0.75 | 0.8814229 | 0.560606 | 0.676471 |

*FIG. 18H*

| | | | | | | | |
|---|---|---|---|---|---|---|---|
| 0.25974 | — | — | — | — | — | — | — |
| 0.233333 | 0.193182 | — | 0.125 | — | 0.285714 | 0.340909 | 0.295455 |
| 0.280303 | — | — | — | — | 0.269697 | 0.308442 | 0.3 |
| 0.2 | 0.153846 | 0.118881 | 0.2867133 | — | 0.333333 | 0.345455 | 0.3 |
| 0.398268 | 0.37013 | 0.422078 | 0.487013 | 0.213439 | 0.25 | 0.181818 | 0.142857 |
| 0.087977 | 0.083333 | 0.106061 | 0.2083333 | 0.448276 | 0.480519 | 0.417508 | 0.322727 |
| 0 | 0.113636 | 0.136364 | 0.2537879 | 0.296791 | 0.322581 | 0.223485 | 0.278788 |
| 0.113636 | 0 | 0.0681818 | 0.1628788 | 0.325513 | 0.322581 | 0.264069 | 0.356061 |
| 0.136364 | 0.068182 | 0 | 0.1704545 | 0.386364 | 0.393939 | 0.37013 | 0.386364 |
| 0.253788 | 0.162879 | 0.170455 | 0 | 0.333333 | 0.325758 | 0.337662 | 0.318182 |
| 0.325513 | 0.386364 | 0.333333 | 0.4280303 | 0.42803 | 0.42803 | 0.448052 | 0.397727 |
| 0.322581 | 0.393939 | 0.325758 | 0.4280303 | 0 | 0.014663 | 0.031348 | 0.050606 | 0.05 |
| 0.264069 | 0.37013 | 0.337662 | 0.4480519 | 0.014663 | 0 | 0.038961 | 0.05303 | 0.083333 |
| 0.356061 | 0.386364 | 0.318182 | 0.3977273 | 0.031348 | 0.038961 | 0 | 0.051948 | 0.045455 |
| 0.378788 | — | — | — | 0.060606 | 0.05303 | 0.045455 | 0 |
| 0.272727 | 0.350649 | 0.279221 | 0.3896104 | 0.05 | 0.083333 | 0.075235 | 0.071429 | 0.054545 |
| 0.407625 | 0.454545 | 0.401515 | 0.344697 | 0.075235 | 0.090909 | 0.394984 | 0.371212 | 0.3 |
| 0.390152 | 0.375 | 0.329545 | 0.2651515 | 0.384615 | 0.42522 | 0.459596 | 0.397727 | 0.409091 |
| 0.340176 | 0.375 | 0.367424 | 0.3030303 | 0.441558 | 0.450758 | 0.420455 | 0.42803 | 0.436364 |
| 0.316716 | 0.299242 | 0.352273 | 0.4393939 | 0.44385 | 0.480938 | 0.643939 | 0.518939 | 0.727273 |
| 0.564394 | 0.549242 | 0.617424 | 0.5151515 | 0.593583 | 0.568915 | 0.714286 | 0.640152 | — |
| 0.58651 | 0.609848 | 0.662879 | 0.5757576 | 0.685606 | 0.693182 | 0.711599 | 0.640152 | 0.75 |
| | | | | 0.696697 | 0.697947 | | |

*FIG. 18I*

| | | | | | | |
|---|---|---|---|---|---|---|
| 0.268182 | 0.367589 | 0.531469 | 0.481283 | 0.695187 | 1 | 0.786561 |
| 0.230519 | 0.354312 | 0.438872 | 0.440771 | 0.539945 | 0.742424 | 0.764569 |
| 0.272727 | 0.327273 | 0.536364 | 0.484849 | 0.715152 | 1 | 0.75 |
| 0.134387 | 0.343874 | 0.465909 | 0.466403 | 0.687747 | 0.832168 | 0.881423 |
| 0.373737 | 0.40303 | 0.626794 | 0.541667 | 0.526515 | 0.5 | 0.560606 |
| 0.223485 | 0.379679 | 0.397306 | 0.355615 | 0.457219 | 0.594697 | 0.676471 |
| 0.272727 | 0.407625 | 0.390152 | 0.340176 | 0.316716 | 0.564394 | 0.58651 |
| 0.350649 | 0.454546 | 0.375 | 0.375 | 0.299242 | 0.549242 | 0.609848 |
| 0.279221 | 0.401515 | 0.329546 | 0.367424 | 0.352273 | 0.617424 | 0.662879 |
| 0.38961 | 0.344697 | 0.265152 | 0.30303 | 0.439394 | 0.515152 | 0.575758 |
| 0.075235 | 0.384615 | 0.441558 | 0.44385 | 0.593583 | 0.685606 | 0.69697 |
| 0.090909 | 0.42522 | 0.450758 | 0.480938 | 0.568915 | 0.693182 | 0.697947 |
| 0.075235 | 0.394984 | 0.459596 | 0.420455 | 0.643939 | 0.714286 | 0.711599 |
| 0.071429 | 0.371212 | 0.397727 | 0.42803 | 0.518939 | 0.640152 | 0.640152 |
| 0.054545 | 0.3 | 0.409091 | 0.436364 | 0.727273 | 1 | 0.75 |
| 0 | 0.363636 | 0.444444 | 0.481061 | 0.674242 | 0.798701 | 0.786834 |
| 0.363636 | 0 | 0.109718 | 0.21123 | 0.553476 | 0.458333 | 0.509091 |
| 0.444444 | 0.109718 | 0 | 0.161616 | 0.525253 | 0.431818 | 0.492163 |
| 0.481061 | 0.21123 | 0.161616 | 0 | 0.406417 | 0.401515 | 0.385027 |
| 0.674242 | 0.553476 | 0.525253 | 0.406417 | 0 | 0.386364 | 0.251337 |
| 0.798701 | 0.458333 | 0.431818 | 0.401515 | 0.386364 | 0 | 0.060606 |
| 0.786834 | 0.509091 | 0.492163 | 0.385027 | 0.251337 | 0.060606 | 0 |

FIG. 18J

| FIG. 19A | FIG. 19B | FIG. 19C | FIG. 19D | FIG. 19E |
|---|---|---|---|---|
| FIG. 19F | FIG. 19G | FIG. 19H | FIG. 19I | FIG. 19J |

Table 12: Permuted normalized intensity matrix for five Antigen 39 Data Sets

|  | X1.17 | X1.55 | X1.16 | X1.11 | X1.12 | X1.63 |
|---|---|---|---|---|---|---|
| X1.17 | 1 | 0.9651125 | 1.37807 | 1.130158 | 0.896525 | 2.607947 |
| X1.55 | 1.048844 | 1 | 1.459081 | 1.262885 | 0.905832 | 2.544423 |
| X1.16 | 0.901348 | 0.808084 | 1 | 0.938704 | 0.7052 | 4 |
| X1.11 | 0.96614 | 0.8362154 | 1.130326 | 1 | 0.781803 | 4 |
| X1.12 | 1.167806 | 1.0646999 | 1.686484 | 1.313952 | 1 | 2.530324 |
| X1.63 | 1.574493 | 1.4899695 | 4 | 3.208486 | 1.280958 | 1 |
| X1.21 | 0.77861 | 0.7444843 |  | 0.75188 | 0.784231 | 0.733427 |
| X2.12 | 1.013234 | 1.0628115 |  | 1.1388836 | 0.978423 | 1.23513 |
| X2.38 | 1 |  |  |  | 1.623016 | 1 |
| X2.35 | 1 |  |  |  | 1.752641 | 1 |
| X2.1 | 1 |  |  |  | 1.620489 | 1 |
| X1.66 | 4 | 3.9264078 | 4 | 4 | 2.075569 | 4 |
| X1.1 | 4 | 4 | 4 | 4 | 3.474725 | 4 |
| X1.8 | 3.741761 | 3.7041602 | 4 | 4 | 2.810275 | 4 |
| X1.30 | 1 |  |  |  |  | 1 |
| X1.38 | 1 |  |  |  |  | 1 |
| X1.3 | 4 | 4 | 2.25138 | 2.296448 |  | 4 |
| X1.32 | 2.328517 | 2.3868059 |  | 1.430483 | 1.826512 | 2.163611 |

FIG. 19B

| X1.21 | X2.12 | X2.38 | X2.35 | X2.1 | X1.66 | X1.1 | X1.8 | X1.30 |
|---|---|---|---|---|---|---|---|---|
| 1.594901 | 0.910556 | --- | --- | --- | 4 | 4 | 4 | --- |
| 1.583428 | 0.927823 | --- | --- | --- | 4 | 4 | 4 | --- |
| --- | 1 | 0.980061 | --- | --- | 4 | 4 | 4 | 4 |
| 1.362722 | 1.068258 | 0.970305 | 2.884091 | 4 | 4 | 4 | 4 | 4 |
| 2.019656 | 0.84255 | --- | --- | 3.729506 | 4 | 4 | 4 | 4 |
| 1 | 0.890301 | 0.908273 | 2.729021 | 4 | --- | 2.923748 | 2.815508 | 4 |
| 1.379156 | 1 | 0.785096 | 3.121894 | 4 | --- | 3.82878 | 4 | 4 |
| 1.404098 | 1.561497 | 1 | 4 | 4 | --- | --- | --- | --- |
| 1.79145 | 1.809159 | 1.126746 | 4 | --- | --- | --- | --- | --- |
| 1.325535 | 1.496373 | 1.08473 | 4 | --- | 1 | 1.403866 | 1.8461017 | --- |
| --- | 4 | --- | --- | 4 | 0.85984 | 1 | 1.7689079 | 0.8403194 |
| 2.87 | 4 | --- | --- | 4 | 0.691251 | 0.785324 | 1 | 1.1007984 |
| --- | --- | --- | --- | --- | 1 | --- | 0.9161554 | --- |
| 3.691659 | 4 | 3.668437 | 4 | 4 | --- | --- | 1.5235174 | 0.9610778 |
| 3.588115 | 4 | 3.740418 | 4 | 4 | 4 | 4 | 2.5217773 | --- |
| 2.225438 | 4 | 3.380469 | 4 | 4 | --- | 0.437462 | 0.8134687 | --- |

FIG. 19C

| X1.38 | X1.3 | X1.32 | X1.57 | X1.61 | X1.23 | X2.28.33 | X1.24 | X2.34 |
|---|---|---|---|---|---|---|---|---|
| - | - | 4 | 4 | 3.096923 | 0.662774 | 3.310347 | 4 | 4 |
| - | 4 | 4 | 4 | 3.932276 | 0.825455 | 3.456263 | 4 | 4 |
| 4 | 4 | 4 | 4 | 3.417463 | 0.734628 | | 4 | - |
| 4 | 4 | 4 | 4 | 3.312524 | 0.618529 | 3.1593603 | 4 | 4 |
| - | 4 | 4 | 4 | 3.937798 | 1.135 | 3.8436887 | 4 | 3.871331 |
| 4 | 4 | 4 | 2.993355 | 1.814385 | 0.688923 | 4 | 2.953892 | 4 |
| 4 | 4 | 3.723195 | - | 3.046192 | - | 2.824371 | 4 | 3.619085 |
| 4 | 4 | 4 | - | 2.205113 | - | 3.2639081 | 4 | 3.475327 |
| 4 | 4 | 4 | - | 1.735533 | - | | - | 2.17793 |
| 4 | 4 | 4 | - | 1.432524 | - | | - | 1.899281 |
| 4 | 4 | 4 | - | 1.802071 | 0.840741 | | - | 1.6883 |
| 4 | 4 | 4 | 2.697465 | 3.246133 | 0.246739 | | 4 | 4 |
| 0.8641975 | 3.031368 | 1.305792 | 2.697465 | 1.784365 | 0.246739 | 2.8149254 | 3.127155 | 4 |
| 0.8721341 | 4 | 1.239211 | 3.493548 | 2.585443 | 0.424696 | 2.8149254 | 3.791865 | 4 |
| 1 | 2.477823 | 1.082171 | 4 | 3.342466 | - | | 4 | 4 |
| 1.3783962 | 1 | 1.197008 | 2.968526 | 2.996146 | 0.991266 | 3.0189519 | 2.588295 | 1.358201 |
| 1.0189761 | 0.904798 | 1 | - | 1.662368 | - | 3.0231108 | 4 | 2.736859 |
| | | | | 2.161708 | | | | 3.121027 |

FIG. 19D

| X2.2 | X2.7 | X2.21 | X2.31 | X1.31 | X2.17 | X1.46 | X2.2.C5 | X1.65 |
|---|---|---|---|---|---|---|---|---|
| 3.595564 | -- | -- | | | | | | |
| 3.454404 | -- | -- | | | 3.854953 | 3.661638 | -- | 4 |
| -- | -- | -- | | 3.83587 | 3.866 | 3.501094 | -- | 4 |
| -- | -- | -- | | 4 | -- | 4 | | 4 |
| 3.843137 | -- | 4 | 1.6338994 | 3.898883 | 3.973988 | 3.6375 | 2.917652 | 4 |
| 4 | -- | -- | | 3.501014 | 4 | 3.4067 | | 4 |
| 2.995907 | 3.325587 | 4 | 1.33778985 | 3.334988 | 3.049286 | 1.695 | 2.748884 | -- |
| 3.051341 | 3.374092 | 4 | 1.1194397 | 3.329442 | 3.552753 | 2.436098 | 3.36018 | -- |
| 3.175417 | 2.944203 | 4 | 1.3167289 | 3.67389 | 4 | 4 | 3.775016 | -- |
| 2.638511 | 2.228722 | 4 | 1.272587 | 3.38724 | 4 | 4 | 3.572644 | -- |
| 2.423343 | 2.176043 | 4 | 1.16025561 | 2.19415 | 2.494603 | | 1.941085 | -- |
| -- | -- | -- | | | | | | |
| 0.897731 | -- | -- | | 3.551546 | -- | 3.489968 | -- | 3.940741 |
| -- | -- | -- | | 3.591033 | 4 | 3.67602 | -- | 3.270109 |
| -- | -- | -- | | | -- | -- | -- | 3.428438 |
| 0.415839 | 0.950766 | 4 | 1.010222 | 3.462784 | 4 | -- | 4 | -- |
| 0.434696 | 1.051501 | 4 | 1.0684126 | 3.349408 | 4 | 3.508983 | 4 | 1.68559 |
| 0.357227 | 0.956188 | 4 | 1.0886855 | 3.500322 | 3.679941 | 2.7725 | 4 | -- |

FIG. 19E

| X1.29 | X1.53 | X1.59 | X1.13 | X2.2A12 | BB1 | BB |
|---|---|---|---|---|---|---|
| 3.002964 | 4 |  | 4 | 1.392731 |  | 1 |
| 2.945327 | 4 |  | 4 | 1.358484 |  | 1 |
|  | 4 |  |  |  |  | 1 |
| 4 | 4 | 4 | 4 | 1 |  | 1 |
| 2.967321 | 4 | 4 | 4 | 2.228333 | 2.084091 | 1 |
| 3.091552 | 4 | 4 | 4 | 1.64 |  | 1 |
| 1.143198 | 4 | 4 | 4 | 2 | 2.089161 | 1 |
| 1.436973 | 4 | 4 | 4 | 2.152856 | 1.895186 | 1 |
|  |  |  | 4 | 3.7199 | 2.046086 | 1 |
|  |  |  | 4 | 3.588442 | 1.552817 | 1 |
| 3.362913 | 4 |  | 4 | 3.023594 | 1.73391 | 1 |
|  | 4 |  | 4 | 1 |  | 1 |
|  | 4 | 4 | 4 |  |  | 1 |
| 3.707424 | 2.546397 | 2.4158 | 4 | 0.728455 | 1.365755 | 1 |
|  | 4 |  | 4 | 0.882487 | 1.319293 | 1 |
| 1.721078 | 4 |  | 4 | 0.921469 | 1.300226 | 1 |

| | 1 | 2 | 3 | 4 | 5 | 6 |
|---|---|---|---|---|---|---|
| X1.57 | 4 | 4 | 4 | 4 | 4 | 4 |
| X1.61 | 4 | 4 | 4 | 4 | 4 | 4 |
| X1.23 | 4 | 4 | 4 | 4 | 4 | 4 |
| X2.28.33 | 4 | 4 | | 4 | 4 | 4 |
| X1.24 | 2.787946 | 2.6123382 | 4 | 2.25417 | 2.52821 | 4 |
| X2.34 | 3.833606 | 3.6748235 | | 3.141807 | 3.271031 | 4 |
| X2.2 | 4 | 4 | 4 | | | |
| X2.7 | | | | | 2.980952 | |
| X2.21 | | | | | 4 | 4 |
| X2.31 | | | | | 2.894347 | |
| X1.31 | 3.327381 | 3.27741555 | 4 | 3.24812 | 3.393142 | 4 |
| X2.17 | 4 | 4 | 4 | | 3.937524 | 4 |
| X1.46 | 3.958818 | 4 | 4 | 4 | 3.717882 | 4 |
| X2.2.C5 | | | | | 2.93221 | |
| X1.65 | 4 | 4 | 4 | 4 | 4 | 4 |
| X1.29 | 3.948635 | 3.8942264 | 4 | 4 | 3.387881 | 4 |
| X1.53 | 3.09375 | 2.9559041 | 1.773885 | 1.8052 | 3.47761 | 4 |
| X1.59 | | | | 1.355157 | 4 | |
| X1.13 | 1.965244 | 2.0579801 | | 2.763158 | 3.011586 | 2.188999 |
| X2.2A12 | 0.6811944 | 0.646616 | | 0.75188 | 1.684906 | 0.5811 |
| BB1 | | | | | 0.785714 | |
| BB | 0.711423 | 0.63553383 | 1.131868 | 0.985745 | 0.588269 | 1.101966 |

| | | | | | | | |
|---|---|---|---|---|---|---|---|
| 3.759146 | 4 | -- | -- | -- | -- | 4 | 4 |
| -- | 1.461825 | 2.902623 | -- | -- | -- | 4 | 4 |
| 3.042023 | 3.319118 | 2.198091 | 4 | -- | 3.826655 | 4 | 4 |
| 3.472877 | 3.911001 | 2.699859 | 4 | 4 | 4 | 2.464072 | 3.493869 |
| 2.171245 | 3.697021 | 2.757579 | 4 | 4 | 2.021745 | 2.805183 | 1.284431 |
| 2.952158 | 3.872801 | 2.650477 | 4 | 4 | 1.683014 | -- | -- |
| 2.286375 | 2.863864 | 2.263142 | 4 | -- | -- | -- | -- |
| 3.261971 | 3.397186 | 2.962157 | 4 | -- | -- | -- | -- |
| 3.688259 | 3.826992 | 2.53483 | 4 | 4 | 4 | 3.455882 | -- |
| 4 | 4 | -- | 4 | -- | -- | 4 | -- |
| 2.532361 | 2.939858 | 1.916265 | 4 | -- | -- | 4 | -- |
| -- | -- | -- | 4 | 4 | 4 | 4 | -- |
| 3.029824 | 3.236293 | 1.195034 | 4 | 4 | -- | 3.335465 | 0.920159 |
| 3.561241 | -- | 1.169345 | 4 | 4 | -- | 4 | 1.808383 |
| 2.580926 | 2.780956 | 1.06997 | 4 | 4 | 1.264695 | 2.973262 | -- |
| 1.912793 | 1.744355 | 3.415129 | 1.755 | 3.435 | 0.605293 | 1.122994 | -- |
| 0.726331 | 0.95471 | 0.74775 | 1.655 | 3.2425 | 0.716591 | -- | -- |
| 0.892091 | 0.703944 | 0.667853 | -- | -- | 0.768045 | 1.181989 | 0.809381 |

FIG. 19H

| | | | | | | | |
|---|---|---|---|---|---|---|---|
| 4 | 4 | | | | | | |
| | | 0.826067 | 1 | | | 1.567721 | |
| 1.2451499 | 2.491709 | | 1.331091 | 0.799296 | | 1.158265 | 2.520667 |
| 3.0925346 | 3.169864 | 0.980105 | 1.164441 | 0.68997 | | 1.065108 | |
| | | | | 1 | 2.5 | | |
| 2.2826079 | 1.864045 | | | | | 4 | 4 |
| 2.7621328 | 2.657958 | 0.825274 | 0.767361 | 1.135 | 0.6696375 | | |
| | | | 1.586444 | | 2.8448755 | 4 | 3 |
| 3.5666355 | 3.996757 | | 1.636573 | | 4 | | 2.637798 |
| 4 | 3.18422 | | 1.35743 | | | | 1.371307 |
| | | | 1.146628 | | | | 1.650136 |
| | | | 2.138612 | | | | |
| 4 | 4 | 3.553198 | 3.928413 | 0.601325 | 2.2683795 | 2.9725 | 1.032825 |
| 4 | 3.147407 | | 3.491564 | | 4 | | 3.573805 |
| | | | | 0.663743 | | | 3.47792 |
| 4 | 4 | | 3.031764 | | | | |
| | | | 3.398035 | 1.135 | 4 | 4 | 2.788713 |
| 2.7791005 | 1.50321 | 2.643794 | 1.213454 | 0.445973 | | | 4 |
| 3.4237213 | 1.796422 | 3.360341 | 1.35734 | 0.836096 | 0.5734755 | 1.780617 | 2.825636 |
| 4 | 1.989824 | | 1.144582 | | | 2.1175 | 1.402976 |
| 1.4451751 | 1.41679 | | 1.448555 | | 1.0567297 | 1.83 | 2.890981 |
| | | | 1.763113 | 1.3316658 | | 1.22 | 2.620535 |
| 1.8345258 | 1.164738 | | 0.702435 | | | | 0.838863 |
| 1.2634811 | 1.037719 | 0.862406 | 0.554119 | 1.135 | 0.7741951 | 0.924565 | 2.25886 |

FIG. 19I

| | | | | | | | | |
|---|---|---|---|---|---|---|---|---|
| 3.124079 | 1.579843 | 1.821012 | 2.2912864 | | | | | 4 |
| | | | | | | | | 4 |
| 2.113161 | | | | 3.342988 | 4 | 4 | | 4 |
| | | | | | 4 | 4 | | |
| 1.34891 | 1.356171 | | 4 | 2.785 | 4 | 4 | | 4 |
| 1 | 1.302846 | | 0.9121071 | 2.951482 | 3.261423 | 3.086901 | 3.137096 | |
| 1.322912 | 1 | | 1.087843 | 2.300417 | 2.884672 | 1.97943 | 2.971805 | |
| 1.960858 | 1.242287 | | 1.2072549 | 3.147871 | 3.899956 | | 3.746235 | |
| 1.678114 | 1.609188 | | 1.5525206 | 3.526345 | 4 | | 3.910644 | |
| 3.079157 | 3.781592 | | 2.9941634 | 3.366771 | 3.146926 | | 3.238294 | |
| 3.261713 | 4 | | 2.6701065 | 1 | 1.008111 | 1.011535 | 1.0284 | 0.950993 |
| 2.366263 | | | | 0.887723 | 1 | 0.879808 | 1.009463 | |
| 3.444434 | 3.6033357 | | 1.7627368 | 0.932837 | 0.925476 | 1 | | 0.852339 |
| | | | | 0.916792 | 0.946539 | 1.10507 | | |
| | | | | 1.153145 | | | | |
| 2.539335 | | | | 1.934691 | 1.71762 | 1.624158 | | 1.657171 |
| 3.016718 | 2.496696 | | 0.695616 | 1.416329 | 4 | 2.877237 | | 1.47698 |
| 2.768431 | 2.306107 | 4 | 0.6871665 | 1.350703 | 3.99544 | | 4 | |
| 1.858709 | 2.158281 | 4 | 0.579743 | 1.022936 | 3.053514 | 1.03 | 4 | |
| 0.616038 | 0.969702 | 4 | 1.0493629 | 1.816251 | 2.426369 | 1 | 4 | |
| 0.633017 | 0.987009 | 2.58 | 0.6532861 | 0.773266 | 0.930468 | | 1.162466 | |
| 0.481228 | 0.977662 | 2.58 | 0.624686 | 0.763504 | 0.863749 | 0.976323 | 1.066436 | |

FIG. 19J

| | | | | | |
|---|---|---|---|---|---|
| 1 | 1 | 1 | 1 | 1 | 1 |
| | | | | | 4 |
| 1.779507 | 1.947817 | 3.896341 | 4 | 2.802277 | 4 |
| | | 2.23 | | | 4 |
| | | | | 3.4625 | 4 |
| 1.516716 | 1.859358 | 4 | 4 | 1.652182 | 4 |
| 1.355045 | 1.897631 | 4 | 4 | 1.310152 | 4 |
| 1.207576 | 1.915562 | 4 | 4 | | |
| 1.253208 | 2.771361 | 4 | 4 | | |
| 1.398385 | 2.462318 | 1.993775 | 1.432813 | 1.498962 | |
| | 2.371667 | 3 | 3 | | |
| 2.066465 | 3.105769 | 4 | 4 | 0.714476 | |
| 2.06812 | | 4 | 4 | 1.519393 | |
| | 1.9175 | | | | |
| 2.010724 | 4 | 4 | 4 | 2.56 | |
| | | | 4 | 2.233301 | |
| 1.848485 | 2.286652 | 1.162879 | 1 | 3.143646 | |
| | 2.5 | 1.111111 | 0.942346 | 1 | |
| 1.573016 | 4 | 1 | 1 | 0.967798 | |
| 1.554286 | 1.988374 | 2.581043 | 0.812551 | 0.458535 | |
| 1.305062 | 1 | 1.75 | 4 | 0.381764 | |
| 1 | 1.114286 | 1.275304 | 1.32 | | |
| 1 | 1.048304 | 1.245074 | 1.107506 | 1.216875 | 1.007085 |

FIG. 20A

Table 13: Permuted Average Dissimilarity matrix for Antigen 39 Expt.1

| | X1.21 | X1.12 | X1.63 | X1.17 | X1.55 | X2.12.93 | X1.32 | X1.1 |
|---|---|---|---|---|---|---|---|---|
| X1.21 | 0 | 0.186869 | 0.20202 | 0.227273 | 0.20202 | 0.161616 | 0.449495 | 0.676768 |
| X1.12 | 0.186869 | 0 | 0.015152 | 0.040404 | 0.025253 | 0.065657 | 0.363636 | 0.550505 |
| X1.63 | 0.20202 | 0.015152 | 0 | 0.035354 | 0.030303 | 0.070707 | 0.368687 | 0.535354 |
| X1.17 | 0.227273 | 0.040404 | 0.035354 | 0 | 0.025253 | 0.065657 | 0.393939 | 0.510101 |
| X1.55 | 0.20202 | 0.025253 | 0.030303 | 0.025253 | 0 | 0.040404 | 0.368687 | 0.535354 |
| X2.12.93 | 0.161616 | 0.065657 | 0.070707 | 0.065657 | 0.040404 | 0 | 0.378788 | 0.555556 |
| X1.32 | 0.449495 | 0.363636 | 0.368687 | 0.393939 | 0.368687 | 0.378788 | 0 | 0.227273 |
| X1.1 | 0.676768 | 0.550505 | 0.535354 | 0.510101 | 0.535354 | 0.555556 | 0.227273 | 0 |
| X2.28.33 | 0.550505 | 0.404040 | 0.388889 | 0.363636 | 0.388889 | 0.409091 | 0.373737 | 0.146465 |
| X2.34.39 | 0.540404 | 0.444444 | 0.449495 | 0.414141 | 0.419192 | 0.419192 | 0.272727 | 0.136364 |
| X2.20.51 | 0.489899 | 0.515152 | 0.520202 | 0.484848 | 0.489899 | 0.449495 | 0.303030 | 0.186869 |
| X1.46 | 0.449495 | 0.525253 | 0.530303 | 0.505051 | 0.5 | 0.459596 | 0.494949 | 0.409091 |
| X1.31 | 0.469697 | 0.530303 | 0.530303 | 0.494949 | 0.5 | 0.479798 | 0.515152 | 0.409091 |
| X2.17.4 | 0.474748 | 0.489899 | 0.535354 | 0.5 | 0.505051 | 0.484848 | 0.520202 | 0.404040 |
| X1.29 | 0.434343 | 0.489899 | 0.494949 | 0.459596 | 0.464646 | 0.444444 | 0.479798 | 0.363636 |
| X1.13 | 0.520202 | 0.606061 | 0.611111 | 0.616162 | 0.601010 | 0.560606 | 0.353535 | 0.449495 |
| X2.2A12 | 0.267677 | 0.454545 | 0.469697 | 0.494949 | 0.469697 | 0.429293 | 0.444444 | 0.671717 |
| BB | 0.348485 | 0.535354 | 0.550505 | 0.575758 | 0.550505 | 0.510101 | 0.525253 | 0.752525 |

| X2.28.33 | X2.34.39 | X2.20.51 | X1.46 | X1.31 | X2.17.4 | X1.29 | X1.13 | X2.2A12 | BB |
|---|---|---|---|---|---|---|---|---|---|
| 0.550505 | 0.540404 | 0.489899 | 0.449495 | 0.469697 | 0.474747 | 0.434343 | 0.520202 | 0.267677 | 0.348485 |
| 0.40404 | 0.444444 | 0.515151 | 0.525252 | 0.525253 | 0.530303 | 0.489899 | 0.606061 | 0.454545 | 0.535354 |
| 0.388889 | 0.449495 | 0.520202 | 0.530303 | 0.530303 | 0.535353 | 0.494949 | 0.611111 | 0.469697 | 0.550505 |
| 0.363636 | 0.414141 | 0.484848 | 0.505050 | 0.494949 | 0.5 | 0.459596 | 0.616162 | 0.494949 | 0.575758 |
| 0.388889 | 0.419191 | 0.489899 | 0.5 | 0.5 | 0.505050 | 0.464646 | 0.60101 | 0.469697 | 0.550505 |
| 0.409091 | 0.419191 | 0.449495 | 0.459596 | 0.479798 | 0.484848 | 0.444444 | 0.560606 | 0.429293 | 0.510101 |
| 0.373737 | 0.272727 | 0.303030 | 0.494949 | 0.515152 | 0.520202 | 0.479798 | 0.353535 | 0.444444 | 0.525253 |
| 0.146465 | 0.136363 | 0.186868 | 0.409090 | 0.409091 | 0.404040 | 0.363636 | 0.449495 | 0.671717 | 0.752525 |
| 0 | 0.111111 | 0.202020 | 0.262626 | 0.262626 | 0.257575 | 0.217171 | 0.59596 | 0.818182 | 0.89899 |
| 0.111111 | 0 | 0.090909 | 0.272727 | 0.272727 | 0.267676 | 0.227272 | 0.484849 | 0.707071 | 0.787879 |
| 0.20202 | 0.090909 | 0 | 0.222222 | 0.222222 | 0.217171 | 0.176767 | 0.393939 | 0.616162 | 0.696697 |
| 0.262626 | 0.272727 | 0.222222 | 0 | 0.020202 | 0.025252 | 0.065656 | 0.464647 | 0.575758 | 0.656566 |
| 0.262626 | 0.272727 | 0.222222 | 0.020202 | 0 | 0.005050 | 0.045454 | 0.484849 | 0.59596 | 0.676768 |
| 0.257576 | 0.267676 | 0.217171 | 0.025252 | 0.005051 | 0 | 0.040404 | 0.489899 | 0.60101 | 0.681818 |
| 0.217172 | 0.227272 | 0.176767 | 0.065656 | 0.045455 | 0.040404 | 0 | 0.5 | 0.641414 | 0.722222 |
| 0.59596 | 0.484848 | 0.393939 | 0.464646 | 0.484848 | 0.489899 | 0.5 | 0 | 0.313131 | 0.303030 |
| 0.818182 | 0.707071 | 0.616161 | 0.575757 | 0.59596 | 0.601010 | 0.641414 | 0.313131 | 0 | 0.080808 |
| 0.89899 | 0.787878 | 0.696969 | 0.656565 | 0.676768 | 0.681818 | 0.722222 | 0.30303 | 0.080808 | 0 |

FIG. 21A

Table 14: Permuted normalized intensity matrix for Antigen 39 Expt. 1

|  | X1.21 | X1.12 | X1.63 | X1.17 | X1.55 | X2.12.93 | X1.32 | X1.1 |
|---|---|---|---|---|---|---|---|---|
| X1.21 | 1 | 0.7191358 | 0.733427 | 0.664364 | 0.764214 | 0.71955 | 3.815678 | 2.923748 |
| X1.12 | 1.921376 | 1 | 1.060649 | 0.857697 | 0.9094147 | 0.9102 | 4 | 4 |
| X1.63 | 2.019656 | 0.9927984 | 1 | 0.889333 | 0.9399833 | 0.84255 | 4 | 4 |
| X1.17 | 2.200712 | 1.1387825 | 1.215894 | 1 | 1.1117338 | 0.9348707 | 4 | 4 |
| X1.55 | 2.120442 | 1.0229534 | 1.088845 | 0.898402 | 1 | 0.9070241 | 4 | 4 |
| X2.12.93 | 2.176545 | 1.04827861 | 1.23513 | 0.862155 | 1.0646806 | 1 | 4 | 3.82878 |
| X1.32 | 2.063882 | 1.33230045 | 2.163611 | 2.160061 | 2.3213002 | 4 | 1 | 0.437462 |
| X1.1 | 4 | 4 | 4 | 4 | 4 | 4 | 1.305792 | 1 |
| X2.28.33 | 4 | 4 | 4 | 4 | 4 | 4 | 4 | 3.826655 |
| X2.34.39 | 4 | 3.8717312 | 4 | 3.667213 | 4 | 4 | 4 | 2.021745 |
| X2.20.51 | 4 | 4 | 4 | 4 | 4 | 4 | 4 | 1.683014 |
| X1.46 | 4 | 4 | 4 | 3.917636 | 4 | 4 | 3.395194 | 4 |
| X1.31 | 4 | 4 | 4 | 4 | 4 | 4 | 4 | 4 |
| X2.17.4 | 4 | 4 | 4 | 4 | 4 | 4 | 4 | 4 |
| X1.29 | 4 | 4 | 4 | 4 | 4 | 4 | 4 | 4 |
| X1.13 | 2.240786 | 2.5411523 | 2.188999 | 1.720667 | 1.9945987 | 2.2099 | 1.199153 | 1.264695 |
| X2.2A12 | 0.982801 | 0.5432099 | 0.5811 | 0.47103 | 0.764214 | 0.58835 | 1.440678 | 0.605293 |
| BB | 0.982801 | 0.5514403 | 0.596615 | 0.509697 | 0.764214 | 0.626275 | 0.98517 | 0.373264 |

| X2..28.33 | X2.34.39 | X2.20.51 | X1.46 | X1.31 | X2.17.4 | X1.29 | X1.13 | X2.2A12 | BB |
|---|---|---|---|---|---|---|---|---|---|
| 4 | 4 | 1.991815 | 1.695 | 2.004963 | 2.0985714 | 1.1431979 | 4 | | 1 |
| 4 | 4 | 3.686273 | 3.275 | 3.595534 | 3.9479762 | 1.9346426 | 4 | 1.685 | 1 |
| 4 | 4 | 4 | 3.795 | 4 | 4 | 2.1831032 | 4 | 1.64 | 1 |
| 4 | 4 | 3.595564 | 3.3232759 | 3.564858 | 4 | 2.0059271 | 4 | 2.05819 | 1 |
| 4 | 4 | 3.454404 | 3.0021882 | 3.50761 | 3.8659998 | 1.8906536 | 4 | 1.873085 | 1 |
| 4 | 4 | 2.383455 | 2.4360976 | 2.491557 | 3.1055052 | 1.4369725 | 4 | 1.832195 | 1 |
| 4 | 4 | 0.314663 | 2.7725 | 2.919355 | 3.359881 | 1.7210782 | 4 | 1.215 | 1 |
| 4 | 4 | 0.897731 | 3.53902 | 4 | 4 | 2.7258264 | 4 | 3.023593 | 1 |
| 4 | 4 | 2.113161 | 4 | 4 | 4 | 2.8022767 | 4 | 3.045024 | 1 |
| 4 | 4 | 1.307308 | 3.086901 | 2.949762 | 3.3535372 | 1.6521823 | 4 | 2.477955 | 1 |
| 4 | 4 | 1 | 1.9794304 | 2.14491 | 2.7166591 | 1.3101517 | 4 | 2.216772 | 1 |
| 4 | 4 | 2.366263 | 1 | 0.861042 | 0.9254762 | 0.7858613 | 4 | 1.9175 | 1 |
| 4 | 4 | 2.718686 | 1.025 | 1 | 1.1111905 | 0.788653 | 4 | 2.115 | 1 |
| 4 | 4 | 2.897519 | 0.8798077 | 0.836674 | 1 | 0.7144763 | 4 | 2.211538 | 1 |
| 4 | 4 | 2.539335 | 1.3916849 | 1.950361 | 1.7176201 | 1 | 1 | 2.286652 | 1 |
| 1.5225 | 3.39 | 1.280677 | 1.03 | 0.796526 | 2.6232143 | 0.4585354 | 1 | 1 | 1 |
| 1.9325 | 2.57 | 0.583699 | 1 | 0.66129 | 0.8527381 | 0.3817639 | 1.9581281 | 1 | 1 |
| 1.155 | 1.9725 | 0.360289 | 1 | 0.506204 | 0.8310714 | 0.2791692 | 0.9852217 | 1 | 1 |

FIG. 22

Table 15: Permuted Average dissimilarity matrix for Antigen 39 Expt. 2

| | CR39.1.57 | X1.61 | X1.11 | X1.8 | X1.30 | X1.38 | X1.53 | X1.3 | X1.59 | X1.24 | BB |
|---|---|---|---|---|---|---|---|---|---|---|---|
| CR39.1.57 | 0 | 0.033305785 | 0.330579 | 0.512397 | 0.512397 | 0.504132 | 0.628099 | 0.636364 | 0.53719 | 0.528926 | 0.669422 |
| X1.61 | 0.033058 | 0 | 0.363636 | 0.545455 | 0.545455 | 0.537719008 | 0.595041 | 0.603306 | 0.570248 | 0.495868 | 0.636364 |
| X1.11 | 0.330579 | 0.363636 | 0 | 0.363636 | 0.363636 | 0.3553372 | 0.661157 | 0.652893 | 0.454546 | 0.677686 | 0.818182 |
| X1.8 | 0.512397 | 0.545455 | 0.363636 | 0 | 0 | 0.008264 | 0.677686 | 0.669421 | 0.702479 | 0.545455 | 0.636364 |
| X1.30 | 0.512397 | 0.545455 | 0.363636 | 0 | 0 | 0.008264 | 0.677686 | 0.669421 | 0.702479 | 0.545455 | 0.636364 |
| X1.38 | 0.504132 | 0.537719008 | 0.3553372 | 0.008264 | 0.008264 | 0 | 0.669421 | 0.661157 | 0.694215 | 0.53719 | 0.644628 |
| X1.53 | 0.628099 | 0.595041 | 0.661157 | 0.677686 | 0.677686 | 0.669421 | 0 | 0.008264 | 0.206612 | 0.247934 | 0.157025 |
| X1.3 | 0.636364 | 0.603306 | 0.652893 | 0.669421 | 0.669421 | 0.661157 | 0.008264 | 0 | 0.198347 | 0.256198 | 0.165289 |
| X1.59 | 0.53719 | 0.570248 | 0.454546 | 0.702479 | 0.702479 | 0.694215 | 0.206612 | 0.198347 | 0 | 0.454546 | 0.363636 |
| X1.24 | 0.528926 | 0.495868 | 0.677686 | 0.545455 | 0.545455 | 0.53719 | 0.247934 | 0.256198 | 0.454546 | 0 | 0.140496 |
| BB | 0.669421 | 0.636364 | 0.818182 | 0.636364 | 0.636364 | 0.644628 | 0.157025 | 0.165289 | 0.363636 | 0.140496 | 0 |

FIG. 23

Table 16: Permuted normalized intensity matrix for Antigen 39 Expt. 2

| | CR39.1.5 7 | X1.61 | X1.11 | X1.8 | X1.30 | X1.38 | X1.53 | X1.3 | X1.59 | X1.24 | BB |
|---|---|---|---|---|---|---|---|---|---|---|---|
| CR39.1.5 7 | 1 | 1.2031963 | 4 | 4 | 4 | 4 | 4 | 4 | 4 | 1.885 | 1 |
| X1.61 | 0.890192 | 1 | 4 | 4 | 4 | 4 | 4 | 4 | 4 | 1.35 | 1 |
| X1.11 | 4 | 3.464393 | 1 | 4 | 4 | 4 | 4 | 4 | 4 | 4 | 1 |
| X1.8 | 4 | 3.0692542 | 4 | 1 | 0.840319 | 0.864198 | 4 | 4 | 4 | 4 | 1 |
| X1.30 | 4 | 3.3424658 | 4 | 0.916155 | 1 | 0.872134 | 4 | 4 | 4 | 4 | 1 |
| X1.38 | 4 | 3.8926941 | 4 | 1.523517 | 1.100798 | 1 | 4 | 4 | 4 | 4 | 1 |
| X1.53 | 2.142857 | 0.8074581 | 0.868582 | 2.674847 | 0.92016 | 1.558201 | 1 | 1 | 0.831601 | 1.2525 | 1 |
| X1.3 | 2.259062 | 0.9101979 | 0.863522 | 2.574642 | 0.961078 | 1.561728 | 1 | 1 | 0.831601 | 1.16 | 1 |
| X1.59 | 3.360341 | 1.435312 | 1.355157 | 4 | 1.808383 | 2.847443 | 1.0975 | 1.48 | 1 | 2.1175 | 1 |
| X1.24 | 0.679105 | 0.5449011 | 1.409127 | 1.715746 | 1.284431 | 1.24515 | 2.3875 | 1.987526 | 1 | 1 | 1 |
| BB | 0.837953 | 0.5616438 | 0.934358 | 0.965235 | 0.809381 | 0.744268 | 1.19 | 0.939709 | 1 | 1 | 1 |

FIG. 24A

Table 17: Permuted Average Dissimilarity matrix for Antigen 39 Expt. 3

| | X1.32 | X1.3 | X1.8 | X2.34.39 | X2.28.33 | X1.13 | X1.53 | X1.31 |
|---|---|---|---|---|---|---|---|---|
| X1.32 | 0 | 0.197861 | 0.197861 | 0.368984 | 0.379679 | 0.481283 | 0.497326 | 0.497326 |
| X1.3 | 0.19786 | 0 | 0 | 0.224599 | 0.235294 | 0.411765 | 0.406417 | 0.470588 |
| X1.8 | 0.19786 | 0 | 0 | 0.224599 | 0.235294 | 0.411765 | 0.406417 | 0.470588 |
| X2.34.39 | 0.368898 | 0.2245989 | 0.224599 | 0 | 0.010695 | 0.411765 | 0.395722 | 0.470588 |
| X2.28.33 | 0.37968 | 0.2352941 | 0.235294 | 0.010695 | 0 | 0.40107 | 0.385027 | 0.459893 |
| X1.13 | 0.48128 | 0.4117647 | 0.411765 | 0.411765 | 0.40107 | 0 | 0.037433 | 0.069519 |
| X1.53 | 0.49733 | 0.4064171 | 0.406417 | 0.395722 | 0.385027 | 0.037433 | 0 | 0.074866 |
| X1.31 | 0.49733 | 0.4705882 | 0.470588 | 0.470588 | 0.459893 | 0.069519 | 0.074866 | 0 |
| X1.55 | 0.38503 | 0.5294118 | 0.529412 | 0.40107 | 0.411765 | 0.663102 | 0.657754 | 0.593583 |
| X1.12 | 0.38503 | 0.5294118 | 0.529412 | 0.40107 | 0.411765 | 0.663102 | 0.657754 | 0.593583 |
| X1.17 | 0.38503 | 0.5294118 | 0.529412 | 0.40107 | 0.411765 | 0.663102 | 0.657754 | 0.593583 |
| X2.12.93 | 0.38503 | 0.5294118 | 0.529412 | 0.40107 | 0.411765 | 0.663102 | 0.657754 | 0.593583 |
| X1.11 | 0.37968 | 0.57754010 | 0.57754 | 0.352941 | 0.363636 | 0.614973 | 0.609626 | 0.545455 |
| X1.21 | 0.37968 | 0.57754010 | 0.57754 | 0.695187 | 0.684492 | 0.433155 | 0.449198 | 0.374332 |
| X2.2A12 | 0.4492 | 0.64705880 | 0.647059 | 0.775401 | 0.764706 | 0.363636 | 0.379679 | 0.304813 |
| BB | 0.42246 | 0.62032090 | 0.620321 | 0.57754 | 0.566845 | 0.518717 | 0.524064 | 0.459893 |
| X1.24 | | | | | | | | |

FIG. 24

| FIG. 24A | FIG. 24B |

FIG. 24B

| X1.55 | X1.12 | X1.17 | X2.12.93 | X1.11 | X1.21 | X2.2A12 | BB | X1.24 |
|---|---|---|---|---|---|---|---|---|
| 0.385027 | 0.385027 | 0.385027 | 0.385027 | 0.385027 | 0.3796791 | 0.3796791 | 0.449198 | 0.42246 |
| 0.529412 | 0.529412 | 0.529412 | 0.529412 | 0.529412 | 0.5775401 | 0.5775401 | 0.647059 | 0.620321 |
| 0.529412 | 0.529412 | 0.529412 | 0.529412 | 0.529412 | 0.5775401 | 0.5775401 | 0.647059 | 0.620321 |
| 0.401107 | 0.401107 | 0.401107 | 0.401107 | 0.401107 | 0.3529412 | 0.6951872 | 0.775401 | 0.57754 |
| 0.411765 | 0.411765 | 0.411765 | 0.411765 | 0.411765 | 0.3636364 | 0.684492 | 0.764706 | 0.566845 |
| 0.663102 | 0.663102 | 0.663102 | 0.663102 | 0.663102 | 0.6149733 | 0.4331551 | 0.363636 | 0.518717 |
| 0.657754 | 0.657754 | 0.657754 | 0.657754 | 0.657754 | 0.6096257 | 0.4491979 | 0.379679 | 0.524064 |
| 0.593583 | 0.593583 | 0.593583 | 0.593583 | 0.593583 | 0.5454546 | 0.3743316 | 0.304813 | 0.459893 |
| 0 | 0 | 0 | 0 | 0 | 0.0048128 | 0.3903743 | 0.470588 | 0.283423 |
| 0 | 0 | 0 | 0 | 0 | 0.0048128 | 0.3903743 | 0.470588 | 0.283423 |
| 0 | 0 | 0 | 0 | 0 | 0.0048128 | 0.3903743 | 0.470588 | 0.283423 |
| 0 | 0 | 0 | 0 | 0 | 0.0048128 | 0.3903743 | 0.470588 | 0.283423 |
| 0.0048128 | 0.0048128 | 0.0048128 | 0.0048128 | 0.0048128 | 0 | 0.342246 | 0.42246 | 0.235294 |
| 0.390374 | 0.390374 | 0.390374 | 0.390374 | 0.390374 | 0.342246 | 0 | 0.080214 | 0.117647 |
| 0.470588 | 0.470588 | 0.470588 | 0.470588 | 0.470588 | 0.4224599 | 0.0802139 | 0 | 0.197861 |
| 0.283422 | 0.283422 | 0.283422 | 0.283422 | 0.283422 | 0.2352941 | 0.1176471 | 0.197861 | 0 |

FIG. 25A

Table 18: Permuted normalized intensity matrix for Antigen 39 Expt. 3

| | X1.32 | X1.3 | X1.8 | X2.34.39 | X2.28.33 | X1.13 | X1.53 | X1.31 |
|---|---|---|---|---|---|---|---|---|
| X1.32 | 1 | 0.9135702 | 0.813469 | 4 | 2.046222 | 4 | 4 | 4 |
| X1.3 | 1.240172 | 1 | 0.99069 | 4 | 3.018952 | 4 | 4 | 4 |
| X1.8 | 1.239212 | 1.0941026 | 1 | 4 | 2.814925 | 4 | 4 | 4 |
| X2.34.39 | 3.865119 | 3.2850501 | 2.805184 | 4 | 1.689751 | 4 | 4 | 3.309157 |
| X2.28.33 | 4 | 4 | 3.49387 | 4 | 1 | 3.79268 | 4 | 2.685976 |
| X1.13 | 1.429534 | 1.5848397 | 2.973262 | 4 | 0.59096 | 1 | 1 | 1 |
| X1.53 | 1.184229 | 1.6210417 | 3.331551 | 4 | 0.573476 | 1 | 1 | 1 |
| X1.31 | 1.442222 | 1.5526603 | 2.911765 | 4 | 0.536759 | 1 | 1 | 1 |
| X1.55 | 4 | 4 | 4 | 4 | 2.912526 | 4 | 4 | 4 |
| X1.12 | 4 | 4 | 4 | 4 | 3.687377 | 4 | 4 | 4 |
| X1.17 | 4 | 4 | 4 | 4 | 2.620694 | 4 | 4 | 4 |
| X2.12.93 | 4 | 4 | 4 | 4 | 2.527816 | 4 | 4 | 4 |
| X1.11 | 4 | 4 | 4 | 4 | 3.15936 | 4 | 4 | 4 |
| X1.21 | 3.353907 | 4 | 2.815508 | 4 | 1.648742 | 4 | 4 | 4 |
| X2.2A12 | 1.488746 | 1.5486378 | 1.122995 | 4 | 0.730832 | 1.785 | 3.175 | 1.345 |
| BB | 0.845878 | 0.8447115 | 0.622995 | 4 | 0.39339 | 1 | 1 | 1 |
| X1.24 | 2.36 | 1.9951282 | 1.676471 | 4 | 0.669638 | 2.23 | 4 | 1.57 |

FIG. 25

| FIG. 25A | FIG. 25B |

FIG. 25B

| X1.55 | X1.12 | X1.17 | X2.12.93 | X1.11 | X1.21 | X2.2A12 | BB | X1.24 |
|---|---|---|---|---|---|---|---|---|
| 2.452312 | 1.159565 | 2.496973 | 4 | 1.430483 | 1.7711864 | 0.8474576 | 1 | 4 |
| 4 | 4 | 4 | 4 | 4 | 3.5219124 | 0.9282869 | 1 | 4 |
| 4 | 3.69821 | 4 | 4 | 4 | 2.87 | 1 | 1 | 4 |
| 3.349647 | 2.850167 | 4 | 2.814212 | 3.141807 | 2.9610154 | 1.0716228 | 1 | 4 |
| 4 | 4 | 4 | 4 | 4 | 3.5182927 | 0.8506098 | 1 | 4 |
| 2.121362 | 2.493606 | 2.209821 | 2.382846 | 2.763158 | 2.135 | 1 | 1 | 1.83 |
| 2.071105 | 2.746803 | 2.1875 | 2.472587 | 2.890977 | 2.28 | 1 | 1 | 1.925 |
| 1.822467 | 2.306905 | 1.982143 | 2.191557 | 2.496241 | 1.96 | 1 | 1 | 1.945 |
| 1 | 0.902155 | 1.111362 | 0.948623 | 1.050094 | 1.0464135 | 0.8438819 | 1 | 4 |
| 1.092422 | 1 | 1.227679 | 1.067439 | 1.090226 | 1.045 | 1 | 1 | 4 |
| 0.906063 | 0.823994 | 1 | 0.886241 | 0.932331 | 0.9890909 | 0.7272727 | 1 | 4 |
| 1.060942 | 0.925588 | 1.164312 | 1 | 1.138836 | 1.1043956 | 0.6263736 | 1 | 4 |
| 0.976038 | 0.897698 | 1.09375 | 0.9800061 | 1 | 1 | 1 | 1 | 4 |
| 0.724755 | 0.662404 | 0.892857 | 0.819472 | 0.75188 | 1 | 1 | 1 | 4 |
| 0.529018 | 0.511509 | 0.892857 | 0.644715 | 0.75188 | 1 | 1 | 1 | 1.22 |
| 0.529018 | 0.511509 | 0.892857 | 0.606929 | 0.75188 | 1 | 1 | 1 | 1 |
| 1.224676 | 1.340154 | 1.575893 | 1.461825 | 1.353384 | 1 | 1 | 1 | 1 |

FIG. 26A

Table 19: Permuted Average Dissimilarity matrix for Antigen 39 Expt. 4

| | X1.17 | X1.16 | X1.55 | X1.11 | X1.12 | X1.63 | X1.66 | X1.8 | X1.1 |
|---|---|---|---|---|---|---|---|---|---|
| X1.17 | | 0 | 0 | 0 | 0.013636 | 0.25 | 0.359091 | 0.395455 | 0.422727 |
| X1.16 | 0 | | 0 | 0 | 0.013636 | 0.25 | 0.359091 | 0.395455 | 0.422727 |
| X1.55 | 0 | 0 | | 0 | 0.013636 | 0.25 | 0.359091 | 0.395455 | 0.422727 |
| X1.11 | 0 | 0 | 0 | | 0.013636 | 0.25 | 0.359091 | 0.395455 | 0.422727 |
| X1.12 | 0.013636 | 0.013636 | 0.013636 | 0.013636 | | 0.236364 | 0.345455 | 0.381818 | 0.409091 |
| X1.63 | 0.25 | 0.25 | 0.25 | 0.25 | 0.236364 | | 0.272727 | 0.263636 | 0.272727 |
| X1.66 | 0.359091 | 0.359091 | 0.359091 | 0.359091 | 0.345455 | 0.272727 | | 0.045455 | 0.063636 |
| X1.8 | 0.395455 | 0.395455 | 0.395455 | 0.395455 | 0.381818 | 0.263636 | 0.045455 | | 0.054545 |
| X1.1 | 0.422727 | 0.422727 | 0.422727 | 0.422727 | 0.409091 | 0.272727 | 0.063636 | 0.054545 | 0 |
| X1.57 | 0.4 | 0.4 | 0.4 | 0.4 | 0.386364 | 0.25 | 0.304545 | 0.304545 | 0.25 |
| X1.61 | 0.4 | 0.4 | 0.4 | 0.4 | 0.386364 | 0.25 | 0.304545 | 0.304545 | 0.25 |
| X1.24 | 0.4 | 0.4 | 0.4 | 0.4 | 0.386364 | 0.25 | 0.304545 | 0.304545 | 0.25 |
| X1.23 | 0.4 | 0.4 | 0.4 | 0.4 | 0.386364 | 0.25 | 0.304545 | 0.304545 | 0.25 |
| X1.31 | 0.413636 | 0.413636 | 0.413636 | 0.413636 | 0.4 | 0.327273 | 0.318182 | 0.363636 | 0.336364 |
| X1.46 | 0.413636 | 0.413636 | 0.413636 | 0.413636 | 0.4 | 0.327273 | 0.318182 | 0.363636 | 0.336364 |
| X1.65 | 0.4 | 0.4 | 0.4 | 0.4 | 0.386364 | 0.313636 | 0.304545 | 0.35 | 0.322727 |
| X1.29 | 0.35 | 0.35 | 0.35 | 0.35 | 0.336364 | 0.263636 | 0.254545 | 0.3 | 0.272727 |
| X1.53 | 0.422727 | 0.422727 | 0.422727 | 0.422727 | 0.409091 | 0.427273 | 0.481818 | 0.481818 | 0.427273 |
| X1.3 | 0.404545 | 0.404545 | 0.404545 | 0.404545 | 0.390909 | 0.327273 | 0.381818 | 0.381818 | 0.327273 |
| BB | 0.604545 | 0.604545 | 0.604545 | 0.604545 | 0.618182 | 0.709091 | 0.709091 | 0.7 | 0.7 |

| X1.57 | X1.61 | X1.24 | X1.23 | X1.31 | X1.46 | X1.65 | X1.29 | X1.53 | X1.3 | BB |
|---|---|---|---|---|---|---|---|---|---|---|
| 0.4 | 0.4 | 0.4 | 0.4 | 0.4136364 | 0.4136364 | 0.4 | 0.35 | 0.422727 | 0.404546 | 0.604546 |
| 0.4 | 0.4 | 0.4 | 0.4 | 0.4136364 | 0.4136364 | 0.4 | 0.35 | 0.422727 | 0.404546 | 0.604546 |
| 0.4 | 0.4 | 0.4 | 0.4 | 0.4136364 | 0.4136364 | 0.4 | 0.35 | 0.422727 | 0.404546 | 0.604546 |
| 0.4 | 0.4 | 0.4 | 0.4 | 0.4136364 | 0.4136364 | 0.4 | 0.35 | 0.422727 | 0.404546 | 0.604546 |
| 0.386364 | 0.386364 | 0.386364 | 0.386364 | 0.4136364 | 0.4136364 | 0.4 | 0.336364 | 0.409091 | 0.390909 | 0.618182 |
| 0.25 | 0.25 | 0.25 | 0.25 | 0.3272727 | 0.3272727 | 0.3863636 | 0.263636 | 0.4272727 | 0.327273 | 0.709091 |
| 0.304546 | 0.304546 | 0.304546 | 0.304546 | 0.3181818 | 0.3181818 | 0.3045455 | 0.254545 | 0.481818 | 0.381818 | 0.709091 |
| 0.304546 | 0.304546 | 0.304546 | 0.304546 | 0.3636364 | 0.3636364 | 0.35 | 0.3 | 0.481818 | 0.381818 | 0.7 |
| 0.25 | 0.25 | 0.25 | 0.25 | 0.3363636 | 0.3363636 | 0.3227273 | 0.2727727 | 0.4272727 | 0.327273 | 0.7 |
| 0 | 0 | 0 | 0 | 0.3136364 | 0.3136364 | 0.3 | 0.25 | 0.340909 | 0.304546 | 0.704546 |
| 0 | 0 | 0 | 0 | 0.3136364 | 0.3136364 | 0.3 | 0.25 | 0.340909 | 0.304546 | 0.704546 |
| 0 | 0 | 0 | 0 | 0.3136364 | 0.3136364 | 0.3 | 0.25 | 0.340909 | 0.304546 | 0.704546 |
| 0.3136364 | 0.3136364 | 0.3136364 | 0.3136364 | 0 | 0 | 0 | 0.25 | 0.340909 | 0.304546 | 0.704546 |
| 0.3136364 | 0.3136364 | 0.3136364 | 0.3136364 | 0 | 0 | 0.0136364 | 0.0636364 | 0.327273 | 0.281818 | 0.690909 |
| 0.25 | 0.25 | 0.25 | 0.3 | 0.0136364 | 0.0136364 | 0.0136364 | 0.0636364 | 0.327273 | 0.281818 | 0.690909 |
| 0.25 | 0.25 | 0.25 | 0.25 | 0.0636364 | 0.0636364 | 0 | 0.05 | 0.313636 | 0.268182 | 0.704546 |
| 0.340909 | 0.340909 | 0.340909 | 0.340909 | 0.3272727 | 0.3272727 | 0.3136364 | 0.290909 | 0.290909 | 0.218182 | 0.754546 |
| 0.304546 | 0.304546 | 0.304546 | 0.304546 | 0.2818182 | 0.2818182 | 0.2681818 | 0.218182 | 0 | 0.1 | 0.527273 |
| 0.704546 | 0.704546 | 0.704546 | 0.704546 | 0.69090991 | 0.69090991 | 0.7045455 | 0.7545455 | 0.527273 | 0.627273 | 0 |

FIG. 27A

Table 20: Permuted normalized intensity matrix for Antigen 39 Expt. 4

| | X1.17 | X1.16 | X1.55 | X1.11 | X1.12 | X1.63 | X1.66 | X1.8 | X1.1 |
|---|---|---|---|---|---|---|---|---|---|
| X1.17 | 1 | | | | 0.726797 | 4 | 4 | 4 | 4 |
| X1.16 | 0.901348 | 1 | 0.808084 | 0.938704 | 0.7052 | 4 | 4 | 4 | 4 |
| X1.55 | 1.136769 | 1.37807 | 1 | 1.475676 | 0.792388 | 4 | 4 | 4 | 4 |
| X1.11 | 0.838531 | 1.459081 | 0.696393 | 1 | 0.665908 | 4 | 4 | 4 | 4 |
| X1.12 | 1.418043 | 1.130326 | 1.192263 | 1.537678 | 1 | 4 | 1.846102 | 1 | 4 |
| X1.63 | 2.259653 | 1.686484 | 2.039956 | 3.208486 | 1.569117 | 1 | 3.729506 | 1 | 1.403866 |
| X1.66 | 4 | 4 | 3.926408 | 4 | 2.075569 | 4 | 1 | 1 | 0.785324 |
| X1.8 | 3.483522 | 4 | 3.40832 | 4 | 1.92234 | 4 | 0.691251 | 1.846102 | 1 |
| X1.1 | 4 | 4 | 4 | 4 | 2.949449 | 4 | 0.85984 | 1.768908 | 1 |
| X1.57 | 4 | 4 | 4 | 4 | 4 | 4 | 4 | 4 | 4 |
| X1.61 | 4 | 4 | 4 | 4 | 3.716267 | 4 | 4 | 4 | 4 |
| X1.24 | 4 | 4 | 4 | 4 | 4 | 4 | 4 | 4 | 4 |
| X1.23 | 4 | 4 | 4 | 4 | 3.265661 | 4 | 4 | 4 | 4 |
| X1.31 | 4 | 4 | 4 | 4 | 3.435765 | 4 | 4 | 4 | 4 |
| X1.46 | 4 | 4 | 4 | 4 | 4 | 4 | 4 | 4 | 4 |
| X1.65 | 4 | 4 | 4 | 4 | 4 | 4 | 4 | 4 | 4 |
| X1.29 | 3.89727 | 4 | 3.788453 | 4 | 2.775761 | 4 | 4 | 4 | 4 |
| X1.53 | 4 | 1.773885 | 3.840703 | 1.65604 | 3.686028 | 4 | 4 | 4 | 4 |
| X1.3 | 4 | 2.25138 | 4 | 2.025823 | 4 | 4 | 4 | 4 | 4 |
| BB | 0.731715 | 1.131868 | 0.613383 | 1.270996 | 0.504414 | 1.607317 | 0.768045 | 1.957737 | 1.059919 |

FIG. 27

| FIG. 27A | FIG. 27B |

FIG. 27B

| X1.57 | X1.61 | X1.24 | X1.23 | X1.31 | X1.46 | X1.65 | X1.29 | X1.53 | X1.3 | BB |
|---|---|---|---|---|---|---|---|---|---|---|
| 4 | 3.09692 | 4 | 0.662774 | 4 | 4 | 4 | 4 | 4 | 4 | 1 |
| 4 | 3.41746 | 4 | 0.734628 | 4 | 4 | 4 | 4 | 4 | 4 | 1 |
| 4 | 3.93228 | 4 | 0.825455 | 4 | 4 | 4 | 4 | 4 | 4 | 1 |
| 4 | 3.16065 | 4 | 0.618529 | 4 | 4 | 4 | 4 | 4 | 4 | 1 |
| 4 | 4 | 4 | 1.135 | 4 | 4 | 4 | 4 | 4 | 4 | 1 |
| 2.993355 | 1.81439 | 2.958892 | 0.688923 | 3.002027 | 3.0183996 | 2.8892261 | 4 | 4 | 4 | 1 |
| 4 | 3.24613 | 4 | 0.840741 | 4 | 4 | 3.9407407 | 4 | 4 | 4 | 1 |
| 2.987096 | 2.09983 | 3.375595 | 0.424696 | 3.182066 | 3.6760203 | 3.4284378 | 4 | 4 | 4 | 1 |
| 2.697465 | 1.78437 | 3.127155 | 0.246739 | 3.103091 | 3.4409168 | 3.2701087 | 4 | 4 | 4 | 1 |
| 0.761941 | 1.45899 | 1.250443 | 0.799296 | 4 | 4 | 4 | 4 | 4 | 4 | 1 |
| 0.971444 | 1 | 0.96653 | 0.68997 | 4 | 4 | 4 | 4 | 4 | 4 | 1 |
| 0.980105 | 1.16444 | 1.065108 | 1.135 | 1 | 1 | 1 | 4 | 4 | 4 | 1 |
| 4 | 4 | 4 | 0.601325 | 1.004632 | 0.9809704 | 0.9509934 | 2.209272 | 4 | 4 | 1 |
| 4 | 0.98982 | 4 | 0.663743 | 1.153145 | 1 | 1 | 2.252924 | 4 | 4 | 1 |
| 4 | 4 | 4 | 1.135 | 1.135 | 1.1050696 | 0.8523392 | 2.56 | 4 | 4 | 1 |
| 4 | 4 | 4 | 0.455973 | 1.91902 | 1.8566308 | 1.6571709 | 3.466601 | 4 | 4 | 1 |
| 3.553198 | 3.39804 | 2.16435 | 0.836096 | 1.814068 | 2.8772373 | 1.4769797 | 3.143646 | 4 | 0.843462 | 1 |
| 3.14473 | 1.45622 | 2.16435 | 0.836096 | 2.221573 | 3.508983 | 1.6855895 | 3.707424 | 1.18559 | 1 | 1 |
| 3.677991 | 1.77984 | 2.604884 | 0.991266 | | | | | | | |
| 0.868859 | 0.54332 | 0.773694 | 1.135 | 0.781543 | 0.9526462 | 1 | 1.735 | 1.3575 | 1.145 | 1 |

Table 21: Permuted Average Dissimilarity matrix for Antigen 39 Expt. 5

| | X1.38 | X1.3 | X1.32 | X2.2.A12 | X2.2 | X2.31 |
|---|---|---|---|---|---|---|
| X1.38 | 0 | 0.007575758 | 0.003788 | 0.011364 | 0.090909 | 0.291667 |
| X1.3 | 0.007576 | 0 | 0.003787879 | 0.018939 | 0.098485 | 0.291667 |
| X1.32 | 0.003788 | 0.003787879 | 0 | 0.015152 | 0.094697 | 0.287879 |
| X2.2.A12 | 0.011364 | 0.018939394 | 0.015152 | 0 | 0.079545 | 0.30303 |
| X2.2 | 0.090909 | 0.098484848 | 0.094697 | 0.079545 | 0 | 0.238636 |
| X2.31 | 0.291667 | 0.291666667 | 0.287879 | 0.30303 | 0.238636 | 0 |
| X2.34 | 0.200758 | 0.208333333 | 0.204545 | 0.189394 | 0.117424 | 0.151515 |
| X2.7 | 0.181818 | 0.189393939 | 0.185606 | 0.170455 | 0.098485 | 0.162879 |
| X2.21 | 0.219697 | 0.227272727 | 0.223485 | 0.208333 | 0.136364 | 0.170455 |
| X1.61 | 0.344697 | 0.352272727 | 0.348485 | 0.333333 | 0.261364 | 0.287879 |
| X1.59 | 0.458333 | 0.465909091 | 0.462121 | 0.446697 | 0.367424 | 0.234849 |
| X1.53 | 0.477273 | 0.484848485 | 0.481061 | 0.465909 | 0.393939 | 0.261364 |
| X1.13 | 0.42803 | 0.435606061 | 0.431818 | 0.416667 | 0.359848 | 0.242424 |
| X1.21 | 0.5 | 0.492424242 | 0.496212 | 0.511364 | 0.44697 | 0.382576 |
| X1.12 | 0.507576 | 0.5 | 0.503788 | 0.518939 | 0.454545 | 0.390152 |
| X2.12 | 0.477273 | 0.469696970 | 0.473485 | 0.488636 | 0.424242 | 0.359849 |
| X2.38 | 0.465909 | 0.473484848 | 0.469697 | 0.454545 | 0.390152 | 0.356061 |
| X2.35 | 0.409091 | 0.416666667 | 0.412879 | 0.397727 | 0.325758 | 0.299242 |
| X2.1 | 0.458333 | 0.465909091 | 0.462121 | 0.454545 | 0.382576 | 0.348485 |
| X2.17 | 0.5 | 0.492424242 | 0.496212 | 0.511364 | 0.439394 | 0.42803 |
| X1.31 | 0.5 | 0.492424242 | 0.496212 | 0.511364 | 0.439394 | 0.42803 |
| X2.2.C5 | 0.492424 | 0.484848485 | 0.488636 | 0.503788 | 0.431818 | 0.397727 |
| BB1 | 0.473485 | 0.481060606 | 0.477273 | 0.462121 | 0.496212 | 0.515152 |
| BB | 0.473485 | 0.481060606 | 0.477273 | 0.462121 | 0.503788 | 0.522727 |

FIG. 28A

| FIG. 28A | FIG. 28B | FIG. 28C |

| X2.34 | X2.7 | X2.21 | X1.61 | X1.59 | X1.53 | X1.13 | X1.21 | X1.12 |
|---|---|---|---|---|---|---|---|---|
| 0.200758 | 0.181818 | 0.219697 | 0.344697 | 0.458333 | 0.477273 | 0.42803 | 0.5 | 0.5075758 |
| 0.208333 | 0.189394 | 0.227273 | 0.352273 | 0.465909 | 0.484848 | 0.435606 | 0.4924242 | 0.5 |
| 0.204545 | 0.185606 | 0.223485 | 0.348485 | 0.462121 | 0.481061 | 0.431818 | 0.4962121 | 0.5037879 |
| 0.189394 | 0.170455 | 0.208333 | 0.333333 | 0.446970 | 0.465909 | 0.416667 | 0.5113636 | 0.5189394 |
| 0.117424 | 0.098485 | 0.136364 | 0.261364 | 0.367424 | 0.393939 | 0.359848 | 0.4469697 | 0.4545455 |
| 0.151515 | 0.162879 | 0.170455 | 0.287879 | 0.234848 | 0.261364 | 0.242424 | 0.3825758 | 0.3901515 |
| 0 | 0.026515 | 0.087121 | 0.204546 | 0.325758 | 0.352273 | 0.333333 | 0.3371212 | 0.344697 |
| 0.026515 | 0 | 0.068182 | 0.193182 | 0.344697 | 0.371212 | 0.352273 | 0.3636364 | 0.3712121 |
| 0.087121 | 0.068182 | 0 | 0.125 | 0.310606 | 0.333333 | 0.306818 | 0.3333333 | 0.3333333 |
| 0.204545 | 0.193182 | 0.125 | 0 | 0.299242 | 0.359848 | 0.378788 | 0.3143939 | 0.3068182 |
| 0.325758 | 0.344697 | 0.299242 | 0.363636 | 0 | 0.026515 | 0.030303 | 0.4204545 | 0.4280303 |
| 0.352273 | 0.371212 | 0.310606 | 0.359849 | 0.026515 | 0 | 0.049242 | 0.4015152 | 0.4090909 |
| 0.333333 | 0.352273 | 0.306818 | 0.378788 | 0.030303 | 0.049242 | 0 | 0.4507576 | 0.4583333 |
| 0.371121 | 0.363636 | 0.333333 | 0.314394 | 0.420455 | 0.401515 | 0.450758 | 0 | 0.0075758 |
| 0.344697 | 0.371212 | 0.333333 | 0.306818 | 0.42803 | 0.409091 | 0.458333 | 0.0075758 | 0 |
| 0.314394 | 0.340909 | 0.310606 | 0.299242 | 0.397727 | 0.378788 | 0.42803 | 0.0227273 | 0.030303 |
| 0.280303 | 0.306818 | 0.276515 | 0.287879 | 0.363636 | 0.344697 | 0.393939 | 0.0568182 | 0.0643939 |
| 0.208333 | 0.227273 | 0.19697 | 0.246212 | 0.291667 | 0.303030 | 0.314394 | 0.1363636 | 0.1439394 |
| 0.280303 | 0.306818 | 0.276515 | 0.333333 | 0.356061 | 0.352273 | 0.363636 | 0.1401515 | 0.1477273 |
| 0.397727 | 0.393939 | 0.325758 | 0.253788 | 0.420455 | 0.401515 | 0.450758 | 0.3333333 | 0.3257576 |
| 0.397727 | 0.393939 | 0.325758 | 0.253788 | 0.420455 | 0.401515 | 0.450758 | 0.3333333 | 0.3257576 |
| 0.359848 | 0.386364 | 0.318182 | 0.284091 | 0.367424 | 0.348485 | 0.397727 | 0.280303 | 0.2727273 |
| 0.545455 | 0.549242 | 0.617424 | 0.742424 | 0.462121 | 0.481061 | 0.431818 | 0.6098485 | 0.6174242 |
| 0.55303 | 0.556818 | 0.625 | 0.75 | 0.469697 | 0.488636 | 0.439394 | 0.6174242 | 0.625 |

FIG. 28C

| X2.12 | X2.38 | X2.35 | X2.1 | X2.17 | X1.31 | X2.2.C5 | BB1 | BB |
|---|---|---|---|---|---|---|---|---|
| 0.4772727 | 0.465909 | 0.409091 | 0.458333 | 0.5 | 0.5 | 0.4924242 | 0.473485 | 0.473485 |
| 0.4696697 | 0.473485 | 0.416667 | 0.465909 | 0.492424 | 0.492424 | 0.4848485 | 0.481061 | 0.481061 |
| 0.4734849 | 0.469697 | 0.412879 | 0.462121 | 0.496212 | 0.496212 | 0.4886364 | 0.477273 | 0.477273 |
| 0.4886364 | 0.454545 | 0.397727 | 0.454545 | 0.511364 | 0.511364 | 0.5037879 | 0.462121 | 0.462121 |
| 0.4242424 | 0.390152 | 0.325758 | 0.382576 | 0.439394 | 0.439394 | 0.4318182 | 0.496212 | 0.503788 |
| 0.3598485 | 0.356061 | 0.299242 | 0.348485 | 0.42803 | 0.42803 | 0.3977273 | 0.515152 | 0.522727 |
| 0.3143939 | 0.280303 | 0.208333 | 0.280303 | 0.397727 | 0.397727 | 0.3598485 | 0.545455 | 0.55303 |
| 0.3409091 | 0.306818 | 0.227273 | 0.306818 | 0.393939 | 0.393939 | 0.3863636 | 0.549242 | 0.556818 |
| 0.3106061 | 0.276515 | 0.19697 | 0.276515 | 0.325758 | 0.325758 | 0.3181818 | 0.617424 | 0.625 |
| 0.2992424 | 0.287879 | 0.246212 | 0.333333 | 0.253788 | 0.253788 | 0.2840909 | 0.742424 | 0.75 |
| 0.3977273 | 0.363636 | 0.291667 | 0.352273 | 0.420455 | 0.420455 | 0.3674242 | 0.462121 | 0.469697 |
| 0.3787879 | 0.344697 | 0.30303 | 0.356061 | 0.401515 | 0.401515 | 0.3484848 | 0.481061 | 0.488636 |
| 0.4280303 | 0.393939 | 0.314394 | 0.363636 | 0.450758 | 0.450758 | 0.3977273 | 0.431818 | 0.439394 |
| 0.0227273 | 0.056818 | 0.136364 | 0.140152 | 0.333333 | 0.333333 | 0.280303 | 0.609848 | 0.617424 |
| 0.030303 | 0.064394 | 0.143939 | 0.147727 | 0.325758 | 0.325758 | 0.2727273 | 0.617424 | 0.625 |
| 0 | 0.049242 | 0.113636 | 0.117424 | 0.356061 | 0.356061 | 0.0303030 | 0.587121 | 0.594697 |
| 0.0492424 | 0 | 0.0079545 | 0.098485 | 0.367424 | 0.367424 | 0.3143939 | 0.575758 | 0.583333 |
| 0.1136364 | 0.079545 | 0 | 0.109848 | 0.393939 | 0.393939 | 0.3409091 | 0.549242 | 0.556818 |
| 0.1174242 | 0.098485 | 0.109848 | 0 | 0.375 | 0.375 | 0.3219697 | 0.484848 | 0.492424 |
| 0.3560606 | 0.367424 | 0.393939 | 0.375 | 0 | 0 | 0.0530303 | 0.693182 | 0.700758 |
| 0.3560606 | 0.367424 | 0.393939 | 0.375 | 0 | 0 | 0.0530303 | 0.693182 | 0.700758 |
| 0.0303030 | 0.314394 | 0.340909 | 0.32197 | 0.05303 | 0.05303 | 0 | 0.640152 | 0.647727 |
| 0.5871212 | 0.575758 | 0.549242 | 0.484848 | 0.693182 | 0.693182 | 0.6401515 | 0 | 0.007576 |
| 0.594697 | 0.583333 | 0.556818 | 0.492424 | 0.700758 | 0.700758 | 0.6477273 | 0.007576 | 0 |

Table 29: Permuted normalized intensity matrix for Antigen 39 Expt. 5

| | X1.38 | X1.3 | X1.32 | X2.2.A12 | X2.2 | X2.31 |
|---|---|---|---|---|---|---|
| X1.38 | 1 | 0.9556467 | 1.082171 | 0.728455 | 0.415839 | 1.010222 |
| X1.3 | 1.195064 | 1 | 1.153844 | 0.836688 | 0.434696 | 1.0684126 |
| X1.32 | 1.018976 | 0.8960266 | 1 | 0.701949 | 0.399792 | 1.0866855 |
| X2.2.A12 | 1.445175 | 1.2849428 | 1.41624 | 1 | 0.648376 | 1.0493629 |
| X2.2 | 2.282608 | 1.8640445 | 2.072579 | 1.578489 | 1 | 1.087843 |
| X2.31 | 3.566636 | 4 | 4 | 2.462318 | 1.678114 | 1 |
| X2.34 | 3.092535 | 3.0546776 | 2.958207 | 2.028495 | 1.390512 | 0.9121071 |
| X2.7 | 2.762133 | 2.6579582 | 2.666277 | 1.915562 | 1.322912 | 1.2072549 |
| X2.21 | 4 | 3.9967567 | 3.986825 | 2.771361 | 1.960858 | 1.5525206 |
| X1.61 | 4 | 4 | 4 | 4 | 3.124079 | 2.2912864 |
| X1.59 | 4 | 2.5928433 | 2.026143 | 4 | 2.768431 | 0.6871665 |
| X1.53 | 4 | 2.5483377 | 1.961571 | 4 | 3.016718 | 0.695616 |
| X1.13 | 4 | 2.3948072 | 1.73598 | 3.965122 | 2.436741 | 0.579743 |
| X1.21 | 4 | 4 | 4 | 4 | 4 | 1.3378985 |
| X1.12 | 4 | 4 | 4 | 4 | 4 | 1.6338994 |
| X2.12 | 4 | 4 | 4 | 4 | 3.719227 | 1.194397 |
| X2.38 | 4 | 4 | 4 | 4 | 3.175417 | 1.3167289 |
| X2.35 | 4 | 4 | 4 | 4 | 2.638511 | 1.272587 |
| X2.1 | 4 | 4 | 4 | 3.7199 | 2.423343 | 1.1602561 |
| X2.17 | 4 | 4 | 4 | 3.588442 | 3.625906 | 2.6701065 |
| X1.31 | 4 | 4 | 4 | 4 | 3.439629 | 2.9941634 |
| X2.2.C5 | 4 | 4 | 4 | 4 | 3.444434 | 1.7627368 |
| BB1 | 1.834526 | 1.1647379 | 1.400791 | 1.114286 | 0.633017 | 0.6532861 |
| BB | 1.782694 | 1.161165 | 1.448943 | 1.144911 | 0.602166 | 0.624686 |

*FIG. 29A*

| FIG. 29A | FIG. 29B | FIG. 29C |

| X2.34 | X2.7 | X2.21 | X1.61 | X1.59 | X1.53 | X1.13 | X1.21 | X1.12 |
|---|---|---|---|---|---|---|---|---|
| 1.358201 | 0.950766 | 4 | 2.099597 | 4 | 4 | 4 | 3.6916588 | 4 |
| 1.473718 | 1.051501 | 4 | 2.297063 | 4 | 4 | 4 | 3.65431185 | 4 |
| 1.363081 | 0.956188 | 4 | 2.161708 | 4 | 4 | 4 | 2.8412459 | 2.9876653 |
| 1.291606 | 0.969702 | 4 | 1.763113 | 4 | 4 | 4 | 3.7555787 | 4 |
| 1.275596 | 1.302846 | 4 | 1.636573 | 4 | 4 | 4 | 2.9457543 | 4 |
| 1.032825 | 1.609188 | 4 | 2.138612 | 1.969598 | 1.432813 | 1.993775 | 2.2863749 | 2.8943472 |
| 1 | 1.356171 | 4 | 1.586444 | 4 | 4 | 4 | 2.1650544 | 3.0911961 |
| 1.371307 | 1 | 4 | 1.35743 | 4 | 4 | 4 | 2.1712449 | 2.9809524 |
| 1.650136 | 1.242287 | 4 | 1.146628 | 4 | 4 | 4 | 2.9521576 | 4 |
| 2.520667 | 1.579843 | 1.821012 | 1 | 1 | 0.838095 | 1.1111111 | 3.5612407 | 4 |
| 1.402976 | 2.306107 | 4 | 1.279368 | 4 | 1 | 1.325758 | 3.7796487 | 4 |
| 1.651273 | 2.496696 | 4 | 1.376682 | 1.053092 | 0.754286 | 1 | 3.3669912 | 4 |
| 1.282944 | 2.158281 | 4 | 1.144582 | 0.812551 | 4 | 4 | 1 | 0.9711538 |
| 2.857256 | 3.325587 | 4 | 3.046192 | 4 | 4 | 4 | 1.1217908 | 1 |
| 3.613993 | 4 | 4 | 3.875596 | 4 | 4 | 4 | 0.8565276 | 0.961402 |
| 2.42598 | 3.374092 | 4 | 2.205113 | 4 | 4 | 4 | 1.4040984 | 1.6230159 |
| 2.17793 | 2.944203 | 4 | 1.735533 | 4 | 4 | 4 | 1.79145 | 1.7526408 |
| 1.899281 | 2.228722 | 4 | 1.432524 | 4 | 4 | 4 | 1.325535 | 1.6204885 |
| 1.6883 | 2.176043 | 4 | 1.802071 | 4 | 4 | 4 | 3.3765184 | 3.8750487 |
| 2.955839 | 4 | 4 | 3.491564 | 4 | 4 | 4 | 3.8259129 | 4 |
| 2.721416 | 3.781592 | 4 | 3.856825 | 4 | 4 | 4 | 2.5323607 | 2.9322099 |
| 2.788713 | 3.603357 | 4 | 3.031764 | 4 | 4 | 1.75 | 0.7263312 | 0.7857143 |
| 0.838863 | 0.987009 | 2.58 | 0.702435 | 1.275304 | 1.32 | 1.75 | 0.7263312 | 0.7857143 |
| 0.804081 | 0.977662 | 2.58 | 0.557393 | 1.275304 | 1.32 | 1.75 | 0.6934707 | 0.7857143 |

FIG. 29C

| X2.12 | X2.38 | X2.35 | X2.1 | X2.17 | X1.31 | X2.2.C5 | BB1 | BB |
|---|---|---|---|---|---|---|---|---|
| 4 | 3.668437 | | 4 | 4 | 3.462784 | 4 | 1.365755 | 1 |
| 4 | 3.740418 | | 4 | 4 | 3.826652 | 4 | 1.319293 | 1 |
| 4 | 3.380469 | | 4 | 4 | 3.581612 | 4 | 1.300226 | 1 |
| 4 | 3.415129 | | 4 | 4 | 3.442462 | 4 | 1.305062 | 1 |
| 3.822002 | 2.699859 | | 4 | 3.052685 | 2.455923 | 2.971805 | 1.355045 | 1 |
| 2.863864 | 2.263142 | | 4 | 3.146926 | 3.366771 | 3.238294 | 1.398385 | 1 |
| 3.143141 | 2.198091 | | 4 | 3.169308 | 2.595526 | 3.137096 | 1.516716 | 1 |
| 3.697021 | 2.757579 | | 4 | 3.899956 | 3.147871 | 3.746235 | 1.207576 | 1 |
| 3.872801 | 2.650477 | | 4 | 4 | 3.526345 | 3.910644 | 1.253208 | 1 |
| 4 | 2.902623 | | 4 | 4 | 4 | 4 | 1.779507 | 1 |
| 4 | 1.169345 | | 4 | 3.99544 | 1.350703 | 4 | 1.573016 | 1 |
| 4 | 1.195034 | | 4 | 4 | 1.43492 | 4 | 1.848485 | 1 |
| 3.750122 | 1.06997 | | 4 | 3.483814 | 1.272282 | 4 | 1.554286 | 1 |
| 1.131881 | 0.908273 | 2.729021 | 4 | 4 | 4 | 2.748884 | 2.089161 | 1 |
| 1.227134 | 0.970305 | 2.884091 | 4 | 4 | 4 | 2.917652 | 2.084091 | 1 |
| 1 | 0.785096 | 3.121894 | 4 | 4 | 3.49677 | 3.36018 | 1.895186 | 1 |
| 1.561497 | 1 | | 4 | 4 | 3.67389 | 3.775016 | 2.046086 | 1 |
| 1.809159 | 1.126746 | | 4 | 4 | 3.38724 | 3.572644 | 1.552817 | 1 |
| 1.496373 | 1.08473 | | 4 | 2.494603 | 2.19415 | 1.941085 | 1.733391 | 1 |
| 3.653984 | 2.53483 | | 4 | 1 | 0.938772 | 1.009463 | 2.06812 | 1 |
| 4 | 2.962157 | | 4 | 0.905031 | 1 | 1.0284 | 2.066465 | 1 |
| 2.939858 | 1.916265 | | 4 | 0.946539 | 0.916792 | 1 | 2.010724 | 1 |
| 0.95471 | 0.74775 | 1.755 | 3.435 | 0.930468 | 0.773266 | 1.162466 | 1 | 1 |
| 0.878628 | 0.667853 | 1.655 | 3.2425 | 0.896427 | 0.766269 | 1.066436 | 1 | 1 |

Table 23: Table of Clusters for Antigen 39 Experiments

| Clusters | Expt I | Expt II | Expt III | Expt IV | Expt V | Combined |
|---|---|---|---|---|---|---|
| 1 | 1.21 | 1.57, 1.61 | 1.32 | 1.17, 1.16, 1.55, 1.11, 1.12 | 1.38, 1.3, 1.32, 2.2A12, 2.2 | 1.17, 1.55, 1.16, 1.11, 1.12 |
| 2 | 1.12, 1.63, 1.17, 1.55, 2.12 | 1.11 | 1.3 | 1.63 | 2.31 | 1.21, 2.12, 2.38 |
| 3 | 1.32 | 1.8, 1.30, 1.38 | 1.8 | 1.66, 1.8, 1.1 | 2.34, 2.7, 2.21 | 2.35, 2.1 |
| 4 | 1.1 | 1.53, 1.3 | 2.34, 2.28 | 1.57, 1.61, 1.23, 1.24 | 1.61 | 1.63 |
| 5 | 2.28, 2.34, 2.20 | 1.59 | 1.13, 1.53, 1.31 | 1.31, 1.46, 1.65, 1.29 | 1.59, 1.53, 1.13 | 1.66, 1.1, 1.8, 1.30, 1.38 |
| 6 | 1.46, 1.31, 2.17, 1.29 | 1.24 | 1.55, 1.12, 1.17, 2.12, 1.11, 1.21 | 1.53. 1.3 | 1.21, 1.12, 2.12, 2.38 | 1.3 |
| 7 | 1.13 | | 2.2A12, 1.24 | | 2.35, 2.1 | 1.32 |
| 8 | 2.2A12 | | | | 2.17, 1.31, 2.2C5 | 1.57, 1.61, 1.23, 2.28 |
| 9 | | | | | | 1.24 |
| 10 | | | | | | 2.34, 2.2 |
| 11 | | | | | | 2.7, 2.21 |
| 12 | | | | | | 2.31 |
| 13 | | | | | | 1.31, 2.17, 1.46, 2.2C5, 1.65, 1.29 |
| 14 | | | | | | 1.53, 1.59 |
| 15 | | | | | | 1.13 |
| 16 | | | | | | 2.2A12 |

FIG. 30

ANTIBODY CATEGORIZATION BASED ON BINDING CHARACTERISTICS

RELATED APPLICATIONS

This application is a continuation of U.S. Nonprovisional patent application Ser. No. 10/309,419, filed Dec. 2, 2002, now issued as U.S. Pat. No. 7,771,951, which claims priority to U.S. Provisional Patent Application Ser. No. 60/337,245, filed Dec. 3, 2001, and U.S. Provisional Patent Application Ser. No. 60/419,387, filed Oct. 16, 2002, all of which are hereby incorporated by reference.

FIELD OF THE INVENTION

The present invention relates to grouping antibodies based on the epitopes they recognize and identifying antibodies having distinct binding characteristics. In particular, the present invention relates to antibody competition assay methods for determining antibodies that bind to an epitope, and data analysis processes for dividing antigen-specific antibodies into clusters or "bins" representing distinct binding specificities. Specifically, the invention relates to the Multiplexed Competitive Antibody Binning (MCAB) high-throughput antibody competition assay and the Competitive Pattern Recognition (CPR) data analysis process for analyzing data generated by high-throughput assays.

BACKGROUND OF THE INVENTION

Monoclonal antibodies (mAb) show an important therapeutic utility in the treatment of a wide variety of diseases such as infectious diseases, cardiovascular disease, inflammation, and cancer. (Storch (1998) *Pediatrics* 102:648-651; Coller et al. (1995) *Thromb. Haemostasis* 74:302-308; Present et al. (1999) *New Eng. J. Med.* 6:1398-1405; Goldenberg (1999) *Clin. Ther.* 21:309-318). Cells produce antibodies in response to infection or immunization with a foreign substance or antigen. The potential therapeutic utility of monoclonal antibodies is in part due to their specific and high-affinity binding to a target. Antibodies bind specifically to a target antigen by recognizing a particular site, or epitope, on the antigen. With the use of the recently developed XenoMouse® technology (Abgenix, Inc., Fremont, Calif.) together with established procedures for hybridoma cells or B cells (Kohler and Milstein (1975) *Nature* 256:495-497) and isolating lymphocytes (Babcook et al. (1996) *Proc. Natl. Acad. Sci.* 93:7843-7848), it is possible to generate large numbers of antigen-specific human monoclonal antibodies against almost any human antigen. (Green (1999) *Jnl. Immunol. Methods* 231:11-23, Jakobovits et al. (1993) *Proc. Natl. Acad. Sci. U.S.A.,* 90:2551-2555, Mendez et. al. (1997) *Nat. Genet.* 15:146-156; Green and Jakobivits, *J. Exp. Med.* (1998), 188:483-495).

The large numbers of antibodies generated against a particular target antigen may vary substantially in terms of both how strongly they bind to the antigen as well as the particular epitope they bind to on the target antigen. Different antibodies generated against an antigen recognize different epitopes and have varying binding affinities to each epitope. In order to identify therapeutically useful antibodies from the large number of generated candidate antibodies, it is necessary to screen large numbers of antibodies for their binding affinities and epitope recognition properties. For this reason, it would be advantageous to have a rapid method of screening antibodies generated against a particular target antigen to identify those antibodies that are most likely to have a therapeutic effect. In addition, it would be advantageous to provide a mechanism for categorizing the generated antibodies according to their target epitope binding sites.

SUMMARY OF THE INVENTION

The present disclosure provides methods for categorizing antibodies based on their epitope binding characteristics. One aspect provides methods and systems for determining the epitope recognition properties of different antibodies. Another aspect provides data analysis processes for clustering antibodies on the basis of their epitope recognition properties and for identifying antibodies having distinct epitope binding characteristics. Antibody categorization or "binning" as disclosed and claimed herein encompasses assay methods and data analysis processes for determining the epitope binding characteristics of a pool of antigen-specific antibodies, clustering antibodies into "bins" representing distinct epitope binding characteristics, and identifying antibodies having desired binding characteristics.

The method for categorizing antibodies based on binding characteristics includes:

a) providing a set of antibodies that bind to an antigen, labelling each antibody in the set to form a labelled reference antibody set such that each labelled reference antibody is distinguishable from every other labelled reference antibody in the labelled reference antibody set, selecting a probe antibody from the set of antibodies that bind to the antigen, contacting the probe antibody with the labelled reference antibody set in the presence of the antigen, detecting probe antibody in a complex that includes a labelled reference antibody bound to antigen, the antigen, and probe antibody bound to antigen; and b) providing input data representing the outcomes of at least one antibody competition assay using a set of antibodies that bind to an antigen as in step a), normalizing the input data to generate a normalized intensity matrix, computing at least one dissimilarity matrix comprising generating a threshold matrix from the normalized intensity matrix and computing a dissimilarity matrix from the threshold matrix, and clustering antibodies based on dissimilarity values in cells of the dissimilarity matrix, to determine epitope binding patterns of set of antibodies that bind to an antigen. The input data can be generated by a high throughput assay, preferably by the Multiplexed Competitive Antibody Binning (MCAB) assay. Preferably, the Competitive Pattern Recognition process is used for data analysis.

For the antibody competition assay method, the probe antibody may be labelled, and detected in a complex that includes a labelled reference antibody bound to antigen, antigen, and labelled probe antibody bound to antigen, which allows determination whether the labelled probe antibody competes with any reference antibody in the labelled reference antibody set, because competition indicates that the probe antibody binds to the same epitope as another antibody in the set of antibodies that bind to an antigen. The probe antibody can be labelled, for example, with an enzymatic label, or a colorimetric label, or a fluorescent label, or a radioactive label.

In a preferred embodiment of the antibody competition assay method, a detection antibody is used to detect bound probe antibody, where the detection antibody binds only to probe antibody and not to reference antibody. The detection antibody detects bound probe antibody in complex that includes a labelled reference antibody bound to antigen, antigen, and labelled probe antibody bound to antigen. A labelled detection antibody is used to detect bound probe antibody, where the detection antibody can be labelled, for example, with an enzymatic label, or a colorimetric label, or a fluorescent label, or a radioactive label. Alternately, the detection antibody is detected using a detection means such as an antibody-binding protein.

In particular, the antibody competition assay method for determining antibodies that bind to an epitope on an antigen includes providing a set of antibodies that bind to an antigen, labelling each antibody in the set with a uniquely colored bead to form a labelled reference antibody set such that each labelled reference antibody is distinguishable from every other labelled reference antibody in the labelled reference antibody set, selecting a probe antibody from the set of antibodies that bind to the antigen, contacting the probe antibody with the labelled reference antibody set in the presence of the antigen, detecting bound probe antibody in a complex that includes a labelled reference antibody bound to antigen, antigen, and probe antibody bound to antigen, and determining whether the probe antibody competes with any reference antibody in the labelled reference antibody set, where competition indicates that the probe antibody binds to the same epitope as another antibody in the set of antibodies that bind to an antigen. Each uniquely colored bead may have a distinct emission spectrum. The probe antibody can be labelled, for example, with an enzymatic label, or a colorimetric label, or a fluorescent label, or a radioactive label. Alternately, a detection antibody is used to detect bound probe antibody, where the detection antibody may be labelled. The labelled detection antibody can be labelled, for example, with an enzymatic label, or a colorimetric label, or a fluorescent label, or a radioactive label.

Another aspect of the present invention provides a method for characterizing antibodies based on binding characteristics by providing input data representing the outcomes of at least one antibody competition assay using a set of antibodies that bind to an antigen, normalizing the input data to generate a normalized intensity matrix, computing at least one dissimilarity matrix comprising generating a threshold matrix from the normalized intensity matrix and computing a dissimilarity matrix from the threshold matrix, and clustering antibodies based on dissimilarity values in cells of the dissimilarity matrix, to determine epitope binding patterns of set of antibodies that bind to an antigen.

The input data can be signal intensity values representing the outcomes of an antibody competition assay using a set of antibodies that bind to an antigen. The input data representing the outcomes of an antibody competition assay can be stored in matrix form. The input data stored in matrix form can be in a two-dimensional matrix or a multidimensional matrix, and may be stored in a plurality of matrices. The input data stored in matrix form can be signal intensity values representing the outcomes of an antibody competition assay. The antibody competition assay can be the Multiple Competitive Antibody Binning (MCAB) assay. The input data stored in matrix form can be at least one matrix wherein each cell of the matrix comprises the signal intensity value of an individual antibody competition assay.

Normalizing the input data to generate a normalized intensity matrix can include generating a background-normalized intensity matrix by subtracting a first matrix with signal intensity values from a first antibody competition assay in which antigen was not added (negative control) from a second matrix with signal intensity values from a second antibody competition assay in which antigen was added. A minimum threshold value for blocking buffer values is set, and any blocking buffer values below the threshold value are adjusted to the threshold value prior to said generating the normalized intensity matrix.

If desired, the normalizing step includes generating an intensity-normalized matrix by dividing each value in a column of the background-normalized intensity matrix by the blocking buffer intensity value for the column. The normalizing step can further include normalizing relative to the baseline signal for probe antibodies by dividing each column of the intensity-normalized matrix by its corresponding diagonal value to generate a final intensity-normalized matrix. Prior to dividing each column by its corresponding diagonal value, each diagonal value is compared with a user-defined threshold value and any said diagonal value below the user-defined threshold value is adjusted to the threshold value.

If desired, the normalizing step includes generating an intensity-normalized matrix by dividing each value in a row of the background-normalized intensity matrix by the blocking buffer intensity value for the row. The normalizing step can further include normalizing relative to the baseline signal for probe antibodies by dividing each row of the intensity-normalized matrix by its corresponding diagonal value to generate a final intensity-normalized matrix. Prior to dividing each row by its corresponding diagonal value, each diagonal value is compared with a user-defined threshold value and any said diagonal value below the user-defined threshold value is adjusted to the threshold value.

Generating the threshold matrix involves setting the normalized valued in each cell of the normalized intensity matrix to a value of one (1) or zero (0), wherein normalized values less than or equal to a threshold value are set to a value of zero (0) and normalized values greater to a threshold value are set to a value of one (1).

At least one dissimilarity matrix is computed from the threshold matrix of ones and zeroes by determining the number of positions in which each pair of rows differs. A plurality of dissimilarity matrices can be computed using a plurality of threshold values. The average of a plurality of dissimilarity matrices can computed and used as input to the clustering step.

Clustering antibodies based on said dissimilarity values in cells of said dissimilarity matrix can include hierarchical clustering. Hierarchical clustering includes generating a hierarchy of nested subsets of antibodies within a set of antibodies that bind to an antigen by determining the pair of antibodies in the set having the lowest dissimilarity value, then determining the pair of antibodies having the next lowest dissimilarity value, and iteratively repeating this determining each pair of antibodies having the next lowest dissimilarity value until one pair of antibodies remains, such that a hierarchy of nested subsets is generated that indicates the similarity of competition patterns within the set of antibodies. Clusters are determined based on competition patterns.

Alternately, the data analysis process involves subtracting the data matrix for the experiment carried out with antigen from the data matrix for the experiment without antigen. The value in each diagonal cell is then used as a background value for determining the binding affinity of the antibody in the corresponding column. Cells in the subtracted matrix having values significantly higher than the corresponding diagonal value are highlighted or otherwise noted.

Data from the clustering step can be captured, including by automated means. In particular, data from the clustering step can be captured in a format compatible with data input device or computer. The clustering step can generate a display, which can be in a format compatible with data input device or computer. The display generated by the clustering step can be a dissimilarity matrix. Clusters can be determined by visual inspection of the dissimilarity value in each cell of the dissimilarity matrix. The dissimilarity matrix can include cells having a visual indicator of the cluster to which the antibody pair represented by said cell belongs, where the visual indicator may be a color, or shading, or patterning. Alternately, the display can be a dendrogram defined by dissimilarity values computed for a set of antibodies. Such a dendrogram has branches representing antibodies in the set of antibodies, wherein the arrangement of branches represents relationships between antibodies within the set of antibodies, and the arrangement further represents clusters of antibodies within the set of antibodies. In such a dendrogram, the length of any branch represents the degree of similarity between the binding pattern of antibodies or cluster of antibodies represented by said branch.

Input data representing the outcomes of a plurality of antibody competition assays can be analyzed, wherein each assay represents an individual experiment using a set of antibodies that bind to an antigen, further wherein each experiment includes at least one antibody that is also tested in at least one other experiment. When a plurality of experiments is analyzed, an individual normalized intensity matrix can be generated for each individual experiment and a single normalized intensity matrix can be generated by computing the average intensity value of each antibody pair represented in each individual normalized intensity matrix. A single dissimilarity matrix representing each antibody pair tested in the plurality of antibody competition assays can be generated from the single normalized intensity matrix.

BRIEF DESCRIPTION OF THE DRAWINGS

FIG. 2. Correlation between blocking buffer intensity values and average intensity.

FIG. 3. Comparison of epitope binning results with FACS results. Results from antibody experiments using the ANTIGEN39 antibody are shown, comparing results using the epitope binning method described herein with results using flow cytometry (fluorescence-activated cell sorter, FACS). Antibodies are assigned to bins 1-15, as indicated by rows 1-15 in the far left column using the epitope binning assay. Hatching in cells indicates antibodies that are FACS positive for cells expressing ANTIGEN39 (cell line 786-0), and no hatching indicates antibodies that are negative for cells that do not express ANTIGEN39 (cell line M14).

FIG. 6. Dendrograms for ANTIGEN39 antibodies. FIG. 6B. Dendrogram for the ANTIGEN39 antibodies for Experiment 1. Antibodies 1.12, 1.63, 1.17, 1.55, and 2.12 consistently cluster together in this experiment as well as in other experiments, as do antibodies 1.46, 1.31, 2.17, and 1.29. FIG. 6C. Dendrogram for the ANTIGEN39 antibodies for Experiment 2. Antibodies 1.57 and 1.61 consistently cluster together in this experiment as well as in other experiments. FIG. 6D. Dendrogram for the ANTIGEN39 antibodies for Experiment 3. Antibodies 1.55, 1.12, 1.17, 2.12, 1.11 and 1.21 consistently cluster together in this experiment as well as in other experiments. FIG. 6F. Dendrogram for the ANTIGEN39 antibodies for Experiment 5. Antibodies 1.21, 1.12, 2.12, 2.38, 2.35, and 2.1 consistently cluster together in this experiment as well as in other experiments.

FIG. 7. Dendrograms for clustering IL-8 monoclonal antibodies.

FIG. 8. Intensity matrices generated in the embodiment disclosed in Example 2 using a set of antibodies against ANTIGEN14. FIGS. 8A and 8B are tables showing the intensity matrix for experiment conducted with antigen. FIGS. 8C and 8D are tables showing the intensity matrix for the same experiment conducted without antigen (control). These matrices are used as input data matrices for subsequence steps in data analysis.

FIG. 9. Difference matrix for antibodies against the ANTIGEN14 target. Difference matrix is generated by subtracting the matrix corresponding to values obtained from experiment without antigen (see FIG. 8B) from the matrix corresponding to values obtained from the experiment with antigen (see FIG. 8A) disclosed in Example 2.

FIG. 10. Adjusted difference matrix with minimum threshold value. For the intensity values of Example 2, the minimum reliable signal intensity value is set to 200 intensity units and values below the minimum threshold are set to the threshold of 200.

FIG. 11. Row normalized matrix. Each row in the adjusted difference matrix of FIG. 10 is adjusted by dividing it by the last intensity value in the row, which corresponds to the intensity value for beads to which blocking buffer is added in place of primary antibody. This adjusts for well-to-well intensity.

FIG. 12. Diagonal normalized matrix. All columns except the one corresponding to Antibody 2.42 were column-normalized. Dividing each column by its corresponding diagonal is carried out to measure each intensity relative to an intensity that is known to reflect competition—i.e., competition against self.

FIG. 13. Antibody pattern recognition matrix. For data from the embodiment disclosed in Example 2, intensity values below the user-defined threshold were set to zero. The user-defined threshold was set to two (2) times the diagonal intensity values. Remaining values were set to one.

FIG. 14. Dissimilarity matrix. For data from the embodiment disclosed in Example 2, a dissimilarity matrix is generated from the matrix of zeroes and ones shown in FIG. 13, by setting the entry in row i and column j to the fraction of the positions at which two rows, i and j, differ. FIG. 14 shows the number of positions, out of 22 total, at which the patterns for any two antibodies differed for set of antibodies generated against the ANTIGEN14 target.

FIG. 15. Average dissimilarity matrix. After separate dissimilarity matrices were generated from each of several threshold values ranging from 1.5 to 2.5 times the values of the diagonals, the average of these dissimilarity matrices was computed (FIG. 15) and used as input to the clustering process.

FIG. 16. Permuted average dissimilarity matrix. For data from the embodiment disclosed in Example 2, clusters can be visualized in matrices. In FIG. 16, the rows and columns of the dissimilarity matrix were rearranged according to the order of the "leaves" or clades on the dendrogram shown in FIG. 5, and individual cells were visually coded according to the degree of dissimilarity.

FIG. 17. Permuted normalized intensity matrix. For data from the embodiment disclosed in Example 2, rows and columns of the normalized intensity matrix were rearranged according to the order of the leaves on the dendrogram shown in FIG. 5, and individual cells were visually coded according to their normalized intensity values.

FIG. 18. Permuted average dissimilarity matrix for five ANTIGEN39 input data sets. Data from five experiments that were conducted using antibodies against the ANTIGEN39 target (see Example 3) produced five input data sets. Dissimilarity matrices were generated for each input data set, and an average dissimilarity matrix was generated, and rows and columns were arranged (permuted) according to arrangement of the corresponding dendrogram(s) shown in FIG. 6.

FIG. 19. Permuted normalized intensity matrix for five ANTIGEN39 input data sets. Data from five experiments that were conducted using antibodies against the ANTIGEN39 target (see Example 3) produced five input data sets. A normalized intensity matrix was generated for the five input data sets and rows and columns were arranged (permuted) according to arrangement of the corresponding dendrogram(s) shown in FIG. 6.

FIG. 20. Permuted average dissimilarity matrix for Experiment 1 using a set of antibodies against the ANTIGEN39 target. Data from the set of antibodies analyzed in Experiment 1 (Example 3) were analyzed. See dendrogram shown in FIG. 6B.

FIG. 21. Permuted normalized intensity matrix for Experiment 1 using a set of antibodies against the ANTIGEN39 target. Data from the set of antibodies analyzed in Experiment 1 (Example 3) were analyzed. See dendrogram shown in FIG. 6B.

FIG. 22. Permuted average dissimilarity matrix for Experiment 2 using a set of antibodies against the ANTIGEN39 target. Data from the set of antibodies analyzed in Experiment 2 (Example 3) were analyzed. See dendrogram shown in FIG. 6C.

FIG. 23. Permuted normalized intensity matrix for Experiment 2 using a set of antibodies against the ANTIGEN39 target. Data from the set of antibodies analyzed in Experiment 2 (Example 3) were analyzed. See dendrogram shown in FIG. 6C.

FIG. 24. Permuted average dissimilarity matrix for Experiment 3 using a set of antibodies against the ANTIGEN39 target. Data from the set of antibodies analyzed in Experiment 3 (Example 3) were analyzed. See dendrogram shown in FIG. 6D.

FIG. 25. Permuted normalized intensity matrix for Experiment 3 using a set of antibodies against the ANTIGEN39 target. Data from the set of antibodies analyzed in Experiment 3 (Example 3) were analyzed. See dendrogram shown in FIG. 6D.

FIG. 26. Permuted average dissimilarity matrix for Experiment 4 using a set of antibodies against the ANTIGEN39 target. Data from the set of antibodies analyzed in Experiment 4 (Example 3) were analyzed. See dendrogram shown in FIG. 6E.

FIG. 27. Permuted normalized intensity matrix for Experiment 4 using a set of antibodies against the ANTIGEN39 target. Data from the set of antibodies analyzed in Experiment 4 (Example 3) were analyzed. See dendrogram shown in FIG. 6E.

FIG. 28. Permuted average dissimilarity matrix for Experiment 5 using a set of antibodies against the ANTIGEN39 target. Data from the set of antibodies analyzed in Experiment 5 (Example 3) were analyzed. See dendrogram shown in FIG. 6F.

FIG. 29. Permuted normalized intensity matrix for Experiment 5 using a set of antibodies against the ANTIGEN39 target. Data from the set of antibodies analyzed in Experiment 5 (Example 3) were analyzed. See dendrogram shown in FIG. 6F.

FIG. 30. Clusters identified in Experiments 1-5 using sets of antibodies against the ANTIGEN39 target. FIG. 30 summarizes the clusters identified for each of the five individual data sets and for the combined data set for all of the antibodies generated in all five experiments disclosed in Example 3.

DETAILED DESCRIPTION OF THE PREFERRED EMBODIMENT

Figure 1:
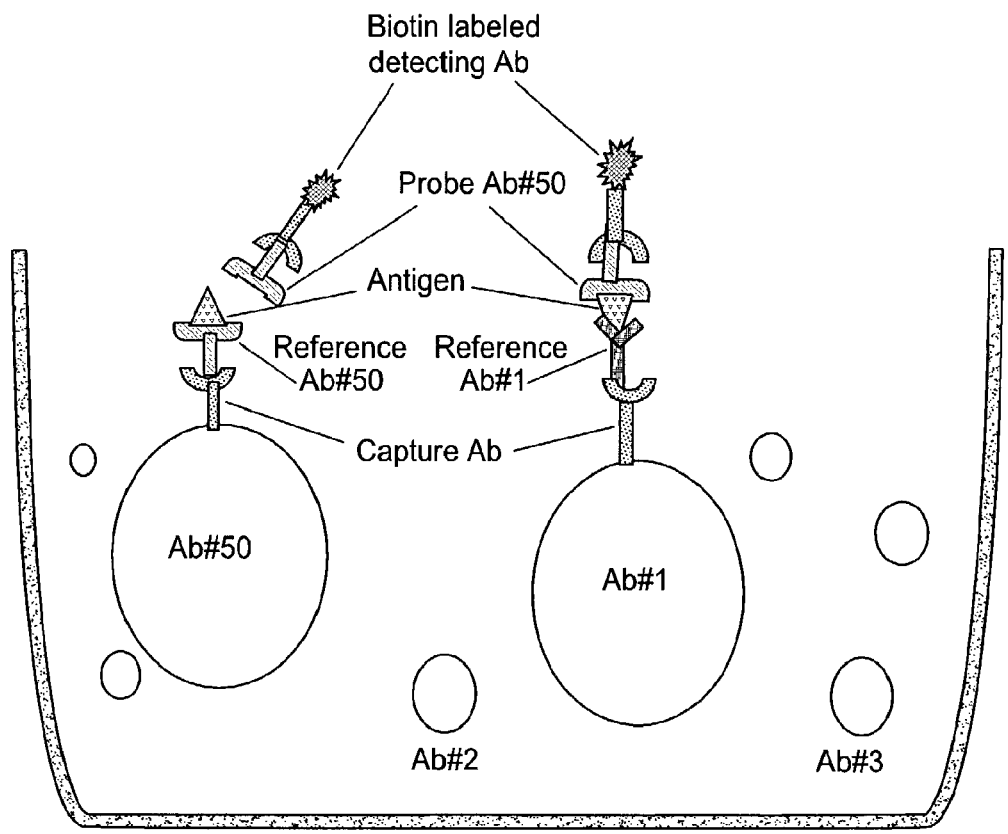
FIG. 1. Schematic illustration of one embodiment of an epitope binning assay using labelled bead technology in a single well of a microliter plate. Each reference antibody is coupled to a bead with distinct emission spectrum, forming a uniquely labelled reference antibody. The entire set of uniquely labelled reference antibodies is placed in the well of a multiwell microtiter plate and incubated with antigen. A probe antibody is added and the interaction of probe antibody with each uniquely labelled reference antibody is determined.

With increased fusion efficiency producing larger numbers of antigen specific antibodies from each hybridoma-cell fusion experiment, a screening method of managing and prioritizing large numbers of antibodies becomes ever more important. When a set of monoclonal antibodies has been generated against a target antigen, different antibodies in the set will recognize different epitopes, and will also have variable binding affinities. Thus, to effectively screen large numbers of antibodies it is important to determine which epitope each antibody binds, and to determine binding affinity for each antibody.

Epitope binning, as described herein, is the process of grouping antibodies based on the epitopes they recognize. More particularly, epitope binning comprises methods and systems for discriminating the epitope recognition properties of different antibodies, combined with computational processes for clustering antibodies based on their epitope recognition properties and identifying antibodies having distinct binding specificities. Accordingly, embodiments include assays for determining the epitope binding properties of antibodies, and processes for analyzing data generated from such assays.

In general, the invention provides an assay to determine whether a test moiety (such as an antibody) binds to a test object (such as an antigen) in competition with other test moieties (such as other antibodies). A capture moiety is used to capture the test object and/or the test moiety in an addressable manner and a detection moiety is utilized to addressably detect binding between other test moieties and the test object. When a test moiety binds to the same or similar location on the test subject as the test moiety being assayed, no binding is detected, whereas when a test moiety binds to a different location on the test subject as the test moiety being assayed, binding is detected. In each case, the binding or lack thereof is addressable, so the relative interactions between test moieties with the test object can be readily ascertained and categorized.

One embodiment of the invention is a competition-based method of categorizing a set of antibodies that have been generated against an antigen. This method relies upon carrying out a series of assays wherein each antibody from the set is tested for competitive binding against all other antibodies from the set. Thus, each antibody will be used in two different modes: in at least one assay, each antibody will be used in "detect" mode as the "probe antibody" that is tested against all the other antibodies in the set; in other assays, the antibody will be used in "capture" mode as a "reference antibody" within the set of reference antibodies being assayed. Within the set of reference antibodies, each reference antibody will be uniquely labelled in a way that permits detection and identification each reference antibody within a mixture of reference antibodies. The method relies on forming "sandwiches" or complexes involving reference antibodies, antigen, and probe antibody, and detecting the formation or lack of formation of these complexes. Because each reference antibody in the set is uniquely labelled, it is possible to addressably determine whether a complex has formed for each reference antibody present in the set of reference antibodies being assayed.

Antibody Assay Overview

The method begins by selecting an antibody from the set of antibodies against an antigen, where the selected antibody will serve as the "probe antibody" that is to be tested for competitive binding against all other antibodies of the set. A mixture containing all the antibodies will serve as a set of "reference antibodies" for the assay, where each reference antibody in the mixture is uniquely labelled. In an assay, the probe antibody is contacted with the set of reference antibodies, in the presence of the target antigen. Accordingly, a complex will form between the probe antibody and any other antibody in the set that does not compete for the same epitope on the target antigen. A complex will not form between the probe antibody and any other antibody in the set that competes for the same epitope on the target antigen. Formation of complexes is detected using a labelled detection antibody that binds the probe antibody. Because each reference antibody in the mixture is uniquely labelled, it is possible to determine for each reference antibody whether that reference antibody does or does not form a complex with the probe antibody. Thus, it can be determined which antibodies in the mixture compete with the probe antibody and bind to the same epitope as the probe antibody.

Each antibody is used as the probe antibody in at least one assay. By repeating this method of testing each individual antibody in the set against the entire set of antibodies, the competitive binding affinities can be generated for the entire set of antibodies against an antigen. From such a affinity measurements, one can determine which antibodies in the set have similar binding characteristics to other antibodies in the set, thereby allowing the grouping or "binning" of each antibody on the basis of its epitope binding profile. A table of competitive binding affinity measurements is a suitable method for displaying assay results. A preferred embodiment of this method is the Multiplexed Competitive Antibody Binning (MCAB) assay for high-throughput screening of antibodies.

Because this embodiment relies on testing antibody competition, wherein a single antibody is tested against the entire set of antibodies generated against an antigen, one challenge to implementing this method relates to the mechanism used to uniquely identify and quantitatively measure complexes formed between the single antibody and any one of the other antibodies in the set. It is this quantitative measurement that provides an estimate of whether two antibodies are competing for the same epitope on the antigen.

As described below, embodiments of the invention relate to uniquely labelling each reference antibody in the set prior to creating a mixture of all antibodies. This unique label, as discussed below, is not limited to any particular mechanism. Rather, it is contemplated that any method that provides a way to identify each reference antibody within the mixture, allowing one to distinguish each reference antibody in the set from every other reference antibody in the set, would be suitable. For example, each reference antibody can be labelled colorimetrically so that the particular color of each antibody in the set is determinable. Alternatively, each reference antibody in the set might be labelled radioactively using differing radioactive isotopes. The reference antibody may be labelled by coupling, linking, or attaching the antibody to a labelled object such as a bead or other surface.

Once each reference antibody in the set has been uniquely labelled, a mixture is formed containing all the reference antibodies. Antigen is added to the mixture, and the probe antibody is added to the mixture. A detection label is necessary in order to detect complexes containing bound probe antibody. A detection label may be a labelled detection antibody or it may be another label that binds to the probe antibody. For example, when a set of human monoclonal antibodies is being tested, a mouse anti-human monoclonal antibody is suitable for use as a detection antibody. The detection label is chosen to be distinct from all other labels in the mixture that are used to label reference antibodies. For example, a labelled detection antibody might be labelled with a unique color, or radioactively labelled, or labelled by a particular fluorescent marker such as phycoerythrin (PE).

The design of an experiment must include selecting conditions such that the detection antibody will only bind to the probe antibody, and will not bind to the reference antibodies. In embodiments in which reference antibodies are coupled to beads or other materials through antibodies, the antibody that couples the reference antibody to the bead (the "capture antibody") will be the same antibody as the detection antibody. In accordance with this embodiment of the invention, the detection antibody is specifically chosen or modified so that the detection antibody binds only to the probe antibody and does not bind to the reference antibody. By using the same antibody for both detection and capture, each will block one the other from binding to their respective targets. Accordingly, when the capture antibody is bound to the reference antibody, it will block the detection antibody from binding to the same epitope on the reference antibody and producing a false positive result. Antibodies suitable for use as detection antibodies include mouse anti-human IgG2, IgG3, and IgG4 antibodies available from Calbiochem, (Catalog No. 411427, mouse anti-human IgKappa available from Southern Biotechnology Associates, Inc. (Catalog Nos. 9220-01 and 9220-08, and mouse anti-hIgG from PharMingen (Catalog Nos. 555784 and 555785).

Once the labelled detection antibody has been added to the mixture, the entire mixture can then be analyzed to detect complexes between labelled detection antibody, bound probe antibody, the antigen, and uniquely labelled reference antibody. The detection method must permit detection of complexes (or lack thereof) for each uniquely labelled reference antibody in the mixture.

Detecting whether a complex formed between a probe antibody and each reference antibody in the set indicates, for each reference antibody, whether that reference antibody competes with the probe antibody for binding to the same (or nearby) epitope. Because the mixture of reference antibodies will include the antibody being used as the probe antibody, it is expected that this provides a negative control. Detecting complex formation allows measurement of competitive affinities of the antibodies in the set being tested. This measurement of competitive affinities is then used to categorize each antibody in the set based on how strongly or weakly they bind to the same epitopes on the target antigen. This provides a rapid method for grouping antibodies in a set based on their binding characteristics.

In one embodiment, large numbers of antibodies can be simultaneously screened for their epitope recognition properties in a single experiment in accordance with embodiments of the present invention, as described below. Generally, the term "experiment" is used nonexclusively herein to indicate a collection of individual antibody assays and suitable controls. The term "assay" is used nonexclusively herein to refer to individual assays, for example reactions carried out in a single well of a microtiter plate using a single probe antibody, or may be used to refer to a collection of assays or to refer to a method of measuring antibody binding and competition as described herein.

In one embodiment, large numbers of antibodies are simultaneously screened for their epitope recognition properties using a sandwich assay involving a set of reference antibodies in which each reference antibody in the set is bound to a uniquely labelled "capture" antibody. The capture antibody can be, for example, a colorimetrically labelled antibody that has strong affinity for the antibodies in the set. As one example, the capture antibody can be a labelled mouse, goat, or bovine anti-human IgG or anti-human IgKappa antibody. Although embodiments described herein use a mouse monoclonal anti-human IgG antibody, other similar capture antibodies that will bind to the antibodies being studied are within the scope of the invention. Thus, one of skill in the art can select an appropriate capture antibody based on the origin of the set of antibodies being tested.

One embodiment of the present invention therefore provides a method of categorizing, for example, which epitopes on a target antigen are bound by fifty (50) different antibodies generated against that target antigen. Once the 50 antibodies have been determined to have some affinity for a target antigen, the methods described below are used to determine which antibodies in the group of 50 bind to the same epitope. These methods are performed by using each one of the 50 antibodies as a probe antibody to cross-compete against a mixture of all 50 antibodies (the reference antibodies), wherein the 50 uniquely labelled reference antibodies in the mixture are each labelled by a capture antibody. Those antibodies that recognize the same epitope will compete with one another, while antibodies that do not compete are assumed to not bind to the same epitope. By uniquely labelling a large number of antibodies in a single reaction, as described below, these methods allow for a pre-selected antibody to be competed against 10, 25, 50, 100, 200, 300, or more antibodies at one time. For this reason, the choice of testing 50 antibodies in an experiment is arbitrary, and should not be viewed as limiting on the invention.

Preferably, the Multiplex Competitive Antibody Binning (MCAB) assay is used. More preferably, the MCAB assay is practiced utilizing the LUMINEX System (Luminex Corp., Austin Tex.), wherein up to 100 antibodies can be binned simultaneously using the method illustrated in FIG. 1. The MCAB assay is based on the competitive binding of two antibodies to a single antigen molecule. The entire set of antibodies to be characterized is used twice in the MCAB assay, in "capture" and "detect" modes in the MCAB sandwich assay.

In one embodiment, each capture antibody is uniquely labelled. Once a capture antibody has been uniquely labelled, it is exposed to one of the set of antibodies being tested, forming a reference antibody that is uniquely labelled. This is repeated for the remaining antibodies in the set so that each antibody becomes labelled with a different colored capture antibody. For example, when 50 antibodies are being tested, a labelled reference antibody mixture is created by mixing all 50 uniquely labelled reference antibodies into a single reaction well. For this reason, it is useful for each label to have a distinct property that allows it to be distinguished or detected when mixed with other labels. In one preferred embodiment, each capture antibody is labelled with a distinct pattern of fluorochromes so they can be colorimetrically distinguished from one another.

Once the test antibody mixture is created, it is placed into multiple wells of, for example, a microtiter plate. In this example, the same antibody mixture would be placed in each of 50 microtiter wells and the mixture in each well would then be incubated with the target antigen as a first step in the competition assay. After incubation with the target antigen, a single probe antibody selected from the original set of 50 antibodies is added to each well. In this example, only one probe antibody is added to each reference antibody mixture. If any labelled reference antibody in the well binds to the target antigen at the same epitope as the probe antibody, they will compete with one another for the epitope binding site.

It is understood by one of skill in the art that embodiments of the invention are not limited to only adding a single probe antibody to each well. Other methods wherein multiple probe antibodies, each one distinguishably labelled from one another, are added to the mixture are contemplated.

In order to determine whether the probe antibody has bound to any of the 50 labelled reference antibodies in the well, a labelled detection antibody is added to each of the 50 reactions. In one embodiment, the labelled detection antibody is a differentially labelled version of the same antibody used as the capture antibody. Thus, for example, the detection antibody can be a mouse anti-human IgG antibody or a anti-human IgKappa antibody. The detection antibody will bind to, and label, the probe antibody that was placed in the well.

The label on the detection antibody permits detection and measurement of the amount of probe antibody bound to a complex formed by a reference antibody, the antigen, and the probe antibody. This complex serves as a measurement of the competition between the probe antibody and the reference antibody. The detection antibody may be labelled with any suitable label which facilitates detection of the secondary antibody. For example, a detection antibody may be labelled with biotin, which facilitates fluorescent detection of the probe antibody when streptavidin-phycoerythrin (PE) is added. The detection antibody may be labelled with any label that uniquely determines its presence as part of a complex, such as biotin, digoxygenin, lectin, radioisotopes, enzymes, or other labels. If desired, the label may also facilitate isolation of beads or other surfaces with antibody-antigen complexes attached.

The amount of labelled detection antibody bound to each uniquely labelled reference antibody indicates the amount of bound probe antibody, and the labelled detection antibody is bound to the probe antibody bound to antigen bound to labelled reference antibody. Measuring the amount of labelled detection antibody bound to each one of the 50 labelled reference antibodies indicates the amount of bound probe antibody can be obtained, where the amount of bound probe antibody is an indicator of the similarity or dissimilarity of the epitope recognition properties of the two antibodies (probe and reference). If a measurable amount of the labelled detection antibody is detected on the labelled reference antibody-antigen complex, that is understood to indicate that the probe antibody and the reference antibody do not bind to the same epitope on the antigen. Conversely, if little or no measurable detection antibody is detected on the labelled reference antibody-antigen complex, then it is understood to indicate that the probe antibody for that reaction bound to very similar or identical epitopes on the antigen. If a small amount of detection antibody is detected on the reference antibody-antigen complex, that is understood to indicate that the reference and probe antibodies may have similar but not identical epitope recognition properties, e.g., the binding of the reference antibody to its epitope interferes with but does not completely inhibit binding of the probe antibody to its epitope.

Another aspect of the present invention provides a method for detecting both the reference antibody and the amount of probe antibody bound to an antigen. If antibody complexes containing different reference antibodies have been mixed, then the unique property provided by the unique labels on the capture antibody can be used to identify the reference antibody coupled to that bead. Preferably, that distinct property is a unique emission spectrum.

The amount of probe antibody bound to any reference antibody can be determined by measuring the amount of detection label bound to the complex. The detection label may be a labelled detection antibody bound to probe antibody bound to the complex, or it may be a label attached to the probe antibody. Thus, the epitope recognition properties of both a reference antibody and a probe antibody can be measured by using a comparative measure of the competition between the two antibodies for an epitope.

Conditions for optimizing procedures can be determined by empirical methods and knowledge of one of skill in the art. Incubation time, temperature, buffers, reagents, and other factors can be varied until a sufficiently strong or clear signal is obtained. For example, the optimal concentration of various antibodies can be empirically determined by one of skill in the art, by testing antibodies and antigens at different concentrations and looking for the concentration that produces the strongest signal or other desired result. In one embodiment, the optimal concentration of primary and secondary antibodies—that is, antibodies to be binned—is determined by a double titration of two antibodies raised against different epitopes of the same antigen, in the presence of a negative control antibody that does not recognize the antigen.

Assays Using Colored Beads

In a preferred embodiment, large numbers of antibodies are simultaneously screened for their epitope recognition properties in a single assay using color-coded microspheres or beads to identify multiple reactions in a single tube or well, preferably using a system available from Luminex Corporation (Luminex Corp, Austin Tex.), and most preferably using the Luminex 100 system. Preferably, the MCAB assay is carried out using Luminex technology. In another preferred embodiment, up to 100 different antibodies to be tested are bound to Luminex beads with 100 distinct colors. This system provides 100 different sets of polystyrene beads with varying amounts of fluorochromes embedded. This gives each set of beads a distinct fluorescent emission spectrum and hence a distinct color code.

To characterize the binding properties of antibodies using the Luminex 100 system, beads are coated with a capture antibody which is covalently attached to each bead; preferably a mouse anti-human IgG or anti-human IgKappa monoclonal antibody is used. Each set of beads is then incubated in a well containing a reference antibody to be characterized (e.g., containing hybridoma supernatant) such that a complex if formed between the bead, the capture antibody, and the reference antibody (henceforth, a "reference antibody-bead" complex) which has a distinct fluorescence emission spectrum and hence, a color code, that provides a unique label for that reference antibody.

In this preferred embodiment, each reference antibody-bead complex from each reaction with each reference antibody is mixed with other reference antibody-bead complexes to form a mixture containing all the reference antibodies being tested, where each reference antibody is uniquely labelled by being couple to a bead. The mixture is aliquotted into as many wells of a 96-well plate as is necessary for the experiment. Generally, the number of wells will be determined by the number of probe antibodies being tested, along with various controls. Each of these wells containing an aliquot of the mixture of reference antibody-bead complexes is incubated first with antigen and then probe antibody (one of the antibodies to be characterized), and then detection antibody (a labelled version of the original capture antibody), where the detection antibody is used for detection of bound probe antibody. In a preferred embodiment, the detection antibody is a biotinylated mouse anti-human IgG monoclonal antibody. This process is illustrated in FIG. 1.

In the illustrative embodiment presented in FIG. 1, each reference antibody is coupled to a bead with distinct emission spectrum, where the reference antibody is coupled through a mouse anti-human monoclonal capture antibody, forming a uniquely labelled reference antibody. The entire set of uniquely labelled reference antibodies is placed in the well of a multiwell microtiter plate. The set of reference antibodies are incubated with antigen, and then a probe antibody is added to the well. A probe antibody will only bind to antigen that is bound to a reference antibody that recognizes a different epitope. Binding of a probe antibody to antigen will form a complex consisting of a reference antibody coupled to a bead through a capture antibody, the antigen, and the bound probe antibody. A labelled detection antibody is added to detect bound probe antibody. Here, the detection antibody is labelled with biotin, and bound probe antibody is detected by the interaction of streptavidin-PE and the biotinylated detection antibody. As shown in FIG. 1, Antibody #50 is used as the probe antibody, and the reference antibodies are Antibody #50 and Antibody #1. Probe Antibody #50 will bind to antigen that is bound to reference Antibody #1 because the antibodies bind to different epitopes, and a labelled complex can be detected. Probe antibody #50 will not bind to antigen that is bound by reference antibody #50 because both antibodies are competing for the same epitope, such that no labelled complex is formed.

In this embodiment, after the incubation steps are completed, the beads of a given well are aligned in a single file in a cuvette and one bead at a time passes through two lasers. The first laser excites fluorochromes embedded in the beads, identifying which reference antibody is bound to each bead. A second laser excites fluorescent molecules bound to the bead complex, which quantifies the amount of bound detection antibody and hence, the amount of probe antibody bound to the antigen on a reference antibody-bead complex. When a strong signal for the detection antibody is measured on a bead, that indicates the reference and probe antibodies bound to that bead are bound to different sites on the antigen and hence, recognize different epitopes on the antigen. When a weak signal for the bound detection antibody is measured on a bead, that indicates the corresponding reference and probe antibodies compete for the same epitope. This is illustrated in FIG. 1. A key advantage of this embodiment is that it can be carried out in high-throughput mode, such that multiple competition assays can be simultaneously performed in a single well, saving both time and resources.

The assay described herein may include measurements of at least one additional parameter of the epitope recognition properties of primary and secondary antibodies being characterized, for example the effect of temperature, ion concentration, solvents (including detergent) or any other factor of interest. One of skill in the relevant art can use the present disclosure to develop an experimental design that permits the testing of at least one additional factor. If necessary, multiple replicates of an assay may be carried out, in which factors such as temperature, ion concentration, solvent, or others, are varied according to the experimental design. When additional factors are tested, methods of data analysis can be adjusted accordingly to include the additional factors in the analysis.

Data Analysis

Another aspect of the present invention provides processes for analyzing data generated from at least one assay, preferably from at least one high throughput assay, in order to identify antibodies having similar and dissimilar epitope recognition properties. A comparative approach, based on comparing the epitope recognition properties of a collection of antibodies, permits identification of those antibodies having similar epitope recognition properties, which are likely to compete for the same epitope, as well as the identification of those antibodies having dissimilar epitope recognition properties, which are likely to bind to different epitopes. In this way, antibodies can be categorized, or "binned" based on which epitope they recognize. A preferred embodiment provides the Competitive Pattern Recognition (CPR) process for analyzing data generated by a high throughput assay. More preferably, CPR is used to analyze data generated by the Multiplexed Competitive Antibody Binning (MCAB) high-throughput competitive assay. Application of data analysis processes as disclosed and claimed herein makes it possible to eliminate redundancy by identifying the distinct binding specificities represented within a pool of antigen-specific antibodies characterized by an assay such as the MCAB assay.

A preferred embodiment of the present invention provides a process that clusters antibodies into "bins" or categories representing distinct binding specificities for the antigen target. In yet another preferred embodiment, the CPR process is applied to data representing the outcomes of the MCAB high-throughput competition assay in which every antibody competes with every other antibody for binding sites on antigen molecules. Embodiments carried out using different data sets of antibodies generated from XenoMouse® animals provide a demonstration that application of the process of the present invention produces consistent and reproducible results.

The analysis of data generated from an experiment typically involves multi-step operations to normalize data across different wells in which the assay has been carried out and cluster data by identifying and classifying the competition patterns of the antibodies tested. A matrix-based computational process for clustering antibodies is then performed based on the similarity of their competition patterns, wherein the process is applied to classify sets of antibodies, preferably antibodies generated from hybridoma cells.

Antibodies that are clustered based on the similarity of their competition patterns are considered to bind the same epitope or similar epitopes. These clusters may optionally be displayed in matrix format, or in "tree" format as a dendrogram, or in a computer-readable format, or in any data-input-device-compatible format. Information regarding clusters may be captured from a matrix, a dendrogram or by a computer or other computational device. Data capture may be visual, manual, automated, or any combination thereof.

As used herein, the term "bin" may be used as a noun to refer to clusters of antibodies identified as having similar competition according to the methods of the present invention. The term "bin" may also be used a verb to refer to practicing the methods of the present invention. The term "epitope binning assay" as used herein, refers to the competition-based assay described herein, and includes any analysis of data produced by the assay.

Steps in data analysis are described in detail in the following disclosure, and practical guidance is provided by reference to the data and results are presented in Example 2. References to the data of Example 2, especially the matrices or dendrograms generated by performing various data analysis steps on the input data of Example 2, serve merely as illustrations and do not limit the scope of the present invention in any way.

When a large number and sizes of the data sets is generated, a systematic method is needed to analyze the matrices of signal intensities to determine which antibodies have similar signal intensity patterns. By way of example, two matrices containing m rows and m columns are generated in a single experiment, where m is the number of antibodies being examined. One matrix has signal intensities for the set of competition assays in which antigen is present. The second matrix has the corresponding signal intensities for a negative control experiment in which antigen is absent. Each row in a matrix represents a unique well in a multiwell microtiter plate, which identifies a unique probe antibody. Each column represents a unique bead spectral code, which identifies a unique reference antibody. The intensity of signal detected in each cell in a matrix represents the outcome of an individual competition assay involving a reference antibody and a probe antibody. The last row in the matrix corresponds to the well in which blocking buffer is added instead of a probe antibody. Similarly, the last column in the matrix corresponds to the bead spectral code to which blocking buffer is added instead of reference antibody. Blocking buffer serves as a negative control and determines the amount of signal present when only one antibody (of the reference-antibody-probe-antibody pair) is present.

Similar signal intensity value patterns for two rows indicate that the two probe antibodies exhibit similar binding behaviors, and hence likely compete for the same epitope. Likewise, similar signal intensity patterns for two columns indicate that the two reference antibodies exhibit similar binding behaviors, and hence likely compete for the same epitope. Antibodies with dissimilar signal patterns likely bind to different epitopes. Antibodies can be grouped, or "binned," according to the epitope that they recognize, by grouping together rows with similar signal patterns or by grouping together columns with similar signal patterns. Such an assay described above is referred to as an epitope binning assay.

Program to Apply Competitive Pattern Recognition (CPR) Process

One aspect of the present invention provides a program to apply the CPR process having two main steps: (1) normalization of signal intensities; and (2) generation of dissimilarity matrices and clustering of antibodies based on their normalized signal intensities. It is understood that the term "main step" encompasses multiple steps that may be carried as necessary, depending on the nature of the experimental material used and the nature of the data analysis desired. It is also understood that additional steps may be practiced as part of the present invention.

Background Normalization of Signal Intensities

Input data is subjected to a series of preprocessing steps that improve the ability to detect meaningful patterns. Preferably, the input data comprises signal intensities stored in a two dimensional matrix, and a series of normalization steps are carried out to eliminate sources of noise or signal bias prior to clustering analysis.

The input data to be analyzed comprises the results from a complete assay of epitope recognition properties. Preferably, results comprise signal intensities measured from an assay carried out using labelled secondary antibodies. More preferably, results using the MCAB assay are analyzed as described herein. Two input files are generated: one input file from an assay in which antigen was added; and a second input file from an assay in which antigen was absent. The experiment in which antigen is absent serves as a negative control allowing one to quantify the amount of binding by the labelled antibodies that is not to the antigen. Preferably, each combination of primary antibody and secondary antibody being tested was assayed in the presence and absence of antigen, such that each combination is represented in both sets of input data. Even more preferably, the assay is carried out using the procedures for assaying epitope recognition properties of multiple antibodies using a multi-well format disclosed elsewhere in the present disclosure.

The input data normally comprises signal intensities stored in a two dimensional matrix. First, the matrix corresponding to the experiment without antigen (negative control) experiment, $A_B$, is subtracted from the matrix corresponding to the experiment with antigen, $A_E$ to give the background normalized matrix given by $A_N = A_E - A_B$. This subtraction step eliminates background signal that is not due to binding of antibodies to antigen. The above matrices are of dimension $(m+1) \times (m+1)$ where m is the number of antibodies to be clustered. The last row and the last column contain intensity values for experiments in which blocking buffer was added in place of a probe antibody or reference antibody, respectively.

In an illustrative embodiment, FIGS. 8A and 8B illustrate the intensity matrices generated in the embodiment disclosed in Example 2, which are used as input data matrices for subsequent steps in data analysis. FIG. 8A is the intensity matrix for an experiment conducted with antigen, and FIG. 8B is the intensity matrix for the same experiment conducted without antigen. Each row in the matrix corresponds to the signal intensities for the different beads in one well, where each well represents a unique detecting antibody. Each column represents the signal intensities corresponding to the competition of a unique primary antibody with each of the secondary antibodies. Each cell in the matrix represents an individual competition assay for a different pair of primary and secondary antibodies. In assays of epitope recognition properties, addition of blocking buffer in place of one of the antibodies serves as a negative control. In the embodiment illustrated by FIGS. 8A and 8B, the last row in the matrix corresponds to the well in which blocking buffer is added in place of a secondary antibody, and the last column in the matrix corresponds to the beads to which blocking buffer is added in place of primary antibody. Other arrangements of cells within a matrix can be used to practice aspects of the present invention, as one of skill in the relevant art can design data matrices having other formats and adapt subsequent manipulations of these data matrices to reflect the particular format chosen.

A difference matrix can be generated by subtracting the matrix corresponding to values obtained from the experiment without antigen from the matrix corresponding to values obtained from the experiment with antigen. This step is performed to subtract from the total signal the amount of signal that is not attributed to the binding of the labelled probe antibody to the antigen. This subtraction step generates a difference matrix as illustrated in FIG. 9. Following this subtraction, any antibodies that have unusually high intensities for their diagonal values relative to the other diagonal values are flagged. High values for a column both along and off the diagonal suggest that the data associated with this particular bead may not be reliable. The antibodies corresponding to these columns are flagged at this step and are considered as individual bins.

Elimination of Background Signals Due to Nonspecific Binding: Normalization of Signal Intensities within Rows or Columns of the Matrix In some cases, there is a significant disparity in the overall signal intensities between different rows or columns in the background-normalized signal intensity matrix. Row variations are likely due to variations in intensity from well to well, while column variation is likely due to the variation in the affinities and concentrations of different probe antibodies. In accordance with one aspect of the present invention, there is often a linear correlation between the blocking buffer values of the rows or columns, and the average signal intensity values of the rows or columns. If an intensity variation is observed, an additional step of row and/or column normalization is performed as described below.

Figure 2A:
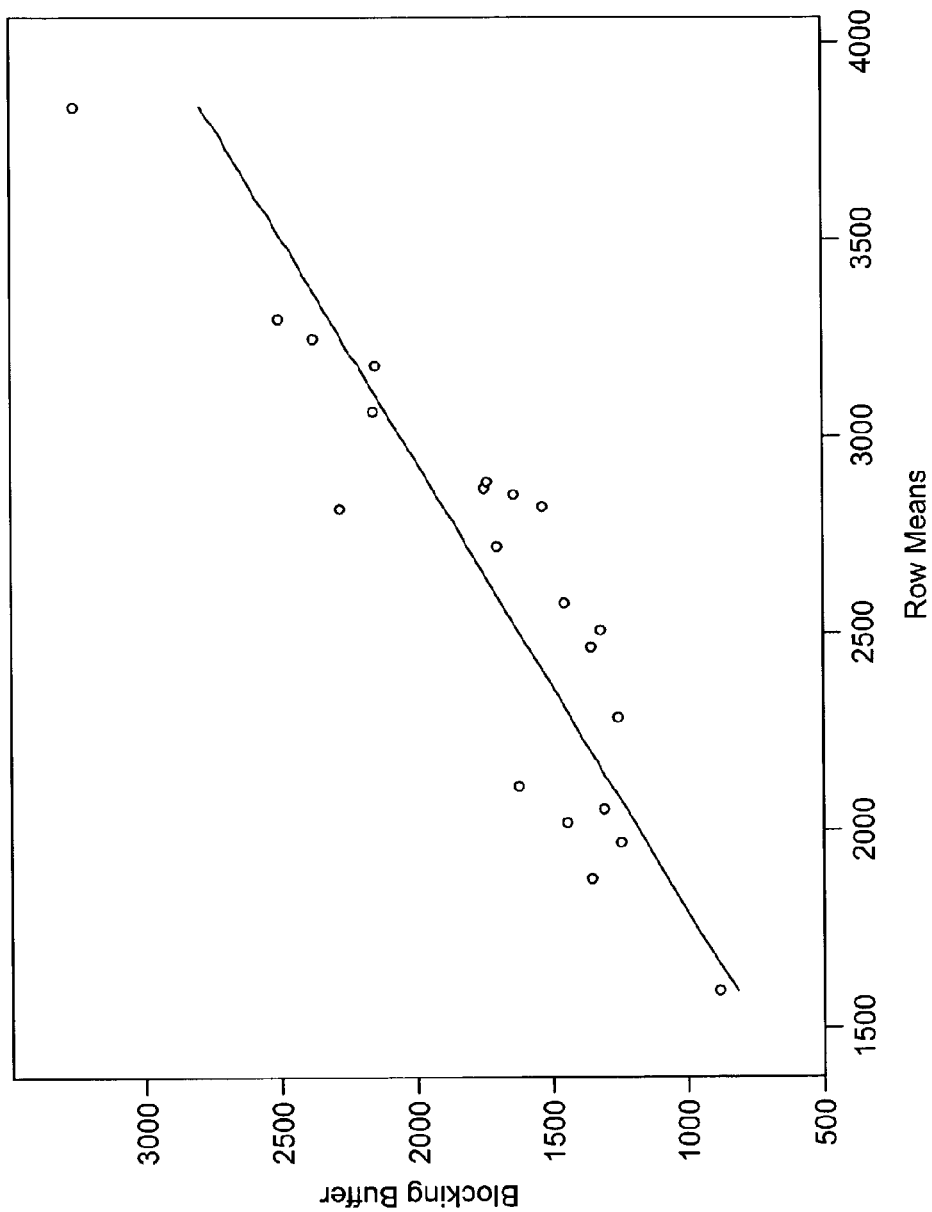
FIG. 2A. Correlation between blocking buffer intensity and average intensity within rows. Blocking buffer intensity value for each row (y-axis) plotted against the average intensity value of the row with blocking buffer value omitted (x-axis). Fitting a line to the data shows a strong linear correlation between the blocking buffer values and the average intensity values of the rest of the row.
Figure 2B:
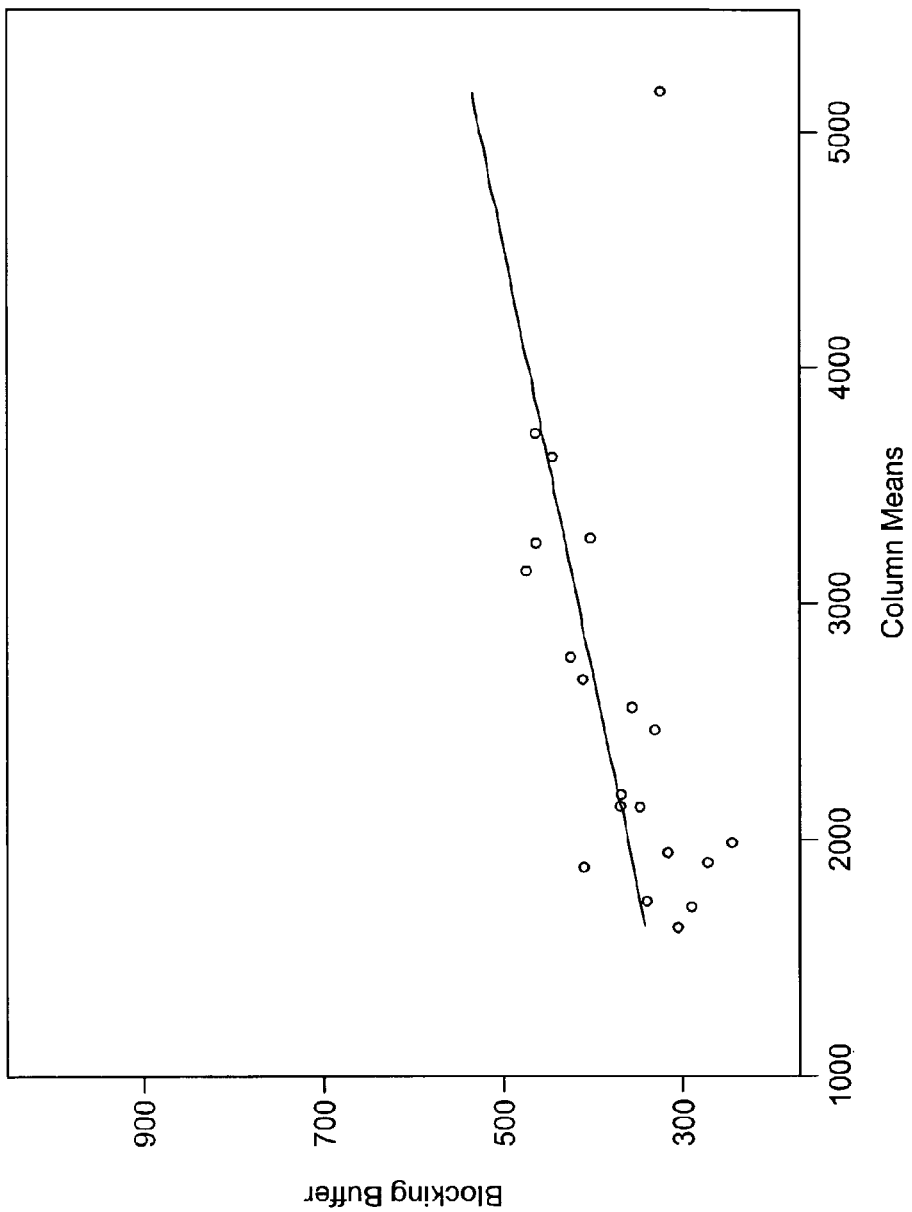
FIG. 2B. Correlation between blocking buffer intensity and average intensity within columns. Blocking buffer intensity value for each column (y-axis) plotted against the average intensity value of the column with blocking buffer value omitted (x-axis). Fitting a line to the data shows a relatively weak linear correlation between the blocking buffer values and the average intensity values of the rest of the column.

Row normalization. Row normalization is performed when there are any significant well-specific signal biases, and is carried out to eliminate any "signal artifacts" that would otherwise be introduced into the data analysis. One of skill in the art can determine whether the step is desirable based on the distribution of intensity values of the blocking buffer negative controls. By way of illustration, in FIG. 2A, the blocking buffer intensity value for each row is plotted against the average intensity value (excluding the blocking buffer value) for the corresponding row. The plot in FIG. 2A shows a clear linear correlation between the blocking buffer values and the average intensity value for a row. This figure shows that there is a well-specific signal bias in the samples being analyzed, and that the intensity value for the blocking buffer correlates to the overall signal intensity within a row. The different intensity biases seen in the different rows is likely due in part to the variation in affinity for the secondary antibodies for the antigen as well as the concentration variations of these secondary antibodies. Note that FIG. 2B shows that, for the same embodiment, there is weaker correlation between the blocking buffer intensity values for the columns and the average column intensity values.

For intensity variations in rows, the intensities of each row in the matrix are adjusted by dividing each value in a row by the blocking buffer intensity value for that row. In the case where blocking buffer data is absent, each row value is divided by the average intensity value for the row. In an embodiment applying the CPR process, the intensity-normalized matrix is given by $$A_I(i, j) = \frac{A_N(i, j)}{I(k)} \quad 1 \le i, j \le m + 1$$

where I is a vector containing the blocking buffer or average intensities and k=i if normalization is done with respect to rows.

Column normalization. In this final pre-processing step, each column in the row normalized matrix (that was not flagged at the step the difference matrix was generated) is divided by its corresponding diagonal value. The cells along the diagonal represent competition assays for which the primary and secondary antibodies are the same. Ideally, values along the diagonal should be small as two copies of the same antibody should compete for the same epitope. The division of each column by its corresponding diagonal is done to measure each intensity relative to an intensity that is known to reflect competition—i.e., competition of an antibody against itself.

For intensity variations in columns, the intensities of each column in the matrix are adjusted by dividing each value in a column by the blocking buffer intensity value for that row. In the case where blocking buffer data is absent, each column value is divided by the average intensity value for the column. In an embodiment applying the CPR process, the intensity-normalized matrix is given by $$A_I(i, j) = \frac{A_N(i, j)}{I(k)} \quad 1 \le i, j \le m + 1$$

where I is a vector containing the blocking buffer or average intensities and k=j if normalization is done with respect to columns.

Setting threshold values prior to row or column normalization. To prevent artificial inflation of low signal values in this normalization step, all blocking buffer values that are below a minimum user-defined threshold value are flagged and then adjusted to the user-defined threshold value which represents the lowest reliable signal intensity value, prior to row or column division. This threshold is set based on a histogram of the signal intensities. This normalization step adjusts for variations in intensity from well to well.

By way of example, FIG. 17 illustrates an adjusted difference matrix for the data of Example 2, wherein the minimum reliable signal intensity is set to 200 intensity units. Each row in the matrix is adjusted by dividing it by the last intensity value in the row. As noted above, the last intensity value in each row corresponds to the intensity value for beads to which blocking buffer is added in place of primary antibody. This step adjusts for the well-to-well variation in intensity values across the row. FIG. 18 illustrates a row normalized matrix for the data of Example 2.

Further by way of example, FIG. 2A presents data from an embodiment in which the blocking buffer intensity value for each row was plotted against the average intensity value for the corresponding row. This plot shows a linear correlation between the blocking buffer values and the average intensity value for a row, and suggests that there are well-specific intensity biases. These biases may be partially due to the variation in affinity for the probe antibodies for the antigen and the concentration variations of the probe antibodies. FIG. 2B presents data from an embodiment in which the blocking buffer intensity value for each column was plotted against the average intensity value for the corresponding column.

Figure 2C:
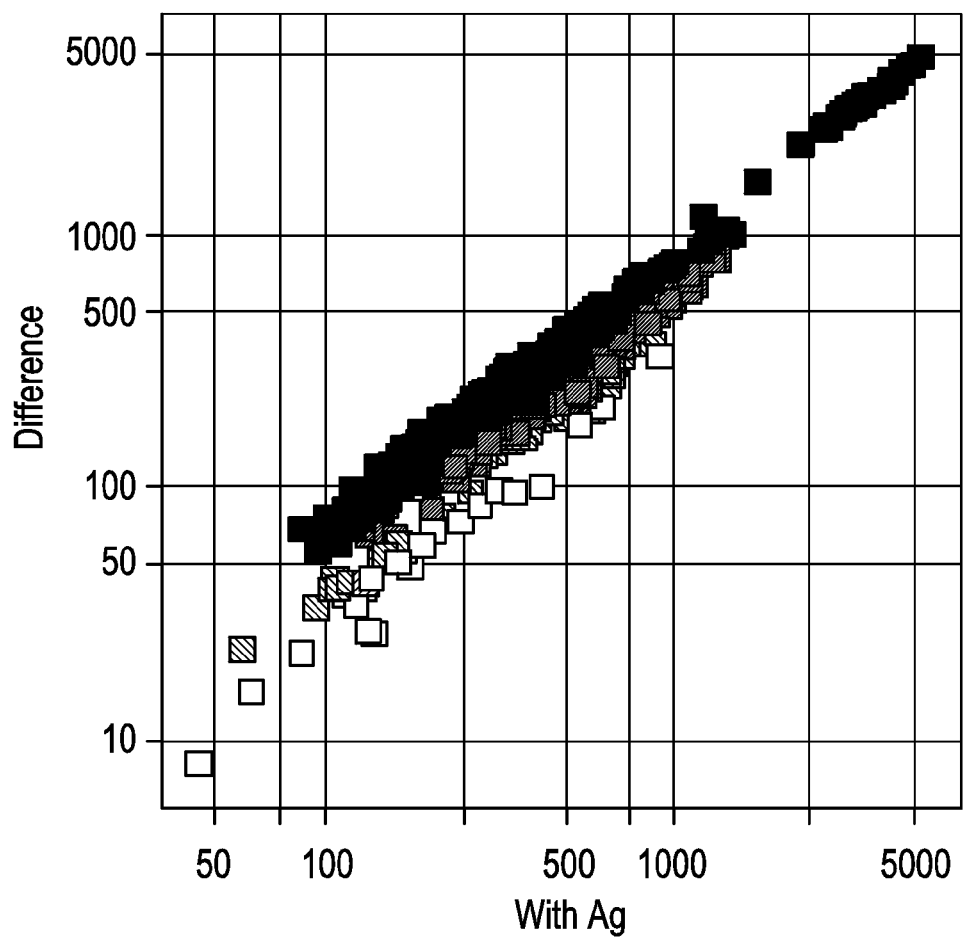
FIG. 2C. Scatter plot of intensity values for the matrix with antigen and background-normalized matrix. This plot shows a tight linear correlation (slope about 1.0) for high subtracted signal values, indicating that the background signal is minimal relative to the signal in the presence of antigen. The points are shaded according to the value of the fraction, calculated as the subtracted signal divided by the signal for the experiment with antigen present. Smaller fraction values (closer to zero) correspond to high background contribution and have light shading. Larger fraction values (closer to 1) correspond to lower background contribution and have darker shading.

In another illustrative embodiment, FIG. 2C shows a scatter plot of the background-normalized difference matrix intensities plotted against the intensities for the matrix of results from an embodiment using antigen. This plot shows a tight linear correlation (slope=1) for signal values greater than 1000, and a more scattered correlation for lower signal values. The points in FIG. 2C are shaded according to the value of a fraction calculated as the subtracted signal divided by the signal for the experiment with antigen present. Smaller fraction values (closer to zero) correspond to high background contribution and have light shading in FIG. 2C. Larger fraction values (closer to 1) correspond to lower background contribution and have darker shading. In FIG. 2C, the smaller fraction values are predominantly in the lower-left region of the scatter plot, suggesting that the contribution of background becomes less for subtracted signal values greater than 1000.

The plot shown in FIG. 2C suggests that for this embodiment, intensity values of the background-normalized matrix greater than 1000 have a low background signal contribution relative to the signal due to antigen binding. These matrix cells likely correspond to antibody pairs that do not compete for the same epitope. Conversely, intensity values below 1000 likely correspond to antibody pairs that bind to the same epitope. In accordance with one aspect of the present invention, it is expected that the intensity values along the diagonal would be small, as identical reference and probe antibodies compete for the same epitope. In the embodiment illustrated in FIG. 2C, all but one of the diagonal values of the background-normalized signal intensity matrix have intensity values below 1000.

Normalization of Signal Intensities Relative to the Baseline Signal for Probe Antibodies In a final step, data are adjusted by dividing each column or row by its corresponding diagonal value to generate the final normalized matrix given by $$A_F(i, j) = \frac{A_I(i, j)}{A_I(j, j)}.$$

Once again, to prevent artificial inflation of low signal values in this normalization step, all diagonal values below a minimum user-defined threshold value are adjusted to the threshold value before the diagonal division is done. This step is done for all columns or rows, except those that have diagonal values that are significantly high relative to other values in the column or row. This step normalizes each intensity value relative to the intensity corresponding to the individual competition assay for which the reference and probe antibodies are the same. This intensity value should be low and ideally reflect the baseline signal intensity value for the column or row, because two identical antibodies should compete for the same epitope and hence be unable to simultaneously bind to the same antigen. Columns having unusually large diagonal values are identified as outliers and excluded from the analysis. High-diagonal-intensity values may indicate that the antigen has two copies of the same epitope, e.g., when the antigen is a homodimer.

Pattern Recognition Analysis: Dissimilarity Matrices

In accordance with another aspect of the present invention, a second step in data analysis involves generating a dissimilarity matrix from the normalized intensity matrix in two steps. First, the normalized intensity values that are below a user-defined threshold value for background are set to zero (and hence represent competition) and the remaining values are set to 1, indicating that the antibodies bind to two different epitopes. Accordingly, intensity values that are less than the intensity equal to this threshold multiplied by the intensity value of the diagonal value are considered low enough to represent competition for the same epitope by the antibody pair. The dissimilarity matrix or distance matrix for a given threshold value is computed from the matrix of zeroes and ones by determining the number of positions in which each pair of rows differs. The entry in row i and column j, corresponds to the fraction of the total number of primary antibodies that differ in their competition patterns with the secondary antibodies represented in rows i and j.

By way of example, FIG. 14 shows the number of positions (out of 22 total) at which the patterns for any two antibodies differ. In this embodiment, dissimilarities are computed with respect to rows instead of columns because the row intensities have already been adjusted for well-specific intensity biases and therefore the undesirable effects of unequal secondary antibody affinities and concentrations have been factored out. In addition, the concentrations and affinities of primary antibodies are consistent between rows. However, for the columns, there is not an apparent consistent trend between average intensity and background intensity which suggests that there is not an obvious way to factor out the undesirable affects of the variable primary antibody concentrations and affinities. Therefore, comparing the signals between columns might be less valid.

Dissimilarity matrix using CPR. In an embodiment applying the CPR process, a threshold matrix, $A_T$, of zeros and ones is generated as described below. Normalized values that are less than or equal to a threshold value are set to zero to indicate that the corresponding pairs of antibodies compete for the same epitope. The threshold matrix is given by $$A_T(i, j) = \begin{cases} 0 \text{ if } A_F(i, j) \le T \\ 1 \text{ if } A_F(i, j) > T. \end{cases}$$

The remaining normalized intensity values are set to one, and the values represent pairs of antibodies that bind to different epitopes.

The dissimilarity matrix is computed from the threshold matrix by setting the value in the $i^{-th}$ row and $j^{-th}$ column of the dissimilarity matrix to the fraction of the positions at which two rows, i and j of the matrix of zeros and ones, differ. A dissimilarity matrix for a specified threshold value, T, is given by $$D_T(i, j) = \frac{m - N_1(i, j)}{m}$$

where $N_1$ is the number of ones (1s) present when the $i^{-th}$ and $j^{-th}$ rows are summed.

By way of example, for the matrix shown in Table 1 below, the dissimilarity value corresponding to the first and second rows is 0.4, because the number of positions at which the two rows differ is 2 out of 5. For an ideal experiment, the dissimilarity matrix that is generated based on a comparison of rows of the original signal intensity matrix, should be the same as the dissimilarity matrix that is generated based on the comparison of columns.

TABLE 1

Matrix Used to Compute Dissimilarity Values

|   | A | B | C | D | E |
|---|---|---|---|---|---|
| A | 0 | 1 | 1 | 1 | 0 |
| B | 1 | 1 | 1 | 0 | 0 |

TABLE 1-continued

Matrix Used to Compute Dissimilarity Values

|   | A | B | C | D | E |
|---|---|---|---|---|---|
| C | 1 | 1 | 1 | 1 | 1 |
| D | 1 | 1 | 1 | 0 | 1 |
| E | 1 | 0 | 1 | 1 | 0 |

Effect of Calculating Dissimilarity Matrices at Multiple Threshold Values

Figure 4:
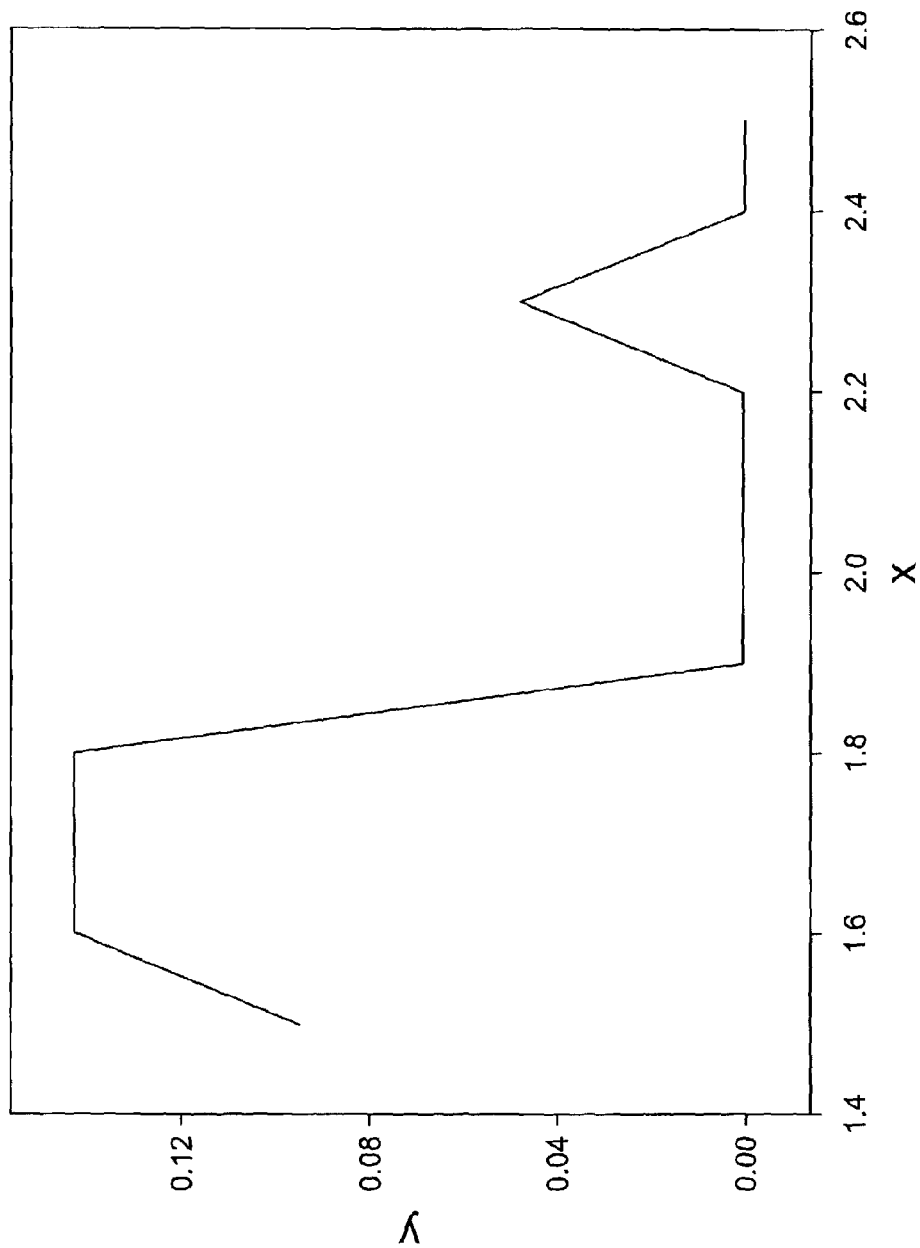
FIG. 4. Dissimilarity vs. background value: effect of choice of threshold cutoff value. The figure shows the amount of dissimilarity between antibodies 2.1 and 2.25 calculated at various threshold values. The amount of dissimilarity represents the value for the dissimilarity matrix for the entry corresponding to the two antibodies, Ab 2.1 and Ab 2.25 for a series of dissimilarity matrices computed using different threshold values. Here, the x-axis is the threshold value, and the y-axis is the dissimilarity value calculated using that threshold cutoff value.

If desired, the process of generating dissimilarity matrices is repeated for background threshold values incremented inclusively between two user-defined threshold values which represent lower and upper threshold values for intensity (where the threshold value is as described above). The dissimilarity matrices generated over a range of background threshold values is averaged and used an input to the clustering algorithm. The process of averaging over several thresholds is performed to minimize the sensitivity of the final dissimilarity matrix to any one particular choice for the threshold value. The effect of variation of the threshold value on the apparent dissimilarity is illustrated by FIG. 4, which shows the fraction of dissimilarities for a pair of antibodies (2.1 and 2.25) as a function of the threshold value for threshold values ranging between 1.5 and 2.5. As the threshold value changes from 1.8 to 1.9 the amount of dissimilarity between the signal patterns for the two antibodies changes substantially from 15% to nearly 0%. This figure shows how the amount of dissimilarity between the signal patterns for a pair of antibodies may be sensitive to one particular choice for a cutoff value, as it can vary substantially for different threshold values. The sensitivity is mitigated by taking the average dissimilarity value over a range of different threshold values.

Calculating dissimilarity matrices at multiple threshold values using CPR. In a preferred embodiment, the process of computing dissimilarity matrices using CPR is repeated for several incremental threshold values within a user-defined range of values. The average of these dissimilarity matrices is computed and used as input to the clustering step where the average is computed as $$D_{Ave}(i,j) = \frac{\sum_T D_T(i,j)}{N_T}$$

where $N_T$ is the number of different thresholds to be averaged.

This process of averaging over several thresholds is done to minimize the sensitivity of the dissimilarity matrix to a particular cutoff value for the threshold.

Dissimilarity Matrices from Multiple Experiments

If there are input data sets for more than one experiment, normalized intensity matrices are first generated as described above for each individual experiment. Normalized values above a threshold value (typically set to 4) are then set to this threshold value. Setting the high-intensity values to the threshold value is done to prevent any single intensity value from having too much weight when the average normalized intensity values are computed for that cell. The average intensity matrix is computed by taking individual averages over all data points for each antibody pair out the group consisting of antibodies that are in at least one of the input data sets. Antibody pairs for which there are no intensity values are flagged. The generation of the dissimilarity matrix is as described above with the exception that the entry in row i and column j corresponds to the fraction of the positions at which two rows, i and j differ out of the total number of positions for which both rows have an intensity value. If the two rows have no such positions, then the dissimilarity value is set arbitrarily high and flagged.

Clustering of Antibodies Based on Their Normalized Signal Intensities

Another aspect of the present invention provides processes for clustering antibodies based on their normalized signal intensities, using various computational approaches to identify underlying patterns in complex data. Preferably, any such process utilizes computational approaches developed for clustering points in multidimensional space. These processes can be directly applied to experimental data to determine epitope binding patterns of sets of antibodies by regarding the signal levels for the $n^2$ competition assays of n probe antibodies in n sampled reference antibodies as defining n points in n-dimensional space. These methods can be directly applied to epitope binning by regarding the signal levels for the competition assays of each secondary antibody with all of the n different primary antibodies as defining a point in n-dimensional space.

Results of clustering analysis can be expressed using visual displays. In addition or in the alternative, the results of clustering analysis can be captured and stored independently of any visual display. Visual displays are useful for communicating the results of an epitope binning assay to at least one person. Visual displays may also be used as a means for providing quantitative data for capture and storage. In one preferred embodiment, clusters are displayed in a matrix format and information regarding clusters is captured from a matrix. Cells of a matrix can have different intensities of shading or patterning to indicate the numerical value of each cell; alternately, cells of a matrix can be color-coded to indicate the numerical value of each cell. In another preferred embodiment, clusters are displayed as dendrograms or "trees" and information regarding clusters is captured from a dendrogram based on branch length and height (distance) of branches. In yet another preferred embodiment, clusters are identified by automated means, and information regarding clusters is captured by an automated data analysis process using a computer or any data input device.

One approach that has proven valuable for the analysis of large biological data sets is hierarchical clustering (Eisen et al. (1998) *Proc. Natl. Acad. Sci. USA* 95:14863-14868). Applying this method, antibodies can be forced into a strict hierarchy of nested subsets based on their dissimilarity values. In an illustrative embodiment, the pair of antibodies with the lowest dissimilarity value is grouped together first. The pair or cluster(s) of antibodies with the next smallest dissimilarity (or average dissimilarity) value is grouped together next. This process is iteratively repeated until one cluster remains. In this manner, the antibodies are grouped according to how similar their competition patterns are, compared with the other antibodies. In one embodiment, antibodies are grouped into a dendrogram (sometimes called a "phylogenetic tree") whose branch lengths represent the degree of similarity between the binding patterns of the two antibodies. Long branch lengths between two antibodies indicate they likely bind to different epitopes. Short branch lengths indicate that two antibodies likely compete for the same epitope.

In a preferred embodiment, the antibodies corresponding to the rows in the matrix are clustered by hierarchical clustering based on the values in the average dissimilarity matrix using an agglomerative nesting subroutine incorporating the Manhattan metric with an input dissimilarity matrix of the average dissimilarity matrix. In an especially preferred embodiment, antibodies are clustered by hierarchical clustering based on the values in the average dissimilarity matrix using the SPLUS 2000 agglomerative nesting subroutine using the Manhattan metric with an input dissimilarity matrix of the average dissimilarity matrix. (SPLUS 2000 Statistical Analysis Software, Insightful Corporation, Seattle, Wash.)

In accordance with another aspect of the present invention, the degree of similarity between two dendrograms provides a measure of the self-consistency of the analyses performed by a program applying the CPR process. A non-limiting theory regarding similarity and consistency predicts that a dendrogram generated by clustering rows and a dendrogram generated by clustering columns of the same background-normalized signal intensity matrix should be identical, or nearly so, because: if Antibody #1 and Antibody #2 compete for the same epitope, then the intensity should be low when Antibody #1 is the reference antibody and Antibody #2 is the probe antibody, as well as when Antibody #2 is the reference antibody and Antibody #1 is the probe antibody. Likewise, when the two antibodies bind to different epitopes, the intensities should be uniformly high. By this reasoning, the degree of similarity between two rows of the signal intensity matrix should be the same as between two columns of the similarity matrix. A high level of self-consistency between row clustering and column clustering suggests that, for a given experiment, the experimental protocol described herein, practiced with the program for applying the process of the present invention, produces robust results.

In accordance with a further aspect of the present invention, the degree of overlap between two epitopes may also be inferred based on the lengths of the longest branches connecting clusters in a dendrogram. For example, if a target antigen has two distinct, completely nonoverlapping epitopes, then one would expect that an antibody binding to one of the epitopes would have an opposite signal intensity pattern from an antibody binding to another epitope. According to this reasoning, if the binding sites are nonoverlapping, the signal patterns for the set of antibodies binding one epitope should be completely anticorrelated to the signal pattern for the set of antibodies recognizing the other epitope. Hence, dissimilarity values that are close to one (1) for two different clusters suggest that the corresponding epitopes do not interfere with each other or overlap in their binding sites on the antigen.

The embodiment described in Example 2 below demonstrates how clustering results can be displayed as a dendrogram (FIG. 5) or in matrix form (FIGS. 16 and 17). The data points (values of antibodies against the ANTIGEN14 target) were grouped into a dendrogram whose branch lengths represent the degree of similarity between two antibodies, where the dendrogram was generated using the Agglomerative Nesting module of the SPLUS 2000 statistical analysis software. To facilitate comparison. In FIGS. 16 and 17, the order of the antibodies in rows and columns of the matrices is the same as the order of the antibodies as displayed from left to right under the dendrogram in FIG. 5. The individual cells are visually coded by assigning a fill pattern to cells according to their numerical value. In FIG. 16, cells with values below a lower threshold value have forward hatching. Cells with values below a lower threshold and an upper threshold have no fill pattern. Cells with values above the upper threshold have stippling. A block having cells that have no fill pattern or have forward hatching indicates that all of the antibodies corresponding to that block that recognize the same epitope. Cells with stippling correspond to antibodies that recognize different epitopes. In FIG. 17, the cells are the normalized intensity values and are also visually coded according to their value. Cells that have forward hatching have intensities below a lower threshold, cells with no fill pattern have intensities between a lower and an upper threshold, while cells with back hatching have intensities above an upper threshold. A cell with forward hatching indicates the antibodies in its corresponding row and column compete for the same epitope (as the intensity is low). A cell with back hatching corresponds to a higher intensity and is indicative that the antibodies in the corresponding row and column bind to different epitopes.

The results from this illustrative embodiment (Example 2) indicate that the processes of the present invention provide a high level of self-consistency for the data with regard to revealing whether or not two antibodies compete for the same epitope. The symmetry of the fill patterns in FIGS. 16 and 17 with respect to the diagonal clearly shows this self-consistency. The reason is that the antibodies in row A and column B are the same pair as in row B and column A. Hence, if the pair of antibodies compete for the same epitope, then the intensity should be low both when antibody A is the primary antibody and antibody B is the secondary antibody, as well as when antibody B is the primary antibody and antibody B is the secondary antibody. Therefore, the intensity for the cell of the ith row and jth column as well that for the jth row and ith column should both be low. Likewise, if these two antibodies recognize different epitopes, then both corresponding intensities should be high. Out of the approximately 200 pairs of cells in FIG. 17, only one pair showed a discrepancy where one member of the pair had an intensity below 1.5 while the other member had an intensity above 2.5. The level of self-consistency of the resulting normalized matrices produced by the algorithm provides a measure of the reliability of both the data generated as well as the algorithm's analysis of the data. The high level of self-consistency for the data set (over 99%) of antibodies against the ANTIGEN14 target suggest that the data analysis processes disclosed and claimed herein generate reliable results.

Clustering Antibodies from Multiple Experiments

Another aspect of the present invention provides a method for combining data sets to overcome limitations of experimental systems used to screen antibodies. By performing multiple experiments in which each experiment has at least x antibodies in common with each other experiment, and providing the multiple resulting data sets as input to the clustering process, it should be possible to reliably cluster very large numbers of antibodies. By having a set of m antibodies in common between the m experiments, it becomes possible to infer which cluster antibodies are likely to belong to even if they are not tested against every other antibody. This suggests that using this method for data analysis with multiple data sets, it may be possible to achieve an even higher throughput with fewer assays By way of example, the Luminex technology provides 100 unique fluorochromes, so it is possible to study 100 antibodies at most in a single experiment. The consistency of results produced by the clustering step for individual data sets and the combined data set indicate that it is possible to infer which epitope is recognized by which antibody, even if the epitope and/or antibody are not tested against every other antibody. In a preferred embodiment, the CPR process can be used to characterize the binding patterns of more than 100 antibodies by performing multiple experiments using overlapping antibody sets. By designing experiments in such a way that each experiment has a set of antibodies in common with the other experiments, the combined-average matrix will not have any missing data.

A further aspect provides that the results of data analysis for a given set of antibodies are useful to aid in the rational design of subsequent experiments. For example, if a data set for a first experiment shows well-defined clusters emerging, then the set of antibodies for a second experiment should include representative antibodies from the first set of antibodies as well as untested antibodies. This approach ensures that each set of antibodies has sufficient material to define the two epitopes, and that the sets overlap sufficiently to permit comparison between sets. By comparing the competition patterns of an untested set of antibodies in the second experiment with a sample set of known antibodies from the first experiment, it should be possible to determine whether or not the untested antibodies recognize the same epitope(s) as do the first set of antibodies. This overlapping experimental design permits reliable comparison of the competition patterns of the first set with the second set of antibodies, to determine whether the antibodies in the second experiment recognize existing epitopes, or whether they recognize one or more completely novel epitopes. Further, experiments can be iteratively designed in an optimal way, so that multiple sets of antibodies can be tested against existing and new clusters.

Analysis of Data from Multiple Experiments

Results from the embodiment described in Example 3 below, using antibodies against the ANTIGEN39 target, demonstrate that the processes disclosed and claimed herein are suitable for analyzing data from multiple experiments. In this embodiment, ANTIGEN39 antibodies were tested for binding to cell surface ANTIGEN39 antigen, where ANTIGEN39 antigen is a cell surface protein. First, normalized intensity matrices were generated for each individual experiment, wherein normalized values above a selected threshold value are set to the selected threshold value to prevent any single normalized intensity value from having too much influence on the average value for that antibody pair. A single normalized matrix was generated from the individual normalized matrices by taking the average of the normalized intensity values over all experiments for each antibody pair for which data was available. Then a single dissimilarity matrix was generated as described above, with the exception that the fraction of the positions at which two rows, i and j differ only considers the number of positions for which both rows have an intensity value.

Figure 6A:
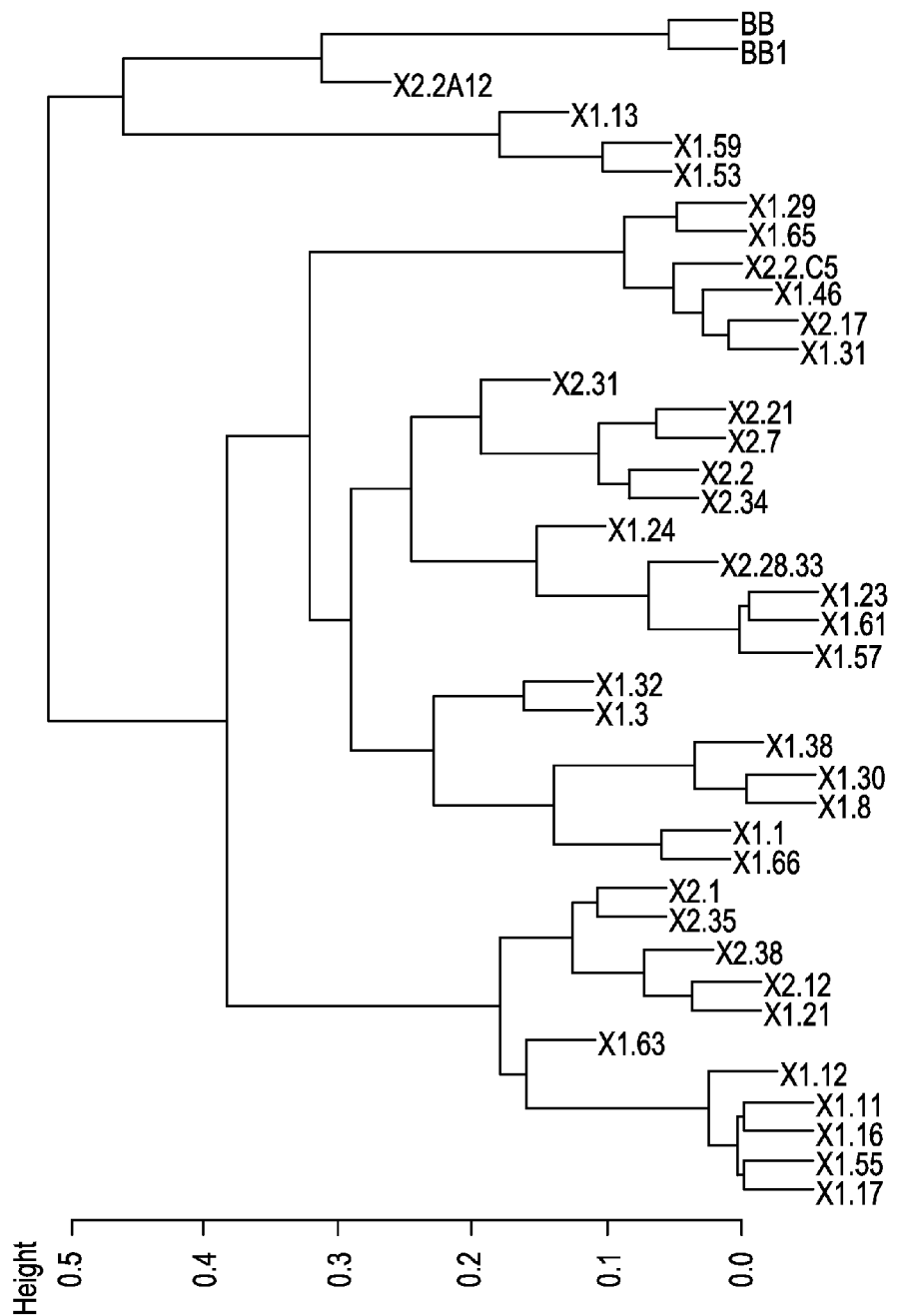
FIG. 6A. Dendrogram for the ANTIGEN39 antibodies for five input experimental data sets. The number o unique clusters of antibodies suggests that are several different epitopes, some of which may overlap. For example, the cluster containing antibodies 1.17, 1.55, 1.16, 1.11 and 1.12 and the cluster containing 1.21, 2.12, 2.38, 2.35, and 2.1 appear to be fairly closely related, with each antibody pair with the exception of 2.35 and 1.11 being no more than 25% different. This high degree of similarity across the two clusters suggests that the two different epitopes themselves have a high degree of similarity.

For five experiments using ANTIGEN39 antibodies, the clustering results for the five input data sets showed that there were a large number of clusters of varying degree of similarity, suggesting the presence of several different epitopes, some of which may overlap. This is shown in FIG. 6A, FIG. 18, FIG. 19, and FIG. 30. For example, the cluster containing antibodies 1.17, 1.55, 1.16, 1.11, and 1.12 and the cluster containing 1.21, 2.12, 2.38, 2.35, and 2.1 are fairly closely related, as each antibody pair shows no more than 25% difference, with the exception of 2.35 and 1.11. This high degree of similarity across the two clusters suggested that the two different epitopes may have a high degree of similarity The five data sets from separate experiments using ANTIGEN39 antibodies were also independently clustered, to demonstrate that the processes disclosed and claimed herein produce consistent clustering results. Clustering results are summarized in FIGS. 6B-6F and in FIGS. 20-30, where FIG. 30 summarizes the clusters for each of the individual data sets and for the combined data set with all of the antibodies for the five experiments. FIG. 6B shows the dendrogram for the ANTIGEN39 antibodies for Experiment 1: Antibodies 1.12, 1.63, 1.17, 1.55, and 2.12 consistently clustered together in this experiment as well as in other experiments as do antibodies 1.46, 1.31, 2.17, and 1.29. FIG. 6C shows the dendrogram for the ANTIGEN39 antibodies for Experiment 2: Antibodies 1.57 and 1.61 consistently clustered together in this experiment as well as in other experiments.

Figure 6E:
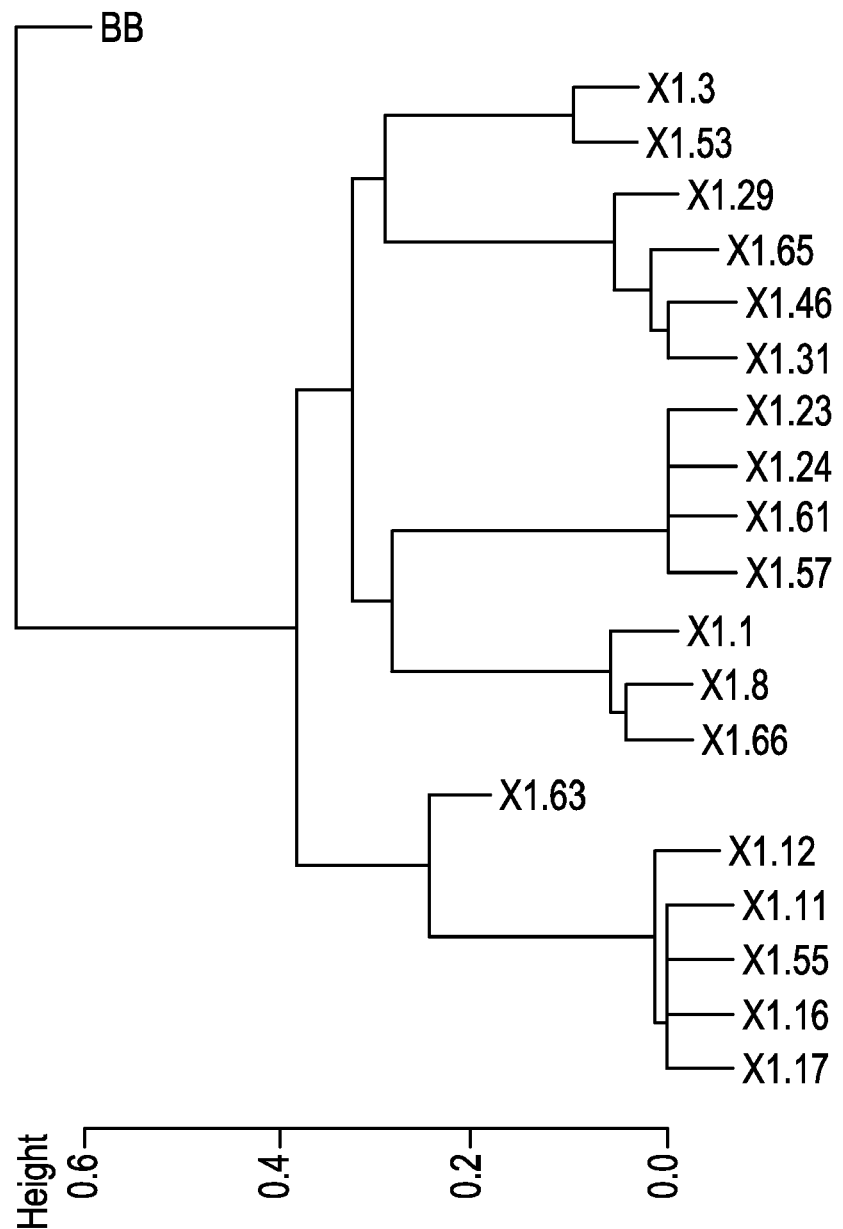
FIG. 6E. Dendrogram for the ANTIGEN39 antibodies for Experiment 4. Antibodies 1.17, 1.16, 1.55, 1.11 and 1.12 consistently cluster together in this experiment as well as in other experiments, as do antibodies 1.31, 1.46, 1.65, and 1.29, as well as antibodies 1.57 and 1.61.

FIG. 6D shows the dendrogram for the ANTIGEN39 antibodies for Experiment 3: Antibodies 1.55, 1.12, 1.17, 2.12, 1.11, and 1.21 consistently clustered together in this experiment as well as in other experiments. FIG. 6E shows the dendrogram for the ANTIGEN39 antibodies for experiment 4: Antibodies 1.17, 1.16, 1.55, 1.11, and 1.12 consistently clustered together in this experiment as well as in other experiments as do antibodies 1.31, 1.46, 1.65, and 1.29, as well as antibodies 1.57 and 1.61. FIG. 6F shows the dendrogram for the ANTIGEN39 antibodies for experiment 5: Antibodies 1.21, 1.12, 2.12, 2.38, 2.35, and 2.1 consistently clustered together in this experiment as well as in other experiments.

In general, the clustering algorithm produced consistent results both among the individual experiments and between the combined and individual data sets. Antibodies which cluster together or are in neighboring clusters for multiple individual data sets also cluster together or be in neighboring clusters for the combined data set. For example, cells having lighter shading indicate antibodies that consistently clustered together in the combined data set and in all of the data sets in which they were present (Experiments 1, 3, 4, and 5). These results indicate that the algorithm produces consistent clustering results both across multiple individual experiments and that it retains the consistency upon the merging of multiple data sets.

Finally, there is a high level of self-consistency for the data with regard to revealing whether or not two antibodies compete for the same epitope. The percent of antibody pairs for which the data consistently reveals whether or not they compete for the same epitope is summarized for each data set in Table 2, below, which reveals that the consistency was nearly 90% for four out of the five individual data sets as well as for the combined data set.

TABLE 2

Percent Consistency Values for ANTIGEN39 Antibody Experiments

| Experiment | % Consistency |
| --- | --- |
| 1 | 92 |
| 2 | 82 |
| 3 | 88 |
| 4 | 92 |
| 5 | 88 |
| Combined | 88 |

Consistency of Epitope Binning Results with Flow Cytometry (FACS) Results

Results from the embodiment described in Example 3 below, using antibodies against the ANTIGEN39 target further demonstrate that results generated by epitope binning according to the methods of the present invention are consistent with the results generated using flow cytometry (fluorescence-activated cell sorter, FACS). Cells expressing ANTIGEN39 were sorted by FACS, and ANTIGEN39-negative cells were used as negative controls also sorted by FACS. The cell surface binding sites recognized by antibodies from different bins represent different epitopes. FIG. 3 shows a comparison of results from antibody experiments using the anti-ANTIGEN39 antibody, with results using FACS. As shown in FIG. 3, the antibodies in a given bin are either all positive (Bins 1, 4, 5) or all negative (bins 2 and 3) in FACS, which indicates that the antibody epitope binning assay indeed bins antibodies based on their epitope binding properties. Thus, epitope binning, as described herein, provides an efficient, rapid, and reliable method for determining the epitope recognition properties of antibodies, and sorting and categorizing antibodies based on the epitope they recognize.

Alternative Data Analysis Process and Consistency of Epitope Binning with Sequence Results.

An alternative data analysis process involves subtracting the data matrix for the experiment carried out with antigen from the data matrix for the experiment without antigen to generate a normalized background intensity matrix. The value in each diagonal cell is then used as a background value for determining the binding affinity of the antibody in the corresponding column. Cells in each column the normalized background intensity matrix (the subtracted matrix) having values significantly higher than the value of the diagonal cell for that column are highlighted or otherwise noted. Generally, a value of about two times the corresponding diagonal is considered "significantly higher", although one of skill in the art can determine what increase over background is the threshold for "significantly higher" in a particular embodiment, taking into account the reagents and conditions used, and the "noisiness" of the input data. Columns with similar binding patterns are grouped as a bin, and minor differences within the bin are identified as sub-bins. This data analysis can be carried out automatically for a given set of input data. For example, input data can be stored in a computer database application where the cells in diagonal are automatically marked, and the cells in each column as compared with the numbers in diagonal are highlighted, and columns with similar binding patterns are grouped.

In a preferred embodiment using fifty-two (52) antibodies against ANTIGEN54, binning results using the data analysis process described above correlated with sequence analysis the CDR regions of antibodies binned using the MCAB competitive antibody assay. The 52 antibodies consisted of 2 or 3 clones from 20 cell lines. As expected, sequences of clones from same line were identical, so only one representative clone from each line was sequenced. The correspondence between the epitope binning results and sequence analysis of antibodies binned by this method indicates this approach is suitable for identifying antibodies having similar binding patterns. In addition, correspondence between the epitope binning results and sequence analysis of antibodies binned by this method means that the epitope binning method provides information and guidance about which antibody sequences are important in determining the epitope specificity of antibody binding.

EXAMPLES

Example 1

Assay of Epitope Recognition Properties

Generation and Preliminary Characterization of Antibodies.

Hybridoma supernatants containing antigen-specific human IgG monoclonal antibodies used for binning were collected from cultured hybridoma cells that had been transferred from fusion plates to 24-well plates. Supernatant was collected from 24-well plates for binning analysis. Antibodies specific for the antigen of interest were selected by hybridoma screening, using ELISA screening against their antigens. Antibodies positive for binding to the antigen were ranked by their binding affinity through a combination of a 96-well plate affinity ranking method and BIAcore affinity measurement. Antibodies with high affinity for the antigen of interest were selected for epitope binning These antibodies will be used as the reference and probe test antibodies in the assay.

Assay Using Luminex Beads

First, the concentration of mouse anti-human IgG (mxhIgG) monoclonal antibodies used as capture antibody to capture the reference antibody was measured, and mxhIgG antibodies were dialyzed in PBS to remove azides or other preservatives that could interfere with the coupling process. Then the mxhIgG antibodies were coupled to Luminex beads (Luminex 100 System, Luminex Corp., Austin Tex.) according to manufacturer's instructions in the Luminex User Manual, pages 75-76. Briefly, mxhIgG capture antibody at 50 µg/ml in 500 µl PBS was combined with beads at $1.25 \times 10^7$ beads/ml in 300 µl. After coupling, beads were counted using a hemocytometer and the concentration was adjusted to $1 \times 10^7$ beads/ml.

The antigen-specific antibodies were collected and screened as described above, and their concentrations were determined. Up to 100 antibodies were selected for epitope binning. The antibodies were diluted according to the following formula for linking the antibodies to up to 100 uniquely labelled beads to form labelled reference antibodies:

Total volume of the samples in each tube: $V_t=(n+1) \times 100$ µl+150 µl, where n=total number of samples including controls.

Volume of individual sample needed for dilution: $V_s=C \times V_t/C_s$, $C_s$=IgG concentration of each sample. C=0.2-0.5 µg/ml.

Samples were prepared according to the above formula, and 150 µl of each diluted sample containing a reference antibody was aliquotted into a well of a 96-well plate. Additional aliquots were retained for use as a probe antibody at a later stage in the assay. The stock of mxhIgG-coupled beads was vortexed and diluted to a concentration of 2500 of each bead per well or $0.5 \times 10^5$/ml. The reference antibodies were incubated with mxhIgG-coupled beads on a shaker in the dark at room temperature overnight.

A 96-well filter plate was pre-wetted by adding 200 µl wash buffer and aspirating. Following overnight incubation, beads (now with reference antibodies bound to mxhIgG bound to beads) were pooled, and 100 µl was aliquotted into each well of a 96-well microtiter filter plate at a concentration of 2000 beads per well. The total number of aliquots of beads was twice the number of samples to be tested, thereby permitting parallel experiments with and without antigen. Buffer was immediately aspirated to remove any unbound reference antibody, and beads were washed three times.

Antigen was added (50 µl) to one set of samples; and beads were incubated with antigen at a concentration of 1 µg/ml for one hour. A buffer control was added to the other set of samples, to provide a negative control without antigen.

All antibodies being used as probe antibodies were then added to all samples (with antigen, and without antigen). In this experiment, each antibody being used as a reference antibody was also used as a probe antibody, in order to test all combinations. The probe antibody should be taken from the same diluted solution as the reference antibody, to ensure that the antibody is used at the same concentration. Probe antibody (50 µl/well) was added to all samples and mixtures were incubated in the dark for 2 hours at room temperature on a shaker. Samples were washed three times to remove unbound probe antibody.

Detection antibody: Biotinylated mxhIgG (50 µl/well) was added at a 1:500 dilution, and the mixture was incubated in the dark for 1 hour on a shaker. Beads were washed three times to remove unbound Biotinylated mxhIgG. Streptavidin-PE at 1:500 dilution was added, 50 µl/well. The mixture was incubated in the dark for 15 minutes at room temperature on a shaker, and then washed three times to remove unbound components.

In accordance with manufacturer's instructions, the Luminex 100 and XYP base were warmed up using Luminex software. A new session was initiated, and the number of samples and the designation numbers of the beads used in the assay were entered.

Beads in each well were resuspended in 80 µl dilution buffer. The 96-well plate was placed in the Luminex based and the fluorescence emission spectrum of each well was read and recorded.

Optimization of Assay

To optimize the assay, the Luminex User's Manual Version 1.0 was initially used for guidance regarding the concentrations of beads, antibodies, and incubation times. It was determined empirically that a longer incubation time provided assured binding saturation and was more suitable for the nanogram antibody concentrations used in the assay.

Example 2

Analysis of a Single Data Set: ANTIGEN14 Antibodies

Data Input

Antibodies were assayed as described in Example 1, and results were collected. Input files consisted of input matrices shown in FIG. 8A (antigen present) and FIG. 8B (antigen absent) for a data set corresponding to a single experiment for the ANTIGEN14 target.

Normalization of ANTIGEN14 Target Data

First, the matrix corresponding to the experiment without antigen (negative control, FIG. 8B) experiment was subtracted from the matrix corresponding to the experiment with antigen (FIG. 8A), to eliminate the amount of background signal due to nonspecific binding of the labelled antibody. The difference between the two matrices is shown in FIG. 9. The column corresponding to antibody 2.42 has unusually large values both on and off the diagonal and was flagged and treated separately in the data analysis as described above.

Row Normalization

The difference matrix was adjusted by setting values below the user-defined threshold value of 200 to this threshold value as shown in FIG. 10. This adjustment was done to prevent significant artificial inflation of low signal values in subsequent normalization steps (as described above). The intensities of each row in the matrix were then normalized by dividing each row value by the row value corresponding to blocking buffer (FIG. 11). This adjusts for the well-to-well intensity variation as discussed above and illustrated in FIG. 2A.

Column Normalization

All columns except the one corresponding to antibody 2.42 were column-normalized as described above and are shown in FIG. 12.

Dissimilarity Matrix

A dissimilarity (or distance) matrix was generated in a multistep procedure. First, intensity values below the user-defined threshold (set to two times the diagonal intensity values) were set to zero and the remaining values were set to one (FIG. 13). This means that intensity values that are less than twice the intensity value of the diagonal value are considered low enough to represent competition for the same epitope by the antibody pair. The dissimilarity matrix is generated from the matrix of zeroes and ones by setting the entry in row i and column j to the fraction of the positions at which two rows, i and j differ. FIG. 14 shows the number of positions (out of 22 total) at which the patterns for any two antibodies differed for the set of antibodies generated against the ANTIGEN14 target.

A dissimilarity matrix was generated from the matrix of zeroes and ones generated from each of several threshold values ranging from 1.5 to 2.5 (times the values of the diagonals), in increments of 0.1. The average of these dissimilarity matrices was computed (FIG. 15) and used as input to the clustering algorithm. The significance of taking the average of several dissimilarity matrices is illustrated in FIG. 4. FIG. 4 shows the fraction of dissimilarities for a pair of antibodies (2.1 and 2.25) as a function of the threshold value for threshold values ranging from 1.5 to 2.5. As the threshold value changed from 1.8 and 1.9 the amount of dissimilarity between the signal patterns for the two antibodies changed substantially from 0% to nearly 15%. This figure shows how the amount of dissimilarity between the signal patterns for a pair of antibodies may be sensitive to one particular choice of cutoff value, as it can vary substantially for different threshold values.

Clustering

Hierarchical clustering. Using the Agglomerative Nesting Subroutine in SPLUS 2000 statistical analysis software, antibodies were grouped (or clustered) using the average dissimilarity matrix described above as input. In this algorithm, antibodies were forced into a strict hierarchy of nested subsets. The pair of antibodies with the smallest corresponding dissimilarity value in the entire matrix is grouped together first. Then, the pair of antibodies, or antibody-cluster, with the second smallest dissimilarity (or average dissimilarity) value is grouped together next. This process was iteratively repeated until one cluster remained.

Visualizing Clusters in Dendrograms

Figure 5:
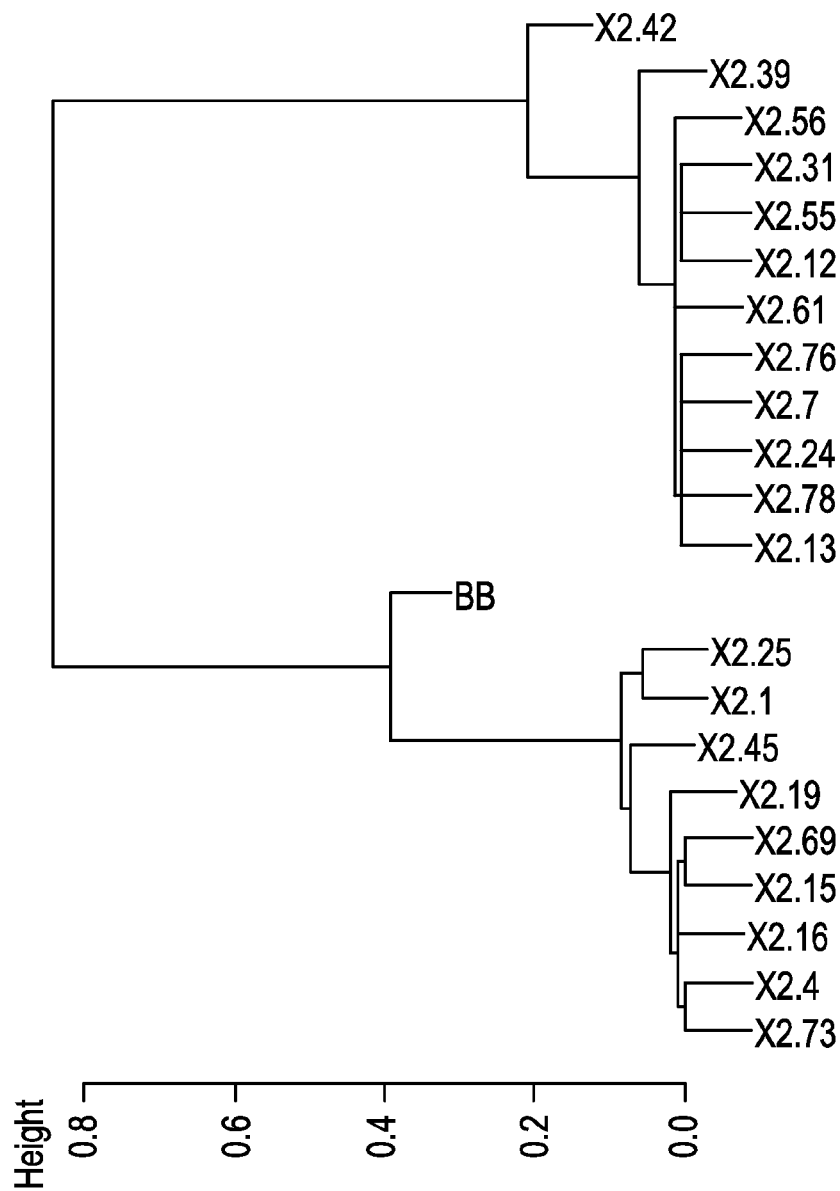
FIG. 5. Dendrogram for the ANTIGEN14 antibodies. The length of branches connecting two antibodies is proportional to the degree of similarity between the two antibodies. This figure shows that there are two very distinct epitopes recognized by these antibodies. One epitope is recognized by antibodies 2.73, 2.4, 2.16, 2.15, 2.69, 2.19, 2.45, 2.1, and 2.25. A different epitope is recognized by antibodies 2.13, 2.78, 2.24, 2.7, 2.76, 2.61, 2.12, 2.55, 2.31, 2.56, and 2.39. Antibody 2.42 does not have a pattern that is very similar to any other antibody, but has some noticeable similarity to the second cluster, although it may recognize yet a third epitope which partially overlaps with the second epitope.

The dendrogram calculated for the ANTIGEN14 target is shown in FIG. 5. The length (or height) of the branches connecting two antibodies is inversely proportional to the degree of similarity between the antibodies it binds. This dendrogram shows that there were two very distinct epitopes recognized by these antibodies. One epitope was recognized by antibodies 2.73, 2.4, 2.16, 2.15, 2.69, 2.19, 2.45, 2.1, and 2.25. A different epitope was recognized by antibodies 2.13, 2.78, 2.24, 2.7, 2.76, 2.61, 2.12, 2.55, 2.31, 2.56, and 2.39. Antibody 2.42 does not have a pattern that was very similar to any other antibody but had some noticeable similarity to the second cluster, indicating that it may recognize yet a third epitope which partially overlaps with the second epitope.

Visualizing Clusters in Matrices

This clustering of these antibodies can also be seen in FIG. 16 and FIG. 17. In FIG. 16 the rows and columns of the dissimilarity matrix were rearranged according to the order of the "leaves" or clades on the dendrogram and the individual cells were visually coded according to the degree of dissimilarity. Cells that have forward hatching correspond to antibody pairs that were very similar (less than 10% dissimilar). Cells that have no fill pattern correspond to those antibodies that were fairly similar (between 10% and 25% dissimilar). Cells that have strippling correspond to antibody pairs that were more than 25% dissimilar. The forward hatched blocks correspond to different clusters of antibodies. Excluding the blocking buffer, there appeared to be two, or possibly three, blocks corresponding to the groups of antibodies mentioned above. FIG. 16 also shows that, allowing for a slightly higher tolerance for dissimilarity, Antibody 2.42 can be considered a member of the second cluster.

In FIG. 17, the rows and columns of the normalized intensity matrix were rearranged according to the order of the leaves on the dendrogram and the individual cells were visually coded according to their normalized intensity values. Cells that have forward hatching correspond to antibody pairs that had a high intensity (at least 2.5 times greater than the background). Cells that have no fill pattern had an intensity between 1.5 and 2.5 times the background. Cells that have forward hatching correspond to intensities that were less than 1.5 times the background. When comparing the visual markings of the rows of this matrix, two very distinct patterns emerged corresponding to the two epitopes shown above. Furthermore, note that the visual coding is very symmetric with respect to the diagonal. This shows that there was a high level of self-consistency for the data with regard to revealing whether two antibodies compete for the same epitope. The reason is that if antibody A and antibody B compete for the same epitope, then the intensity should be low both when antibody A is the primary antibody and antibody B is the secondary antibody, as well as when antibody B is the primary antibody and antibody A is the secondary antibody. Therefore, the intensity for the cell of the $i^{-th}$ row and $j^{-th}$ column as well that for the $j^{-th}$ row and $i^{-th}$ column should both be low. Likewise, if these two antibodies recognized different epitopes, then both corresponding intensities should have been high. Out of the approximately 200 pairs of cells, for only one pair did one member of the pair have an intensity below 1.5 while the other member had an intensity above 2.5. The level of self-consistency of the resulting normalized matrices produced by the algorithm provided a measure of the reliability of both the data generated as well as the algorithm's analysis of the data. The high level of self-consistency for the ANTIGEN14 data set (over 99%) suggests that one can trust the results of the algorithm for this data set with a high level of confidence.

Example 3

Analysis of Multiple Data Sets: ANTIGEN39

When there are input data sets for more than one experiment, normalized intensity matrices are first generated as described above for each individual experiment. Normalized values above a threshold value (typically set to 4) are set to the corresponding threshold value. This prevents any single normalized intensity value from having too much influence on the average value for that antibody pair. A single normalized matrix is generated from the individual normalized matrices by taking the average of the normalized intensity values over all experiments for each antibody pair for which there is data. Antibody pairs with no corresponding intensity values are flagged. The generation of the dissimilarity matrix is as described above with the exception that the fraction of the positions at which two rows, i and j differ only considers the number of positions for which both rows have an intensity value. If the two rows have no such positions, then the dissimilarity value is set arbitrarily high and flagged.

Five experiments were conducted using ANTIGEN39 antibodies, using methods described in Examples 1 and 2, and throughout the description. The clustering results for the five input data sets of ANTIGEN39 antibodies are summarized in FIG. 6A, FIG. 18, FIG. 19, and Table 30. The results show that there were a large number of clusters of varying degree of similarity. This suggests there were several different epitopes, some of which may overlap. For example, the cluster containing antibodies 1.17, 1.55, 1.16, 1.11, and 1.12 and the cluster containing 1.21, 2.12, 2.38, 2.35, and 2.1 are fairly closely related (each antibody pair with the exception of 2.35 and 1.11 being no more than 25% different). This high degree of similarity across the two clusters suggests that the two different epitopes may have a high degree of similarity In order to test the algorithm's ability to produce consistent clustering results, the five data sets were also independently clustered. The clustering results for the different experiments are summarized in FIGS. 6B-6F and in FIGS. 20-30. FIG. 30 summarizes the clusters for each of the individual data sets and for the combined data set with all of the antibodies for the five experiments. FIG. 6B shows the dendrogram for the ANTIGEN39 antibodies for Experiment 1: Antibodies 1.12, 1.63, 1.17, 1.55, and 2.12 consistently clustered together in this experiment as well as in other experiments as do antibodies 1.46, 1.31, 2.17, and 1.29. FIG. 6C shows the dendrogram for the ANTIGEN39 antibodies for Experiment 2: Antibodies 1.57 and 1.61 consistently clustered together in this experiment as well as in other experiments.

FIG. 6D shows the dendrogram for the ANTIGEN39 antibodies for Experiment 3: Antibodies 1.55, 1.12, 1.17, 2.12, 1.11, and 1.21 consistently clustered together in this experiment as well as in other experiments. FIG. 6E shows the dendrogram for the ANTIGEN39 antibodies for experiment 4: Antibodies 1.17, 1.16, 1.55, 1.11, and 1.12 consistently clustered together in this experiment as well as in other experiments as do antibodies 1.31, 1.46, 1.65, and 1.29, as well as antibodies 1.57 and 1.61. FIG. 6F shows the dendrogram for the ANTIGEN39 antibodies for experiment 5: Antibodies 1.21, 1.12, 2.12, 2.38, 2.35, and 2.1 consistently clustered together in this experiment as well as in other experiments.

In general, the clustering algorithm produced consistent results both among the individual experiments and between the combined and individual data sets. Antibodies which cluster together or are in neighboring clusters for multiple individual data sets also cluster together or be in neighboring clusters for the combined data set. For example, the cells with back hatching indicate antibodies that consistently clustered together in the combined data set and in all of the data sets in which they were present (Experiments 1, 3, 4, and 5). Similarly, the cells with forward hatching indicate the antibodies that consistently clustered together in the combined data set and in Experiments 1, 4, and 5. These results indicate that the algorithm produces consistent clustering results both across multiple individual experiments and that it retains the consistency upon the merging of multiple data sets.

Finally, there is a high level of self-consistency for the data with regard to revealing whether or not two antibodies compete for the same epitope. The percent of antibody pairs for which the data consistently reveals whether or not they compete for the same epitope is summarized for each data set in Table 2, above. Table 2 reveals that the consistency was nearly 90% for four out of the five individual data sets as well as for the combined data set.

Example 4

Analysis of a Small Set of IL-8 Human Monoclonal Antibodies Using the Competitive Pattern Recognition Data Analysis Process A small set of well-characterized human monoclonal antibodies developed against IL-8, a proinflammatory mediator, was used to evaluate the program applying the CPR process. Previously, plate-based ELISAs had shown that antibodies within the set bound two different epitopes: HR26, a215, and D111 recognized one epitope, whereas K221 and a33 competed for a second epitope. Further analysis using epitope mapping studies showed that HR26, a809, and a928 bound to the same or overlapping epitopes, while a837 bound to a different epitope.

In a new experiment to determine whether the CPR process was capable of correctly clustering antibodies, the process was tested on a set of seven IL-8 antibodies, including some of the monoclonal antibodies listed above. The results are summarized in the dendrograms shown in FIG. 7A. The dendrogram on the left was generated by clustering columns, and the dendrogram on the right was generated by clustering rows of the background-normalized signal intensity matrix. Both dendrograms indicated that there were two epitopes for a dissimilarity cut-off of 0.25: one epitope recognized by HR26, a215, a203, a393, and a452, and a second epitope recognized by K221 and a33.

These results using the CPR process to cluster antibodies were consistent with the data from plate-based ELISA assays summarized above. The results obtained using the CPR process indicated that the target antigen appeared to have two distinct epitopes, confirming the results seen using plate-based ELISA assays. Using the CPR process for clustering indicated that HR26 and a215 clustered together, as did K221 and a33, again consistent with the results from plate-based ELISA assays.

Figure 7A:
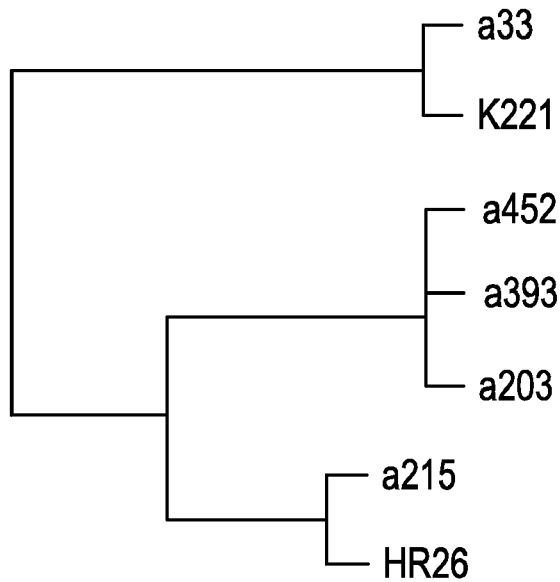
FIG. 7A. Dendrograms for a clustering of seven IL-8 monoclonal antibodies. The dendrogram on the left is generated by clustering columns, and the dendrogram on the right by clustering rows of a background-normalized signal intensity matrix. Both dendrograms indicate that there are two epitopes, using a dissimilarity cutoff of 0.25: one epitope is recognized by monoclonal antibodies HR26, a215, a203, a393, and a452; a second epitope is recognized by monoclonal antibodies K221 and a33.
Figure 7A:
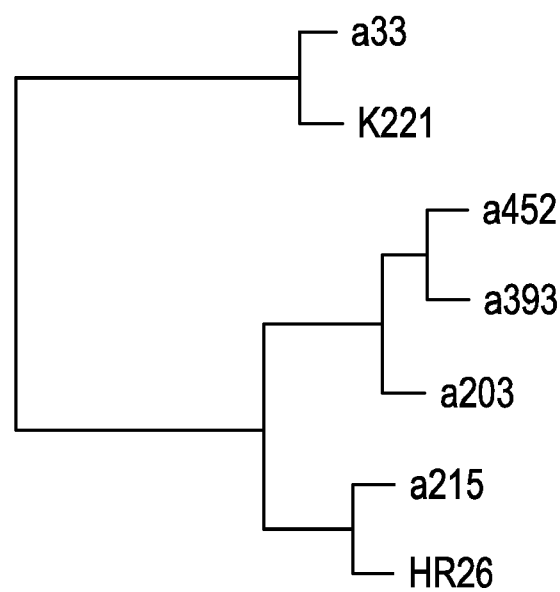

The degree of similarity between the two dendrograms provided a measure of the self-consistency of the analyses performed by this process. Ideally, the two dendrograms (the one on the left generated by clustering columns and the one on the right generated by clustering rows) should have been identical for the following reason: if Antibody #1 and Antibody #2 compete for the same epitope, then the intensity should be low when Antibody #1 is the reference antibody and Antibody #2 is the probe antibody, as well as when Antibody #2 is the reference antibody and Antibody #1 is the probe antibody. Likewise, when the two antibodies bind to different epitopes, the intensities should be uniformly high. By this reasoning, the degree of similarity between two rows of the signal intensity matrix should be the same as between two columns of the similarity matrix. In the present example, the dendrograms on the left- and right-hand side of FIG. 7A are nearly identical. In each case, the same antibodies appeared in the two clusters. This high level of self-consistency between row and column clusterings suggested that the experimental protocol, together with the process, produces robust results.

Example 5

Analysis of Multiple Data Sets of IL-8 Antibodies Using the Competitive Pattern Recognition (CPR) Data Analysis Process Multiple screening experiments using IL-8 antibodies were carried out, generating multiple data sets. Normalized intensity matrices were first generated as described above for the matrices for each individual experiment. Normalized values greater than a user-defined threshold value were set to the user-defined threshold value. High-intensity values were assigned to the threshold value to prevent any single intensity value from having too much weight when the average normalized intensity value was computed for that particular pair of antibodies in a subsequent step. The rows and columns of the average normalized intensity matrix corresponded to the set of "unique" antibodies identified using the methods of the present invention. These "unique" antibodies were identified from among all the antibodies used in all the experiments. The average intensity was computed for each cell in this matrix for which there was at least one intensity value. Cells corresponding to antibody pairs with no data were identified as missing data points. Generation of the dissimilarity matrix was as described above, except that the fraction was determined based on the number of positions at which two rows differed relative to the total number of positions for which both rows had intensity values. If the two rows had no common data, then the dissimilarity value for the corresponding cell was flagged and set arbitrarily high, so the corresponding antibodies would not be grouped together as an artifact.

Figure 7B:
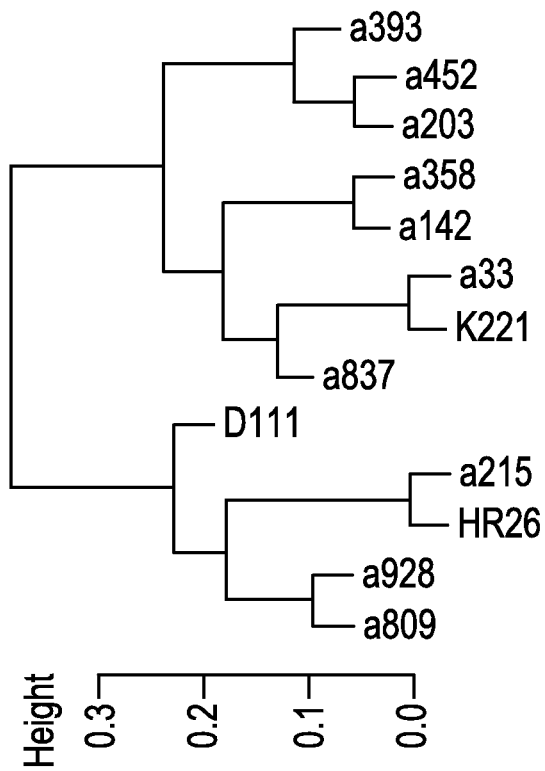
FIG. 7B. Dendrograms for IL-8 monoclonal antibodies from a combined clustering analysis merging five different experimental data sets. The dendrogram on the left was generated by clustering columns, whereas the dendrogram on the right was generated by clustering rows of the background-normalized signal intensity matrix. Both dendrograms indicate that there are two epitopes, using a dissimilarity cut-off of 0.25: one epitope is recognized by monoclonal antibodies a809, a928, HR26, a215, and D111; a second epitope is recognized by monoclonal antibodies a837, K221, a33, a142, a358, and a203, a393, and a452.
Figure 7B:
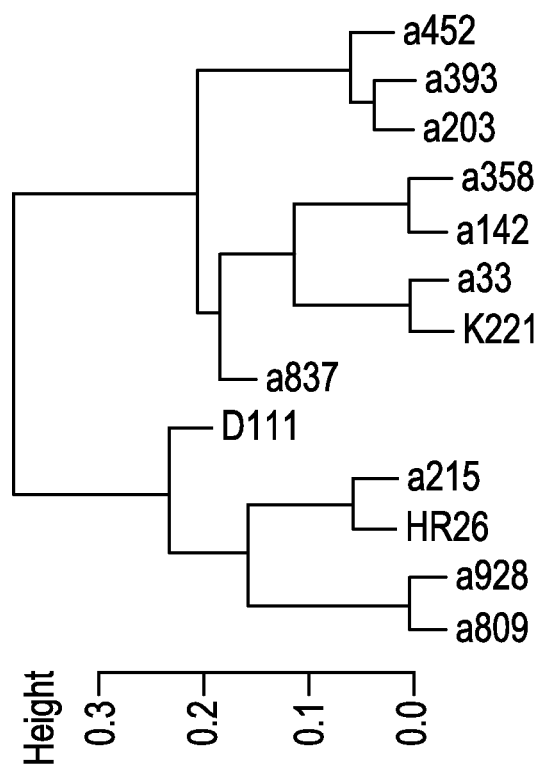

The clustering results for a set of monoclonal antibodies from five overlapping sets of monoclonal antibodies are summarized in FIG. 7B and Table 3 (below). These dendrograms corroborate the results showing there are two different epitopes on the target antigen. The first epitope is defined by monoclonal antibodies a809, a928, HR26, a215, and D111 and the second epitope is defined by monoclonal antibodies a837, K221, a33, a142, and a358, a203, a393, and a452. The lengths of the branches connecting the clusters indicated that, whereas the first cluster was very different from the other two, the second and third clusters were similar to each other.

Figure 7C:
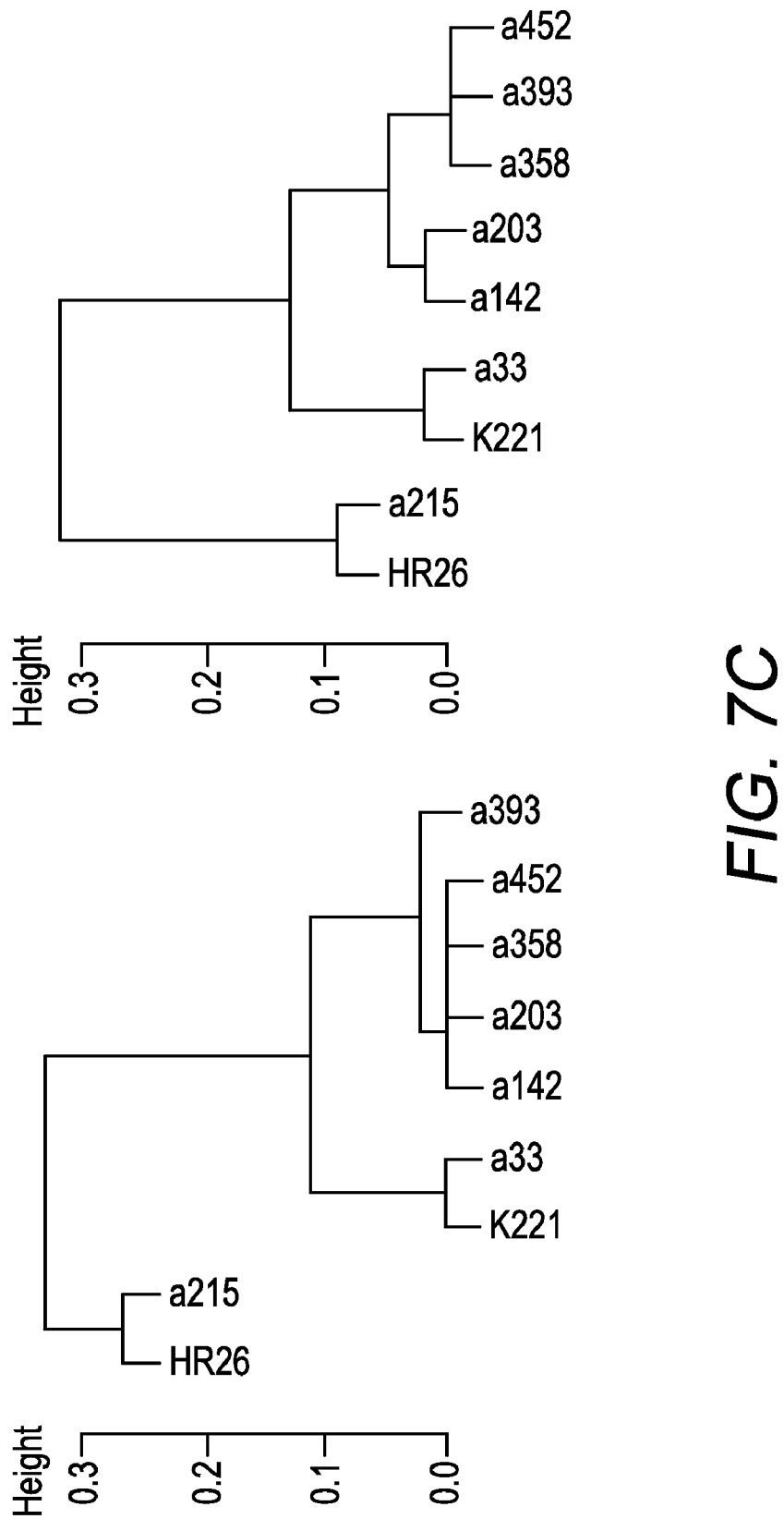
FIG. 7C. Dendrograms for a clustering of nine IL-8 monoclonal antibodies. The dendrogram on the left was generated by clustering columns, and the dendrograms on the right by clustering rows of the background-normalized signal intensity matrix. Both dendrograms indicate that there are two epitopes, using a dissimilarity cut-off of 0.25: one epitope is recognized by monoclonal antibodies HR26 and a215; a second epitope is recognized by monoclonal antibodies K221, a33, a142, a203, a358, a393, and a452.

To test the capacity of the CPR process to produce consistent results across separate experiments, the five data sets were also independently clustered. The clustering results for the different experiments are summarized in the dendrograms shown in FIGS. 7A, 7B, 7C, and Table B. These dendrograms demonstrated that the CPR clustering process produced consistent results among the individual experiments and between combined and individual data sets. Each dendrogram had two major branches, indicating two epitopes. Antibodies that clustered together for multiple individual data sets also clustered together or were in neighboring clusters for the combined data set. As shown in Table 3, below, there were only two minor discrepancies in the clustering results across different experiments or between an individual experiment and the combined data set, where these discrepancies are indicated by bold type in Table 3. In a data set generated in Experiment 3, D111 clustered with antibodies a33 and K221, instead of HR26 and a215. In a data set generated in Experiment 4, antibodies a203, a393, and a452 appeared in the first cluster, whereas in another experiment (as well as in the combined data set), they appeared in a second cluster. This slight difference is likely attributable to differences in individual antibody affinity between experiments in which the antibody is used as a probe antibody and experiments in which the same antibody is used as a reference antibody. Antibodies with lower affinity may have a reduced capacity to capture antigen out of the solution when used as a reference antibody. However, the overall similarity of the clustering results, as well as the grouping of the antigens, indicated that the process produced consistent clustering results that were in good agreement with results from other experiments across multiple individual experiments, and that the results remained consistent when multiple data sets were merged.

Finally, there was a high level of consistency in clustering results for each of these data sets when the process was used to cluster by rows and by columns, for the individual and combined data sets. The only discrepancy in the clustering results between row and column clusterings was with D111 in the third data set, in which it clustered with antibodies HR26 and a215 when row clustering was performed, whereas D111 clustered with antibodies a33 and K221 when column clustering was performed.

TABLE B

Results of Clustering for Individual and Combined Data Sets

| Cluster | Expt1 Rows | Expt1 Cols | Expt2 Rows | Expt2 Cols | Expt3 Rows | Expt3 Cols | Expt4 Rows | Expt4 Cols | Expt5 Rows | Expt5 Cols | Comb Rows | Comb Cols |
|---|---|---|---|---|---|---|---|---|---|---|---|---|
| 1 | a809 a928 HR26 | a809 a928 HR26 | D111 HR26 a215 | D111 HR26 a215 | D111 HR26 a215 | HR26 a215 | HR26 a215 a203 a393 a452 | HR26 a215 a203 a393 a452 | HR26 a215 | HR26 a215 | a809 a928 D111 HR26 a215 | a809 a928 D111 HR26 a215 |
| 2 | a837 K221 | a837 K221 | a33 K221 | a33 K221 | a33 K221 | D111 a33 K221 | a33 K221 | a33 K221 | a33 K221 a203 a393 a452 a142 a358 | a33 K221 a203 a393 a452 a142 a358 | a837 a33 K221 a142 a358 a203 a393 a452 | a837 a33 K221 a142 a358 a203 a393 a452 |

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. An antibody competition assay method for determining antibodies that bind to an epitope on an antigen, comprising:
   providing a set of antibodies that bind to an antigen;
   labeling each antibody of said set to form a labeled reference antibody set such that each labeled reference antibody is distinguishable from every other labeled reference antibody in said labeled reference antibody set;
   selecting a probe antibody from said set of antibodies that bind to the antigen;
   contacting said probe antibody with said labeled reference antibody set in the presence of said antigen;
   detecting said probe antibody in a complex comprising said antigen, one labeled reference antibody bound to said antigen, and said labeled probe antibody bound to said antigen;
   identifying each said labeled reference antibody bound to said antigen in each said complex;
   determining whether said probe antibody competes with any reference antibody in said labeled reference antibody set, wherein competition indicates that said probe antibody binds to the same epitope as another antibody in said set of antibodies that bind to an antigen.

2. The method of claim 1, further comprising labeling said probe antibody to form a labeled probe antibody.

3. The method of claim 2, wherein said labeled probe antibody comprises a label selected from an enzymatic label, a colorimetric label, a fluorescent label, or a radioactive label.

4. The method of claim 1, further comprising providing a labeled detection antibody for detecting said probe antibody.

5. The method of claim 4, wherein said labeled detection antibody comprises a label selected from an enzymatic label, a colorimetric label, a fluorescent label, or a radioactive label.

6. The method of claim 1, wherein each antibody of set of antibodies that bind to an antigen is labeled with a uniquely colored bead to form a labeled reference antibody set such that each labeled reference antibody is distinguishable from every other labeled reference antibody in said labeled reference antibody set.

7. The method of claim 6, wherein said each uniquely colored bead has a distinct emission spectrum.

8. The method of claim 6, wherein said probe antibody is a labeled probe antibody.

9. The method of claim 6, further comprising providing a labeled detection antibody for detecting said probe antibody.

10. The method of claim 1, further comprising a method for characterizing antibodies based on binding characteristics, comprising:
    providing input data representing the outcomes of at least one antibody competition assay using a set of antibodies that bind to an antigen;
    normalizing said input data to generate a normalized intensity matrix;
    computing at least one dissimilarity matrix comprising generating a threshold matrix from said normalized intensity matrix and computing a dissimilarity matrix from said threshold matrix; and
    clustering antibodies based on dissimilarity values in cells of said dissimilarity matrix, to determine epitope binding patterns of said set of antibodies that bind to an antigen.

11. The method of claim 10, wherein the Competitive Pattern Recognition (CPR) process is used for characterizing antibodies based on binding characteristics.

12. The method of claim 10 wherein said input data is generated by a high throughput competitive antibody assay.

13. The method of claim 12, wherein said high throughput competitive antibody assay is the Multiplexed Competitive Antibody Binning (MCAB) assay.

14. The method of claim 10, wherein said input data comprises signal intensity values representing the outcomes of at least one antibody competition assay using a set of antibodies that bind to an antigen.

15. The method of claim 14, wherein said input data comprising signal intensity values representing the outcomes of at least one antibody competition assay comprises input data stored in matrix form.

16. The method of claim 15, wherein said input data stored in matrix form comprises a two-dimensional matrix.

17. The method of claim 15, wherein said data stored in matrix form comprises a multidimensional matrix.

18. The method of claim 15 wherein said input data stored in matrix form comprises a plurality of matrices.

19. The method of claim 15, wherein said input data stored in matrix form comprises signal intensity values representing the outcomes of an antibody competition assay carried out using a multi-well format, wherein each cell of said matrix represents the outcome of the assay carried out in one well of said multi-well format.

20. The method of claim 15, wherein said normalizing said input data to generate a normalized intensity matrix comprises generating a background-normalized intensity matrix by subtracting a first matrix comprising signal intensity values from a first antibody competition assay in which antigen was not added, from a second matrix comprising signal intensity values from a second antibody competition assay in which antigen was added.

21. The method of claim 20, comprising setting a minimum threshold value for blocking buffer values and adjusting any blocking buffer values below said threshold value to said threshold value prior to generating said normalized intensity matrix.

22. The method of claim 21, further comprising dividing each value in a column of said background-normalized intensity matrix by the blocking buffer intensity value for said column.

23. The method of claim 22, wherein said normalizing step further comprises normalizing relative to the baseline signal for probe antibodies, comprising dividing each said column of said intensity-normalized matrix by its corresponding diagonal value to generate a final intensity-normalized matrix.

24. The method of claim 23, wherein each said diagonal value is compared with a user-defined threshold value and any said diagonal value below said user-defined threshold value is adjusted to said threshold value prior to said dividing each column by its corresponding diagonal value.

25. The method of claim 21, wherein said normalizing step further comprises generating an intensity-normalized matrix by dividing each value in a row of said background-normalized intensity matrix by the blocking buffer intensity value for said row.

26. The method of claim 25, wherein said normalizing step further comprises normalizing relative to the baseline signal for probe antibodies, comprising dividing each said row of said intensity-normalized matrix by its corresponding diagonal value to generate a final intensity-normalized matrix.

27. The method of claim 26, wherein each said diagonal value is compared with a user-defined threshold value and any said diagonal value below said user-defined threshold value is adjusted to said threshold value prior to said dividing each row by its corresponding diagonal value.

28. The method of claim 20, wherein said generating said threshold matrix comprises setting the normalized valued in each cell of said normalized intensity matrix to a value of one (1) or zero (0), wherein normalized values less than or equal to a threshold value are set to a value of zero (0) and normalized values greater to said threshold value are set to a value of one (1).

29. The method of claim 28, wherein said at least one dissimilarity matrix is computed by providing said threshold matrix of ones and zeroes and determining the number of positions in which each pair of rows differs.

30. The method of claim 29, wherein a plurality of dissimilarity matrices are computing using a plurality of threshold values.

31. The method of claim 30, wherein the average of said plurality of dissimilarity matrices is computed.

32. The method of claim 31, comprising providing said average of said plurality of dissimilarity matrices as input to said clustering step.

33. The method of claim 10, wherein said clustering antibodies based on said dissimilarity values in cells of said dissimilarity matrix comprises hierarchical clustering.

34. The method of claim 33, wherein said hierarchical clustering comprises generating a hierarchy of nested subsets of antibodies within said set of antibodies that bind to an antigen, comprising:
determining the pair of antibodies in said set having the lowest dissimilarity value;
determining the pair of antibodies having the next lowest dissimilarity value;
interatively repeating said determining said pair of antibodies having the next lowest dissimilarity value until one pair of antibodies remains, such that a hierarchy of nested subsets is generated that indicates the similarity of competition patterns within said set of antibodies; and
determining clusters based on competition patterns.

35. The method of claim 34, wherein data from said clustering step is captured.

36. The method of claim 35, wherein data is captured by automated means.

37. The method of claim 34, wherein said clustering step generates a display.

38. The method of claim 37, wherein said display is in a format compatible with data input device or computer.

39. The method of claim 37, wherein said display comprises a dissimilarity matrix.

40. The method of claim 39, wherein clusters are determined by visual inspection of the dissimilarity value in each cell of said dissimilarity matrix.

41. The method of claim 39, wherein said dissimilarity matrix comprises cells having a visual indicator of the cluster to which the antibody pair represented by said cell belongs.

42. The method of claim 41, wherein said visual indicator is a color.

43. The method of claim 41, wherein said visual indicator is shading.

44. The method of claim 41, wherein said visual indicator is patterning.

45. The method of claim 37, wherein said display is a dendrogram defined by dissimilarity values computed for said set of antibodies.

46. The method of claim 45, wherein said dendrogram comprises branches representing antibodies in said set of antibodies, wherein the arrangement of branches represents relationships between antibodies within said set of antibodies, further wherein said arrangement represents clusters of antibodies within said set of antibodies.

47. The method of claim 46, further wherein said dendrogram comprises branches wherein the length of any said branch represents the degree of similarity between the binding pattern of antibodies or cluster of antibodies represented by said branch.

48. The method of claim 10, comprising providing input data representing the outcomes of a plurality of antibody competition assays, wherein each assay represents an individual experiment using a set of antibodies that bind to an antigen, further wherein each said experiment comprises at least one antibody that is also tested in at least one other experiment.

49. The method of claim 48, comprising generating an individual normalized intensity matrix for each said individual experiment and further comprising generating a single normalized intensity matrix by computing the average intensity value of each antibody pair represented in each individual normalized intensity matrix.

50. The method of claim 49, further comprising generating a single dissimilarity matrix representing each antibody pair tested in said plurality of antibody competition assays.

51. A method for characterizing antibodies based on binding characteristics, comprising:
providing a labeled reference antibody set such that each labeled reference antibody in said set is distinguishable from every other labeled reference antibody in said labeled reference antibody set, and wherein each antibody binds to an antigen;
selecting a probe antibody from said set of antibodies that binds to the antigen;
contacting said probe antibody with said labeled reference antibody set in the presence of said antigen;
detecting said probe antibody in a complex comprising said antigen, one labeled reference antibody bound to said antigen, and said labeled probe antibody bound to said antigen;
identifying each said labeled reference antibody bound to said antigen in each said complex;
determining whether said probe antibody competes with any reference antibody in said labeled reference antibody set, wherein competition indicates that said probe antibody binds to the same epitope as another antibody in said set of antibodies that bind to an antigen;
providing input data representing the outcomes of at least one antibody competition assay using a set of antibodies that bind to an antigen, further wherein said input data comprises signal intensity values representing the outcomes of at least one antibody competition assay using a set of antibodies that bind to an antigen;
storing said input data in matrix format;
subtracting a first matrix comprising signal intensity values from a first antibody competition assay in which antigen was not added, from a second matrix comprising signal intensity values from a second antibody competition assay in which antigen was added, to form a background normalized intensity matrix;
calculating the value in each diagonal cell of said background normalized intensity matrix;
determining cells in each column of said background normalized intensity matrix having values significantly higher than the value in each diagonal cell of said column; and
grouping columns having similar binding patterns as a bin.

52. The method of claim 51, wherein said cells in said background normalized intensity matrix having values significantly higher than said value in each corresponding diagonal cell of said column have values at least two times said value in each diagonal cell.

* * * * *